(12) United States Patent
Jagtap et al.

(10) Patent No.: US 6,828,319 B2
(45) Date of Patent: Dec. 7, 2004

(54) SUBSTITUTED INDENO[1,2-C] ISOQUINOLINE DERIVATIVES AND METHODS OF USE THEREOF

(75) Inventors: Prakash Jagtap, Beverly, MA (US); Erkan Baloglu, Stoneham, MA (US); John H. van Duzer, Boston, MA (US); Csaba Szabo, Gloucester, MA (US); Andrew L. Salzman, Belmont, MA (US)

(73) Assignee: Inotek Pharmaceuticals Corporation, Beverly, MA (US)

( * ) Notice: Subject to any disclaimer, the term of this patent is extended or adjusted under 35 U.S.C. 154(b) by 0 days.

(21) Appl. No.: 10/233,198

(22) Filed: Aug. 30, 2002

(65) Prior Publication Data

US 2003/0171392 A1 Sep. 11, 2003

Related U.S. Application Data

(63) Continuation-in-part of application No. 09/944,524, filed on Aug. 31, 2001, now abandoned.

(51) Int. Cl.$^7$ .................. A61K 31/5377; A61K 31/473; C07D 413/12; C07D 221/18
(52) U.S. Cl. .................... 514/232.8; 544/125; 544/361; 546/61; 546/62; 546/70; 514/253; 514/254; 514/284; 514/285
(58) Field of Search ................................ 514/284, 285, 514/232.8, 253, 254, 232.5; 544/125, 361; 546/61, 62, 70

(56) References Cited

U.S. PATENT DOCUMENTS

| | | | |
|---|---|---|---|
| 3,710,795 A | 1/1973 | Higuchi et al. | |
| 5,079,246 A | 1/1992 | Forbes et al. | |
| 5,260,316 A | 11/1993 | Van Duzer et al. | |
| 5,262,564 A | 11/1993 | Kun et al. | |
| 5,597,831 A | 1/1997 | Michalsky, deceased et al. | |
| 6,346,535 B1 | 2/2002 | Cotter et al. | |
| 6,346,536 B1 | 2/2002 | Li et al. | |
| 6,498,194 B2 | 12/2002 | Cotter et al. | |
| 6,635,642 B1 | 10/2003 | Jackson et al. | |
| 2002/0099063 A1 | 7/2002 | Cotter et al. | |
| 2004/0039009 A1 | 2/2004 | Jagtap et al. | |

FOREIGN PATENT DOCUMENTS

| | | |
|---|---|---|
| WO | WO 93/05023 | 3/1993 |
| WO | WO 99/11311 | 3/1999 |
| WO | WO 99/11623 | 3/1999 |
| WO | WO 99/11628 | 3/1999 |
| WO | WO 99/11644 | 3/1999 |
| WO | WO 99/11645 | 3/1999 |
| WO | WO 99/11649 | 3/1999 |
| WO | WO 99/59973 | 11/1999 |
| WO | WO 99/59975 | 11/1999 |
| WO | WO 00/21537 | 4/2000 |
| WO | WO 00/39070 | 7/2000 |
| WO | WO 00/39104 | 7/2000 |
| WO | WO 00/42040 | 7/2000 |

OTHER PUBLICATIONS

Yamaguchi, S. et al. : The synthesis of Benzofuroquinolines. J. Heterocyclic Chem. vol. 32, pp. 419–423, 1995.*
Hiremath, S.P. et al. : A new method of synthesis of 6h, 11H–indolo[3,2–c]–isoquinolin–5–ones/thiones and their reactions. J. Heterocyclic Chem. vol. 30, pp. 603–609, 1993.*
Abdelkarim et al., 2001, "Protective effects of PJ34, a novel, potent inhibitor of poly(ADP–ribose) polymerase (PARP) in in vitro and in vivo models of stroke", Int. J. Mol. Med. 7:255–260.
Ando et al., 1974, "Cyclization reactions of 1,2–bis(2–cyanophenyl)propionitriles. II. Synthesis of 5–amino–4,7–dimethoxy–11H–indeno[1,2–c]isoquinolin–11–one", Bull. Chem. Soc. Japan 47:1014–1017.
Banasik and Ueda, 1994, "Inhibitors and activators of ADP–ribosylation reactions", Mol. Cell. Biol. 138:185–197.
Banasik et al., 1992, "Specific inhibitors of poly(ADP–ribose) synthetase and mono(ADP–ribosyl) transferase", J. Biol. Chem. 267:1569–1575.
Cushman et al., 2000, "Synthesis of new indeno[1,2–c] isoquinolines: Cytotoxic non–camptothecin topoisomerase I inhibitors", J. Med. Chem. 43:3688–3698.
Dusemund and Kröger, 1984, "5–hydroxyisoindolo[2,1b] isoquinolin–7–one: Synthesis and isomerization", Arch. Pharm. (Weinheim) 317:381–382.
Griffin et al., 1998, "Resistance–modifying agents. 5. Synthesis and biological properties of quinazolinone inhibitors of the DNA repair enzyme poly(ADP–ribose) polymerase (PARP)", J. Med. Chem. 41:5247–5256.
Grupp et al., 1999, "Protection against hypoxia–reoxygenation in the absence of poly(ADP–ribose) synthetase in isolated working hearts", J. Mol. Cell Cardiol. 31:297–303.
Lal and Gidwani, 1999, "Applications of carbon–nitrogen bond cleavage reaction: A synthesis/derivisation of 11H–indeno[1,2–c]isoquinolines", Ind. J. Chem. 38B:33–39.
Lamping et al., 1998, "LPS–binding protein protects mice from septic shock caused by LPS or gram–negative bacteria", J. Clin. Invest. 101:2065–2071.
Mabley et al., 2001, "Inhibition of poly(ADP–ribose) synthetase by gene disruption or inhibition with 5–iodo–6–amino–1,2–benzopyrone protects mice from multiple–low–dose–streptozotocin–induced diabetes", Br. J. Pharmacol. 133:909–919.

(List continued on next page.)

Primary Examiner—Charanjit S. Aulakh
(74) Attorney, Agent, or Firm—Wilmer Cutler Pickering Hale and Dorr LLP

(57) ABSTRACT

The invention provides novel classes of substituted Indeno [1,2-c]isoquinoline Compounds. Pharmaceutical compositions and methods of making and using the compounds, are also described.

131 Claims, No Drawings

OTHER PUBLICATIONS

Milam and Cleaver, 1984, "Inhibitors of poly(adenosine diphosphate–ribose) synthesis: Effect on other metabolic processes", Science 223:589–591.

Parrillo, 1993, "Pathogenic mechanisms of septic shock", N. Eng. J. Med. 328:1471–1477.

Shinkwin et al., 1999, "Synthesis of thiophenecarboxamides, thieno[3,4–c]pyridin–4(5H)–ones and thio[3,4–d]pyrimidin–4(3H)–ones and preliminary evaluation as inhibitors of poly(ADP–ribose) polymerase (PARP)", Bioorg. & Med. Chem. 7:297–308.

Soriano et al., 2001, "Diabetic endothelial dysfunction: the role of poly(ADP–ribose) polymerase activation", Nature Med. 7:108–113.

Strumberg et al., 1999, "Synthesis of cytotoxic indenosoquinoline topoisomerase I poisons", J. Med. Chem. 42:446–457.

Szabo and Dawson, 1998, "Role of poly(ADP–ribose) synthetase in inflammation and ischaemia–reperfusion", TIPS 19:287–298.

Szabo, 1996, "The pathophysiological role of peroxynitrite in shock, inflammation, and ischemia–reperfusion injury", Shock 6:79–88.

Virág et al., 1998, "Peroxynitrite–induced thymocyte apoptosis: the role of caspases and poly(ADP–ribose) synthetase (PARS) activation", Immunol. 94:345–355.

Wawzonek, 1982, "Synthesis of 6–substituted–6H–indeno[1,2–c]isoquinoline–5,11–diones", Org. Prep. Proc. Int. 14:163–168.

Wawzonek, 1981, "Preparation and reactions of 4b–acetoxy–4b,9b–dihydroindeno[2,1–a]indene–5,10–dione", Can. J. Chem. 59:2833–2834.

White et al., 2000, "Resistance–Modifying Agents. Synthesis and Biological Properties of Benzimidazole Inhibitors of the DNA Repari Enzyme Poly(ADP–ribose Polymerase", J. Med. Chem. 43:4084–4097.

Zhang et al., 2000, "GPI 6150 Prevents $H_2O_2$ Cytotoxicity by Inhibiting Poly(ADP–ribose) Polymerase", Biochem and Biophys Res. Commun. 278:590–598.

Aldrich, p. 32, Aldrich Chemical Company, 1992.

Hakimelahi et al., 1987, "Ring Open Analogues of Adenine Nucleoside, Aminoacyl Derivatives of Cyclo– and Acyclo––nucleosides", Helvetica Chimica Acta 70:219–231.

Burger's Medicinal Chemistry and Drug Discovery, $5^{th}$ ed., vol. 1: Principles and Practice, John Wiley and Sons, Inc.975–977.

Kawana t al., 1972, "Nucleoside Peptides. III. The Synthesis of N–[1–(9–Adenyl)–β–D–ribofuranuronosyl] Derivatives of Certain Amino Acids and Peptides", J. Org. Chem. 37(2):288–290.

Ojika et al., 1987, "Ptaquiloside, a Potent Carcinogen Isolated From Bracken Fem Pteridium Aquilinum Var. Latiusculum: Structure Elucidation Based On Chemical and Spectral Evidence, and Reactions with Amino Acids, Nucleosides, and Nucleotides", Tetrahedron 43:5261–5274.

Bloch et al., 1967, "The role of the 5'–hydroxyl group of adenosine in determining substrate specificity for adenosine deaminase",J Med Chem. 10(5):908–12.

Hiremath et al., 1993, "A New Method for the Synthesis of 6H,11H–indolo[3,2–c]–isoquinolin–5–ones/thiones and their Reactions", J. Heterocycl. Chem 30:603–609.

Yamaguchi et al., 1994, "The Synthesis of Benzofuroquinolines. IX. A Benzofuroisoquinolinone and a Benzofuroisocoumarin", J. Heterocycl. Chem. 32:419–423.

Mandir et al., 2002, "A novel in vivo post–translational modification of p53 by PARP–1 in MPTP–induced parkinsonism",J Neurochem. Oct. 2002;83(1):186–92.

Mandir et al., 1999, "Poly(ADP–ribose) polymerase activation mediates 1–methyl–4–phenyl–1, 2,3,6–tetrahydropyridine (MPTP)–induced parkinsonism"Proc Natl Acad Sci U S A. 96(10):5774–9.

Wang et al., 2003, "Apoptosis Inducing factor and PARP-mediated injury in the MPTP mouse model of Parkinson's disease", Ann N Y Acad Sci. 991:132–9.

Jantzen and Robinson, Modern Pharmaceutics, $3^{rd}$. ed., eds. Baker and Rhodes, p. 596.

\* cited by examiner

SUBSTITUTED INDENO[1,2-C] ISOQUINOLINE DERIVATIVES AND METHODS OF USE THEREOF

This application is a continuation-in-part of U.S. application Ser. No. 09/944,524, filed Aug. 31, 2001, now abandoned which is incorporated by reference herein in its entirety.

1. FIELD OF THE INVENTION

The invention relates to indeno[1,2-c]isoquinoline compounds; compositions comprising an indeno[1,2-c]isoquinoline compound; and methods for treating or preventing an inflammatory disease or a reperfusion disease.

2. BACKGROUND OF THE INVENTION

Inflammatory diseases, such as arthritis, colitis, and autoimmune diabetes, typically manifest themselves as disorders distinct from those associated with reperfusion diseases, e.g., stroke and heart attack, and can clinically manifest themselves as different entities. However, there can be common underlying mechanisms between these two types of disorders. In particular, inflammatory disease and reperfusion disease can induce proinflammatory cytokine and chemokine synthesis which can, in turn, result in production of cytotoxic free radicals such as nitric oxide and superoxide. NO and superoxide can react to form peroxynitrite ($ONOO^-$) (Szabó et al., Shock 6:79–88, 1996).

The $ONOO^-$-induced cell necrosis observed in inflammatory disease and in reperfusion disease involves the activation of the nuclear enzyme poly (ADP-ribose) synthetase (PARS). Activation of PARS is thought to be an important step in the cell-mediated death observed in inflammation and reperfusion disease (Szabó et al., Trends Pharmacol. Sci. 19: 287–98, 1998).

A number of PARS inhibitors have been described in the art. See, e.g., Banasik et al., J. Biol. Chem., 267:1569–75, 1992, and Banasik et al., Mol. Cell. Biochem., 138:185–97, 1994; WO 00/39104; WO 00/39070; WO 99/59975; WO 99/59973; WO 99/11649; WO 99/11645; WO 99/11644; WO 99/11628; WO 99/11623; WO 99/11311; WO 00/42040; Zhang et al., Biochem. Biophys. Res. Commun., 278:590–98,2000; White et al., J. Med. Chem., 43:4084–4097, 2000; Griffin et al., J. Med. Chem., 41:5247–5256, 1998; Shinkwin et al., Bioorg. Med. Chem., 7:297–308, 1999; and Soriano et al., Nature Medicine, 7:108–113, 2001. Adverse effects associated with administration of PARS inhibitors have been discussed in Milan et al, Science, 223:589–591, 1984.

Indeno[1,2-c]isoquinoline derivatives have been previously discussed in the art. For example, cytotoxic non-camptothecin topoisomerase I inhibitors are reported in Cushman et al., J. Med. Chem., 43:3688–3698, 2000 and Cushman et al., J. Med. Chem. 42:446–57, 1999; indeno[1,2-c]isoquinolines are reported as antineoplastic agents in Cushman et al., WO 00/21537; and as neoplasm inhibitors in Hrbata et al., WO 93/05023.

Syntheses of indeno[1,2-c]isoquinoline derivatives have been reported. For example, see Wawzonek et al., Org. Prep. Proc. Int. 14:163–8, 1982; Wawzonek et al., Can. J. Chem. 59:2833, 1981; Andoi et al, Bull. Chem. Soc. Japan, 47:1014–17, 1974; Dusemund et al., Arch. Pharm (Weinheim, Ger.), 3 17:381–2, 1984; and Lal et al., Indian J. Chem., Sect. B, 38B:33–39, 1999.

There remains, however, a need in the art for compounds useful for treating or preventing inflammatory diseases or reperfusion diseases.

Citation of any reference in Section 2 of this application is not an admission that the reference is prior art.

3. SUMMARY OF THE INVENTION

The invention is based in part on the discovery of novel substituted tetracyclic benzamide derivatives and their demonstrated effects in the treatment of inflammation, cell death and in treating shock and reperfusion diseases.

Accordingly, in one aspect the invention includes a compound of Formula I, Formula Ia, Formula Ib, Formula II or Formula III, or a pharmaceutically acceptable salt or hydrate thereof (an "Indeno[1,2-c]isoquinoline Compound") as set forth below in the detailed description of the invention.

Also provided by the invention is a method for treating or preventing an inflammatory disease or a reperfusion diseasein a subject, comprising administering to a subject in need of such treatment or prevention an effective amount of an Indeno[1,2-c]isoquinoline Compound.

In a further aspect, the invention also includes a method for making an Indeno[1,2-c]isoquinoline Compound.

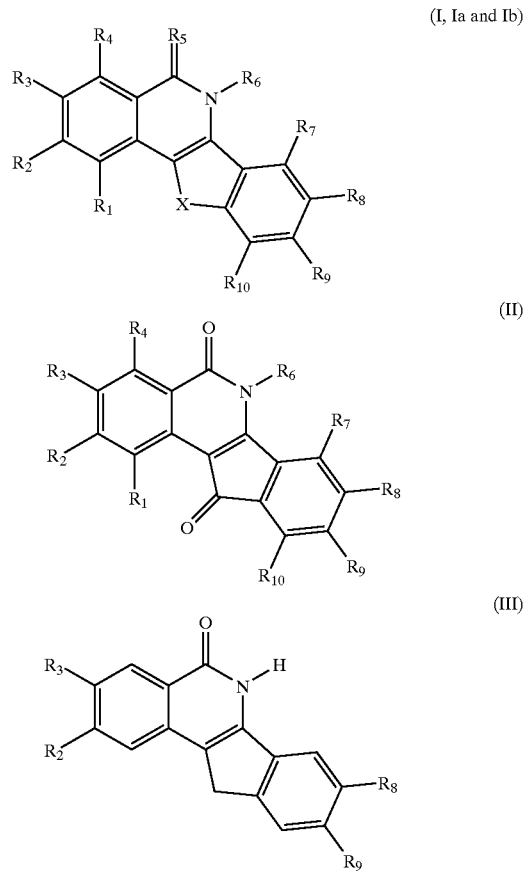

The Indeno[1,2-c]isoquinoline Compounds can be used to treat or prevent a variety of conditions and diseases, including, but not limited to, an inflammatory disease or a reperfusion disease.

The invention also includes pharmaceutical compositions that comprise an effective amount of an Indono[1,2-c]isoquinoline Compound and a pharmaceutically acceptable carrier. The compositions are useful for treating or preventing an inflammatory disease or a reperfusion disease. The invention includes an Indeno[1,2-c]isoquinoline Compound when provided as a pharmaceutically acceptable prodrug, a hydrated salt, such as a pharmaceutically acceptable salt, or mixtures thereof.

The details of the invention are set forth in the accompanying description below. Although any methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

4. DETAILED DESCRIPTION OF THE INVENTION

The present invention provides a novel class of Indeno [1,2-c]isoquinoline Compounds according to Formula I, Formula Ia, Formula Ib, Formula II and Formula II, as set forth below:

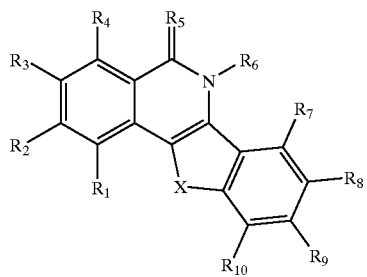

(I)

and pharmaceutically acceptable salts and hydrates thereof, wherein:

$R_5$ is O, NH or S;

$R_6$ is —H or $C_1$–$C_4$ alkyl;

X is —C(O)—, —CH$_2$—, —CH(halo)-, —CH(OH)(CH$_2$)$_n$—, —CH(OH)-arylene-, —O—, —NH—, —S— or —CH(NR$_{11}$R$_{12}$)—, wherein n is an integer ranging from 0–5;

$R_{11}$, and $R_{12}$ are independently -hydrogen or —C$_1$–C$_9$ alkyl, or N, $R_{11}$ and $R_{12}$ are taken together to form a heterocyclic amine;

$R_1$, $R_2$, $R_3$, $R_4$, $R_7$, $R_8$, $R_9$ and $R_{10}$ are independently -hydrogen, -halo, -hydroxy, —O—(C$_1$–C$_5$ alkyl), —C$_1$–C$_{10}$ alkyl, -alkylhalo, —C$_2$–C$_{10}$ alkenyl, —C$_3$–C$_8$ carbocycle, -aryl, —NH$_2$, -alkylamino, —C(O)OH, —C(O)O(C$_1$–C$_5$ alkyl), —OC(O)(C$_1$–C$_5$ alkyl), NO$_2$ or -A-B;

wherein A is —SO$_2$—, —SO$_2$NH—, —NHCO—, —NHCONH—, —O—, —CO—, —OC(O)—, —C(O)O—, —CONH—, —CON(C$_1$–C$_4$ alkyl)-, —NH—, —CH$_2$—, —S— or —C(S)—;

B is —C$_1$–C$_{10}$ alkyl, —C$_2$–C$_{10}$ alkenyl, -heterocycle, —C$_3$–C$_8$ carbocycle, -aryl, —NZ$_1$Z$_2$, -alkylamino, -aminodialkyl, -alkylheterocycle, -arylamido, —C(O)OH, —C(O)O—(C$_1$–C$_5$ alkyl) or —C(O)O-phenyl, any of which are unsubstituted or substituted with one or more of —O—(C$_1$–C$_5$ alkyl), -halo, -alkylhalo, -alkanol, -alkylamino, -hydroxy, —NO$_2$, —NH$_2$, -aminoalkyl, -aminodialkyl, -heterocyclic amine, —C$_1$–C$_{10}$ alkyl, —C$_2$–C$_{10}$ alkenyl, —C$_2$–C$_{10}$ alkynyl, -aryl, -benzyl, -alkylamido, -alkylcarboxy, —C$_1$–C$_5$ alkylene-C(O)O—C$_1$–C$_5$ alkyl or —C$_1$–C$_5$ alkylene-OC(O)—C$_1$–C$_5$ alkyl groups; and $Z_1$ and $Z_2$ are independently —H or —C$_1$–C$_{10}$ alkyl, which is unsubstituted or substituted with one or more of -halo, —OH or —N(Z$_3$)(Z$_4$), where Z$_3$ and Z$_4$ are independently, —H or —C$_1$–C$_5$ alkyl, which is unsubstituted or substituted with one or more of -halo, -hydroxy or —NH$_2$; or N, Z$_3$ and Z$_4$ are taken together to form an unsubstituted or substituted heterocyclic amine; or N, Z$_1$ and Z$_2$ are taken together to form a heterocyclic amine.

The invention also relates to a compounds of formula (Ia):

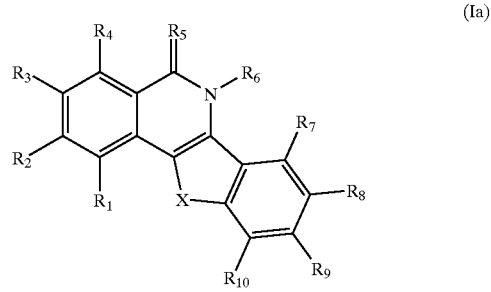

(Ia)

and pharmaceutically acceptable salts and hydrates thereof, wherein:

$R_5$ is NH or S;

$R_6$ is —H or $C_1$–$C_4$ alkyl;

X is —C(O)—, —CH$_2$—, —CH(halo)-, —CH(OH)(CH$_2$)$_n$—, —CH(OH)-arylene-, —O—, —NH—, —S— or —CH(NR$_{11}$R$_{12}$)—, wherein n is an integer ranging from 0–5;

$R_{11}$ and $R_{12}$ are independently -hydrogen or —C$_1$–C$_9$ alkyl, or N, $R_{11}$ and $R_{12}$ are taken together to form a heterocyclic amine;

$R_1$, $R_2$, $R_3$, $R_4$, $R_7$, $R_8$, $R_9$ and $R_{10}$ are independently -hydrogen, -halo, -hydroxy, —O—(C$_1$–C$_5$ alkyl), —C$_1$–C$_{10}$ alkyl, -alkylhalo, —C$_2$–C$_{10}$ alkenyl, —C$_3$–C$_8$ carbocycle, -aryl, —NH$_2$, -alkylamino, —C(O)OH, —C(O)O(C$_1$–C$_5$ alkyl), —OC(O)(C$_1$–C$_5$ alkyl), NO$_2$ or -A-B;

wherein A is —SO$_2$—, —SO$_2$NH—, —NHCO—, —NHCONH—, —O—, —CO—, —OC(O)—, —C(O)O—, —CONH—, —CON(C$_1$–C$_4$ alkyl)-, —NH—, —CH$_2$—, —S— or —C(S)—;

B is —C$_1$–C$_{10}$ alkyl, —C$_2$–C$_{10}$ alkenyl, -heterocycle, —C$_3$–C$_8$ carbocycle, -aryl, —NZ$_1$Z$_2$, -alkylamino, -aminodialkyl, -alkylheterocycle, -arylamido, —C(O)OH, —C(O)O—(C$_1$–C$_5$ alkyl) or —C(O)O-phenyl, any of which are unsubstituted or substituted with one or more of —O—(C$_1$–C$_5$ alkyl), -halo, -alkylhalo, -alkanol, -alkylamino, -hydroxy, —NO$_2$, —NH$_2$, -aminoalkyl, -aminodialkyl, -heterocyclic amine, —C$_1$–C$_{10}$ alkyl, —C$_2$–C$_{10}$ alkenyl, —C$_2$–C$_{10}$ alkynyl, -aryl, -benzyl, -alkylamido, -alkylcarboxy, —C$_1$–C$_5$ alkylene-C(O)O—C$_1$–C$_5$ alkyl or —C$_1$–C$_5$ alkylene-OC(O)—C$_1$–C$_5$ alkyl groups; and $Z_1$ and $Z_2$ are independently —H or —C$_1$–C$_{10}$ alkyl, which is unsubstituted or substituted with one or more of -halo, —OH or —N(Z$_3$)(Z$_4$), where Z$_3$ and Z$_4$ are independently, —H or —C$_1$–C$_5$ alkyl, which is unsubstituted or substituted with one or more of -halo, -hydroxy or —NH$_2$; or N, Z$_3$ and Z$_4$ are taken together to form an unsubstituted or substituted heterocyclic amine; or N, Z$_1$ and Z$_2$ are taken together to form a heterocyclic amine.

In one embodiment, A is —SO$_2$—.

In another embodiment, $R_1$, $R_2$, $R_3$, $R_4$, $R_7$, $R_8$, $R_9$ and $R_{10}$ are independently arylalkyl.

In other illustrative embodiments R$^5$ and X in a compound of formula Ia are as set forth below:

| $R^5$ | X |
|---|---|
| NH | —C(O)— |
| NH | —CH$_2$— |
| NH | —CH(halo)— |
| NH | —CH(OH)(CH$_2$)$_n$— |
| NH | —CH(arylene)(OH)— |
| NH | —O— |
| NH | —NH— |
| NH | —S— |
| NH | —CH(NR$^{11}$R$^{12}$)— |
| S | —C(O)— |
| S | —CH$_2$— |
| S | —CH(halo)— |
| S | —CH(OH)(CH$_2$)$_n$— |
| S | —CH(arylene)(OH)— |
| S | —O— |
| S | —NH— |
| S | —S— |
| S | —CH(NR$^{11}$R$^{12}$)— |

The invention also relates to compounds of Formula Ib:

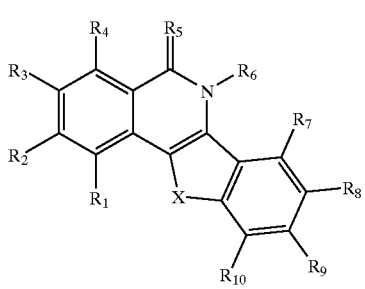

(Ib)

and pharmaceutically acceptable salts and hydrates thereof, wherein:

$R_5$ is O, NH or S;
$R_6$ is —H or $C_1$–$C_4$ alkyl;
X is —CH$_2$—, —CH(halo)-, —CH(OH)(CH$_2$)$_n$—, —CH(OH)-arylene-, —O—, —NH—, —S— or —CH(NR$_{11}$R$_{12}$)—, wherein n is an integer ranging from 0–5;
$R_{11}$ and $R_{12}$ are independently -hydrogen or —C$_1$–C$_9$ alkyl, or N, $R_{11}$ and $R_{12}$ are taken together to form a heterocyclic amine.
$R_1$, $R_2$, $R_3$, $R_4$, $R_7$, $R_8$, $R_9$ and $R_{10}$ are independently -hydrogen, -halo, -hydroxy, —O—(C$_1$–C$_5$ alkyl), —C$_1$–C$_{10}$ alkyl, -alkylhalo, —C$_2$–C$_{10}$ alkenyl, —C$_3$–C$_8$ carbocycle, -aryl, —NH$_2$, -alkylamino, —C(O)OH, —C(O)O(C$_1$–C$_5$ alkyl), —OC(O)(C$_1$–C$_5$ alkyl), NO$_2$ or -A-B;
wherein A is —SO$_2$—, —SO$_2$NH—, —NHCO—, —NHCONH—, —O—, —CO—, —OC(O)—, —C(O)O—, —CONH—, —CON(C$_1$–C$_4$ alkyl)-, —NH—, —CH$_2$—, —S— or —C(S)—;
B is —C$_1$–C$_{10}$ alkyl, —C$_2$–C$_{10}$ alkenyl, -heterocycle, —C$_3$–C$_8$ carbocycle, -aryl, —NZ$_1$Z$_2$, -alkylamino, -aminodialkyl, -alkylheterocycle, -arylamido, —C(O)OH, —C(O)O—(C$_1$–C$_5$ alkyl) or —C(O)O-phenyl, any of which are unsubstituted or substituted with one or more of —O—(C$_1$–C$_5$ alkyl), -halo, -alkylhalo, -alkanol, -alkylamino, -hydroxy, —NO$_2$, —NH$_2$, -aminoalkyl, -aminodialkyl, -heterocyclic amine, —C$_1$–C$_{10}$ alkyl, —C$_2$–C$_{10}$ alkenyl, —C$_2$–C$_{10}$ alkynyl, -aryl, -benzyl, -alkylamido, -alkylcarboxy, —C$_1$–C$_5$ alkylene-C(O)O—C$_1$–C$_5$ alkyl or —C$_1$–C$_5$ alkylene-OC(O)—C$_1$–C$_5$ alkyl groups; and
$Z_1$ and $Z_2$ are independently —H or —C$_1$–C$_{10}$ alkyl, which is unsubstituted or substituted with one or more of -halo, —OH or —N(Z$_3$)(Z$_4$), where $Z_3$ and $Z_4$ are independently, —H or —C$_1$–C$_5$ alkyl, which is unsubstituted or substituted with one or more of -halo, -hydroxy or —NH$_2$; or N, $Z_3$ and $Z_4$ are taken together to form an unsubstituted or substituted heterocyclic amine; or N, $Z_1$ and $Z_2$ are taken together to form a heterocyclic amine.

In one embodiment, A is —SO$_2$—.

In another embodiment, $R_1$, $R_2$, $R_3$, $R_4$, $R_7$, $R_8$, $R_9$ and $R_{10}$ are independently arylalkyl.

In illustrative embodiments $R^5$ and X in a compound of formula Ib are as set forth below:

| $R^5$ | X |
|---|---|
| O | —CH$_2$— |
| O | —CH(halo)— |
| O | —CH(OH)(CH$_2$)$_n$— |
| O | —CH(arylene)(OH)— |
| O | —O— |
| O | —NH— |
| O | —S— |
| O | —CH(NR$^{11}$R$^{12}$)— |

The invention also relates to compounds of Formula II:

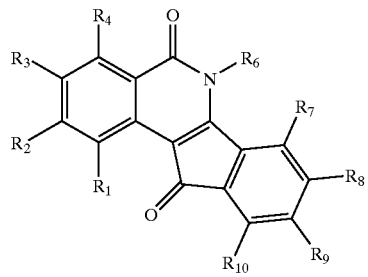

(II)

and pharmaceutically acceptable salts and hydrates thereof, wherein:

$R_6$ is —H or $C_1$–$C_4$ alkyl;
$R_1$, $R_2$, $R_3$, $R_4$, $R_7$, $R_8$, $R_9$ and $R_{10}$ are independently -hydrogen, -halo, -hydroxy, —O—(C$_1$–C$_5$ alkyl), —C$_1$–C$_{10}$ alkyl, -alkylhalo, —C$_2$–C$_{10}$ alkenyl, —C$_3$–C$_8$ carbocycle, -aryl, —NH$_2$, -alkylamino, —C(O)OH, —C(O)O(C$_1$–C$_5$ alkyl), —OC(O)(C$_1$–C$_5$ alkyl), NO$_2$ or -A-B; wherein at least one of $R^1$, $R^4$ and $R^{10}$ is other than hydrogen;
A is —SO$_2$—, —SO$_2$NH—, —NHCO—, —NHCONH—, —O—, —CO—, —OC(O)—, —C(O)O—, —CONH—, —CON(C$_1$–C$_4$ alkyl)-, —NH—, —CH$_2$—, —S— or —C(S)—;
B is —C$_1$–C$_{10}$ alkyl, —C$_2$–C$_{10}$ alkenyl, -heterocycle, —C$_3$–C$_8$ carbocycle, -aryl, —NH$_2$, -alkylamino, -aminodialkyl, -alkylheterocycle, -arylamido, —C(O)OH, —C(O)O—(C$_1$–C$_5$ alkyl), —C(O)O-phenyl or —NZ$_1$Z$_2$; and
$Z_1$ and $Z_2$ are independently —H or —C$_1$–C$_{10}$ alkyl, which is unsubstituted or substituted with one or more of -halo, —OH or —N(Z$_3$)(Z$_4$), where $Z_3$ and $Z_4$ are independently, —H or —C$_1$–C$_5$ alkyl, which is unsubstituted or substituted with one or more of -halo, -hydroxy or —NH$_2$; or N, $Z_3$ and $Z_4$ are taken together to form an unsubstituted or substituted heterocyclic amine; or N, $Z_1$ and $Z_2$ are taken together to form a heterocyclic amine.

In one embodiment, B is a heterocyclic amine.

In another embodiment, B is arylalkyl.

The invention also relates to compounds of Formula III:

(III)

and pharmaceutically acceptable salts and hydrates thereof, wherein:

X is —CH$_2$— or —O—;

R$_2$ and R$_3$ are independently -hydrogen, -halo, -alkylhalo, -hydroxy, —O—(C$_1$–C$_5$ alkyl), —C$_1$–C$_3$ alkyl, —NO$_2$, —NH$_2$, —CONH$_2$, —C(O)OH, —OC(O)—C$_1$–C$_5$ alkyl or —C(O)O—C$_1$–C$_5$ alkyl;

R$_8$ and R$_9$ are independently -hydrogen and -A-B;

A is —SO$_2$—, —SO$_2$NH— or —NHCO—; and

B is —C$_1$–C$_3$ alkyl, —NZ$_1$Z$_2$, -heterocycle or -alkylamino, each unsubstituted or substituted with one or more of -alkanol, -alkylamino, -aminoalkyl, -aminodialkyl or -heterocycle, each unsubstituted or substituted with —C$_1$–C$_{10}$ alkyl or -alkanol; and Z$_1$ and Z$_2$ are independently -hydrogen or —C$_1$–C$_8$ alkyl, which is unsubstituted or substituted with one or more of -hydroxy or —NZ$_3$Z$_4$, where Z$_3$ and Z$_4$ are independently —H or —C$_1$–C$_3$ alkyl, which is unsubstituted or substituted with one or more of -hydroxy or —NH$_2$, or N, Z$_3$ and Z$_4$ are taken together to a heterocyclic amine, or N, Z$_1$ and Z$_2$ are taken together to form a heterocyclic amine.

In one embodiment, —X— is —CH$_2$—.

In another embodiment, —X— is —O—.

In one embodiment, R$^8$ is hydrogen and R$^9$ is -A-B.

In another embodiment, R$^8$ is -A-B and R$^9$ is hydrogen.

In one embodiment, either R$^8$ is hydrogen and R$^9$ is -A-B, or R$^2$ is -A-B and R$^9$ is hydrogen.

In one embodiment, R$^3$, R$^8$ and R$^9$ are hydrogen and R$^2$ is -A-B, wherein A is —NHC(O)—.

In another embodiment, R$^2$, R$^8$ and R$^9$ are hydrogen and R$^3$ is -A-B, wherein A is —NHC(O)—.

In still another embodiment R$^2$, R$^3$ and R$^8$ are hydrogen and R$^9$ is -A-B, wherein A is —SO$_2$— or —SO$_2$NH—.

4.1 DEFINITIONS

"C$_1$–C$_3$ alkyl" refers to a straight or branched chain saturated hydrocarbon containing 1–3 carbon atoms. Examples of a C$_1$–C$_3$ alkyl group include, but are not limited to, methyl, ethyl, propyl and isopropyl "C$_1$–C$_4$ alkyl" refers to a straight or branched chain saturated hydrocarbon containing 1–4 carbon atoms. Examples of a C$_1$–C$_4$ alkyl group include, but are not limited to, methyl, ethyl, propyl, butyl, isopropyl, isobutyl, sec-butyl and tert-butyl.

"C$_1$–C$_5$ alkyl" refers to a straight or branched chain saturated hydrocarbon containing 1–4 carbon atoms. Examples of a C$_1$–C$_5$ alkyl group include, but are not limited to, methyl, ethyl, propyl, butyl, pentyl, isopropyl, isobutyl, sec-butyl and tert-butyl, isopentyl and neopentyl.

"C$_1$–C$_8$ alkyl" refers to a straight or branched chain saturated hydrocarbon containing 1–8 carbon atoms. Examples of a C$_1$–C$_8$ alkyl group include, but are not limited to, methyl, ethyl, propyl, butyl, pentyl, hexyl, heptyl, octyl, isopropyl, isobutyl, sec-butyl and tert-butyl, isopentyl, neopentyl, isohexyl, isoheptyl and isooctyl.

"C$_1$–C$_9$ alkyl" refers to a straight or branched chain saturated hydrocarbon containing 1–9 carbon atoms. Examples of a C$_1$–C$_9$ alkyl group include, but are not limited to, methyl, ethyl, propyl, butyl, pentyl, hexyl, heptyl, octyl, nonyl, isopropyl, isobutyl, sec-butyl and tert-butyl, isopentyl, neopentyl, isohexyl, isoheptyl, isooctyl and isononyl.

"C$_1$–C$_{10}$ alkyl" refers to a straight or branched chain saturated hydrocarbon containing 1–10 carbon atoms. Examples of a C$_1$–C$_{10}$ alkyl group include, but are not limited to, methyl, ethyl, propyl, butyl, pentyl, hexyl, heptyl, octyl, nonyl, decyl, isopropyl, isobutyl, sec-butyl and tert-butyl, isopentyl, neopentyl, isohexyl, isoheptyl, isooctyl, isononyl and isodecyl.

"C$_2$–C$_{10}$ alkenyl" refers to a straight or branched chain unsaturated hydrocarbon containing 2–10 carbon atoms and at least one double bond. Examples of a C$_2$–C$_{10}$ alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, 1-octene, 2-octene, 3-octene, 4-octene, 1-nonene, 2-nonene, 3-nonene, 4-nonene, 1-decene, 2-decene, 3-decene, 4-decene and 5-decene.

"C$_2$–C$_{10}$ alkynyl" refers to a straight or branched chain unsaturated hydrocarbon containing 2–10 carbon atoms and at least one triple bond. Examples of a C$_2$–C$_{10}$ alkynyl group include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne, isohexyne, 1-heptyne, 2-heptyne, 3-heptyne, 1-octyne, 2-octyne, 3-octyne, 4-octyne, 1-nonyne, 2-nonyne, 3-nonyne, 4-nonyne, 1-decyne, 2-decyne, 3-decyne, 4-decyne and 5-decyne.

"C$_1$–C$_4$ alkylene" refers to a C$_1$–C$_4$ alkyl group in which one of the C$_1$–C$_4$ alkyl group's hydrogen atoms has been replaced with a bond. Examples of a C$_1$–C$_4$ alkylene include —CH$_2$—, —CH$_2$ CH$_2$—, —CH$_2$CH$_2$CH$_2$— and —CH$_2$CH$_2$CH$_2$CH$_2$—.

"C$_1$–C$_5$ alkylene" refers to a C$_1$–C$_5$ alkyl group in which one of the C$_1$–C$_5$ alkyl group's hydrogen atoms has been replaced with a bond. Examples of a C$_1$–C$_4$ alkylene include —CH$_2$—, —CH$_2$ CH$_2$—, —CH$_2$CH$_2$CH$_2$— and -Examples of a C$_1$–C$_4$ alkylene include —CH$_2$—, —CH$_2$ CH$_2$—, —CH$_2$CH$_2$CH$_2$—, —CH$_2$CH$_2$CH$_2$CH$_2$— and —CH$_2$CH$_2$CH$_2$CH$_2$CH$_2$—.

"Alkylhalo" refers to a C$_1$–C$_5$ alkyl group, as defined above, wherein one or more of the C$_1$–C$_5$ alkyl group's hydrogen atoms has been replaced with —F, —Cl, —Br or —I. Representative examples of an alkylhalo group include, but are not limited to —CH$_2$F, —CCl$_3$, —CF$_3$, —CH$_2$Cl, —CH$_2$CH$_2$Br, —CH$_2$CH$_2$I, —CH$_2$CH$_2$CH$_2$F, —CH$_2$CH$_2$CH$_2$Cl, —CH$_2$CH$_2$CH$_2$CH$_2$Br, —CH$_2$CH$_2$CH$_2$CH$_2$I, —CH$_2$CH$_2$CH$_2$CH$_2$CH$_2$Br, —CH$_2$CH$_2$CH$_2$CH$_2$CH$_2$I, —CH$_2$CH(Br)CH$_3$, —CH$_2$CH(Cl)CH$_2$CH$_3$, —CH(F)CH$_2$CH$_3$ and —C(CH$_3$)$_2$(CH$_2$Cl).

"Alkylamino" refers to a C$_1$–C$_4$ alkyl group, as defined above, wherein one or more of the C$_1$–C$_4$ alkyl group's hydrogen atoms has been replaced with —NH$_2$. Representative examples of an alkylamino group include, but are not limited to —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH(NH$_2$)CH$_3$, —CH$_2$CH(NH$_2$)CH$_2$CH$_3$, —CH(NH$_2$)CH$_2$CH$_3$ and —C(CH$_3$)$_2$(CH$_2$NH$_2$).

"Aminoalkyl" refers to an —NH group, the nitrogen atom of said group being attached to a $C_1$–$C_4$ alkyl group, as defined above. Representative examples of an aminoalkyl group include, but are not limited to —NHCH$_3$, —NHCH$_2$CH$_3$, —NHCH$_2$CH$_2$CH$_3$, —NHCH$_2$CH$_2$CH$_2$CH$_3$—NHCH(CH$_3$)$_2$, —NHCH$_2$CH(CH$_3$)$_2$, —NHCH(CH$_3$)CH$_2$CH$_3$ and —NH—C(CH$_3$)$_3$.

"Aminodialkyl" refers to a nitrogen atom which has attached to it two $C_1$–$C_4$ alkyl groups, as defined above. Representative examples of a aminodialkyl group include, but are not limited to, —N(CH$_3$)$_2$, —N(CH$_2$CH$_3$)(CH$_3$), —N(CH$_2$CH$_3$)$_2$, —N(CH$_2$CH$_2$CH$_3$)$_2$, —N(CH$_2$CH$_2$CH$_2$CH$_3$)$_2$—N(CH(CH$_3$)$_2$)$_2$, —N(CH(CH$_3$)$_2$)(CH$_3$), —N(CH$_2$CH(CH$_3$)$_2$)$_2$, —NH(CH(CH$_3$)CH$_2$CH$_3$)$_2$, —N(C(CH$_3$)$_3$)$_2$ and —N(C(CH$_3$)$_3$)(CH$_3$).

"Aryl" refers to a phenyl or pyridyl group. Examples of an aryl group include, but are not limited to, phenyl, N-pyridyl, 2-pyridyl, 3-pyridyl and 4-pyridyl. An aryl group can be unsubstituted or substituted with one or more of the following groups: —$C_1$–$C_5$ alkyl, halo, -alkylhalo, hydroxy, —O—$C_1$–$C_5$ alkyl, —NH$_2$, -aminoalkyl, -aminodialkyl, —COOH, —C(O)O—($C_1$–$C_5$ alkyl), —OC(O)—($C_1$–$C_5$ alkyl), —N-amidoalkyl, —C(O)NH$_2$, -carboxamidoalkyl, or —NO$_2$.

"Arylalkyl" refers to an aryl group, as defined above, wherein one of the aryl group's hydrogen atoms has been replaced with a $C_1$–$C_5$ alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl, "Arylamido" refers to an aryl group, as defined above, wherein one of the aryl group's hydrogen atoms has been replaced with one or more —C(O)NH$_2$ groups. Representative examples of an arylamido group include 2–C(O)NH$_2$-phenyl, 3–C(O)NH$_2$-phenyl, 4–C(O)NH$_2$-phenyl, 2–C(O)NH$_2$-pyridyl, 3–C(O)NH$_2$-pyridyl and 4–C(O)NH$_2$-pyridyl, "Alkylheterocycle" refers to a $C_1$–$C_5$ alkyl group, as defined above, wherein one of the $C_1$–$C_5$ alkyl group's hydrogen atoms has been replaced with a heterocycle. Representative examples of an alkylheterocycle group include, but are not limited to, —CH$_2$CH$_2$-morpholine, —CH$_2$CH$_2$-piperidine, —CH$_2$CH$_2$CH$_2$-morpholine and —CH$_2$CH$_2$-imidazole.

"Alkylamido" refers to a $C_1$–$C_5$ alkyl group, as defined above, wherein one of the $C_1$–$C_5$ alkyl group's hydrogen atoms has been replaced with a —C(O)NH$_2$ group. Representative examples of an alkylamido group include, but are not limited to, —CH$_2$C(O)NH$_2$, —CH$_2$CH$_2$C(O)NH$_2$, —CH$_2$CH$_2$CH$_2$C(O)NH$_2$, —CH$_2$CH$_2$CH$_2$CH$_2$C(O)NH$_2$, —CH$_2$CH$_2$CH$_2$CH$_2$CH$_2$C(O)NH$_2$, —CH$_2$CH(C(O)NH$_2$)CH$_3$, —CH$_2$CH(C(O)NH$_2$)CH$_2$CH$_3$, —CH(C(O)NH$_2$)CH$_2$CH$_3$ and —C(CH$_3$)$_2$CH$_2$C(O)NH$_2$.

"Alkanol" refers to a $C_1$–$C_5$ alkyl group, as defined above, wherein one of the $C_1$–$C_5$ alkyl group's hydrogen atoms has been replaced with a hydroxyl group. Representative examples of an alkanol group include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH(OH)CH$_3$, —CH$_2$CH(OH)CH$_2$CH$_3$, —CH(OH)CH$_2$CH$_3$ and —C(CH$_3$)$_2$CH$_2$OH.

"Alkylcarboxy" refers to a $C_1$–$C_5$ alkyl group, as defined above, wherein one of the $C_1$–$C_5$ alkyl group's hydrogen atoms has been replaced with a —COOH group. Representative examples of an alkylcarboxy group include, but are not limited to, —CH$_2$COOH, —CH$_2$CH$_2$COOH, —CH$_2$CH$_2$CH$_2$COOH, —CH$_2$CH$_2$CH$_2$CH$_2$COOH, —CH$_2$CH(COOH)CH$_3$, —CH$_2$CH$_2$CH$_2$CH$_2$CH$_2$COOH, —CH$_2$CH(COOH)CH$_2$CH$_3$, —CH(COOH)CH$_2$CH$_3$ and —C(CH$_3$)$_2$CH$_2$COOH.

"N-amidoalkyl" refers to a —NHC(O)— group in which the carbonyl carbon atom of said group is attached to a $C_1$–$C_5$ alkyl group, as defined above. Representative examples of a N-amidoalkyl group include, but are not limited to, —NHC(O)CH$_3$, —NHC(O)CH$_2$CH$_3$, —NHC(O)CH$_2$CH$_2$CH$_3$, —NHC(O)CH$_2$CH$_2$CH$_2$CH$_3$, —NHC(O)CH$_2$CH$_2$CH$_2$CH$_2$CH$_3$, —NHC(O)CH(CH$_3$)$_2$, —NHC(O)CH$_2$CH(CH$_3$)$_2$, —NHC(O)CH(CH$_3$)CH$_2$CH$_3$, —NHC(O)—C(CH$_3$)$_3$ and —NHC(O)CH$_2$C(CH$_3$)$_3$.

"Carboxamidoalkyl" refers to a —C(O)NH— group in which the nitrogen atom of said group is attached to a $C_1$–$C_5$ alkyl group, as defined above. Representative examples of a carboxamidoalkyl group include, but are not limited to, —C(O)NHCH$_3$, —C(O)NHCH$_2$CH$_3$, —C(O)NHCH$_2$CH$_2$CH$_3$, —C(O)NHCH$_2$CH$_2$CH$_2$CH$_3$, —C(O)NHCH$_2$CH$_2$CH$_2$CH$_2$CH$_3$, —C(O)NHCH(CH$_3$)$_2$, —C(O)NHCH$_2$CH(CH$_3$)$_2$, —C(O)NHCH(CH$_3$)CH$_2$CH$_3$, —C(O)NH—C(CH$_3$)$_3$ and —C(O)NHCH$_2$C(CH$_3$)$_3$.

An "Arylene" group is a phenyl group in which one of the phenyl group's hydrogen atoms has been replaced with a bond. An arylene group may be in an ortho, meta, or para configuration and may be unsubstituted or independently substituted with one or more of the following groups: —$C_1$–$C_5$ alkyl, halo, -alkylhalo, hydroxy, —O—$C_1$–$C_5$ alkyl, —NH$_2$, -aminoalkyl, -aminodialkyl, —COOH, —C(O)O—($C_1$–$C_5$ alkyl), —OC(O)—($C_1$–$C_5$ alkyl), —N-amidoalkyl, —C(O)NH$_2$, -carboxamidoalkyl or —NO$_2$.

A "$C_3$–$C_8$ Carbocycle" is a non-aromatic, saturated hydrocarbon ring containing 3–8 carbon atoms. Representative examples of a $C_3$–$C_8$ carbocycle include, but are not limited to, cyclopropyl, cyclobutyl, cyclopentyl, cyclohexyl, cycloheptyl and cyclooctyl. A $C_3$–$C_8$ carbocycle may be unsubstituted or independently substituted with one or more of the following groups: —$C_1$–$C_5$ alkyl, halo, -alkylhalo, hydroxy, —O—$C_1$–$C_5$ alkyl, —NH$_2$, -aminoalkyl, -aminodialkyl, —COOH, —C(O)O—($C_1$–$C_5$ alkyl), —OC(O)—($C_1$–$C_5$ alkyl), —N-amidoalkyl, —C(O)NH$_2$, -carboxyamidoalkyl or —NO$_2$.

"Heterocycle" refers to a 5- to 10-membered aromatic or non-aromatic carbocycle in which 1–4 of the ring carbon atoms have been independently replaced with a N, O or S atom. Representative examples of a heterocycle group include, but are not limited to, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl. A heterocycle group may be unsubstituted or substituted with one or more of the following groups: —$C_1$–$C_5$ alkyl, halo, -alkylhalo, hydroxy, —O—$C_1$–$C_5$ alkyl, —NH$_2$, -aminoalkyl, -aminodialkyl, —COOH, —C(O)O—(C$_1$-C$_5$ alkyl), —OC(O)—(C$_1$-C$_5$ alkyl), —N-amidoalkyl, —C(O)NH$_2$, -carboxamidoalkyl or —NO$_2$.

A "Heterocyclic amine" is a heterocycle, defined above, having 1–4 ring nitrogen atoms. Representative examples of heterocyclic amines include, but are not limited to, piperidinyl, piperazinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, pyridinyl, oxazolyl, benzoxazolyl, thiazolyl, benzthiazolyl, pyrazolyl, triazolyl, benzodiazolyl, benzotriazolyl, pyrimidinyl, isoindolyl, indazolyl and morpholinyl; each of which may be unsubstituted or substituted with one or more of —N—(C$_1$-C$_5$ alkyl), —C(O)—(C$_1$-C$_5$ alkyl), —N—C(O)(C$_1$-C$_4$ alkyl), —O—(C$_1$-C$_5$ alkyl), -halo, -alkylhalo, -alkanol, -alkylamino, -hydroxy, —NO$_2$, —NH$_2$, -aminoalkyl, -aminodialkyl, -heterocyclic amine, —C$_1$-C$_{10}$ alkyl, —C$_2$-C$_{10}$ alkenyl, —C$_2$-C$_{10}$ alkynyl, -aryl, -benzyl, -alkylamido, -alkylcarboxy, —COOH, —C$_1$-C$_5$ alkylene-OC(O)—C$_1$-C$_5$ alkyl, —C$_1$-C$_5$ alkylene-C(O)O—C$_1$-C$_5$ alkyl, or a heterocycle or C$_3$-C$_8$ carbocycle which may be unsubstituted or substituted with one or more of —C$_1$-C$_{10}$ alkyl, —O—(C$_1$-C$_5$ alkyl), -halo, -alkylhalo, -alkanol, -alkylamino, -hydroxy, —NO$_2$ or —NH$_2$.

"Halo" is —F, —Cl, —Br or —I.

A "subject" is a mammal, e.g., a human, mouse, rat, guinea pig, dog, cat, horse, cow, pig, or non-human primate.

The invention also includes pharmaceutical compositions comprising an Indeno[1,2-c]isoquinoline Compound and a pharmaceutically acceptable carrier. The invention includes an Indeno[1,2-c]isoquinoline Compound when provided as a pharmaceutically acceptable prodrug, hydrated salt, such as a pharmaceutically acceptable salt, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

An "effective amount" when used in connection an Indeno[1,2-c]isoquinoline Compound is an amount effective for treating or preventing an inflammatory disease or a reperfusion disease.

The following abbreviations are used herein and have the indicated definitions: AcOH is acetic acid, CEP is Cecal Ligation and Puncture, DMEM is Dulbecco's Modified Eagle Medium, DMF is N,N-dimethylformamide, DMSO is dimethylsulfoxide, EtOAc is ethyl acetate, EtOH is ethanol, HEPES is 4-(2-hydroxyethyl)-1-piperazineethanesulfonic acid, LPS is lipopolysaccharide, MeOH is methanol, MS is mass spectrometry, NMR is nuclear magnetic resonance, PBS is phosphate-buffered saline (pH 7.4), PARS is poly (ADP-ribose)synthetase, Py is pyridine, SDS is dodecyl sulfate (sodium salt), STZ is streptozotocin, TCA is tricholoroacetic acid, TFA is trifluoroacetic acid, TLC is thin-layer chromatography, TNF is tumor necrosis factor and TRIS is Tris(hydroxymethyl)aminomethane.

Methods for Using Indeno[1,2-c]isoquinoline Compounds

The invention also includes methods for inhibiting PARS in a cell. PARS, which is also known as poly(ADP-ribose) synthetase, PARP ((poly(ADP-ribose) polymerase, EC 2.4.99) and ADP-ribosyltransferase (ADPRT, EC 2.4.2.30), is a nuclear enzyme that catalyzes a transfer of the ADP ribose moiety of NAD+ to an acceptor protein.

In one embodiment the method comprises contacting a cell with an Indeno[1,2-c]isoquinoline Compound in an amount sufficient to inhibit PARS in the cell. In general, any cell having, or capable of having, PARS activity or capable of expressing PARS can be used. The cell can be provided in any form. For example, the cell can be provided in vitro, ex vivo, or in vivo. PARS activity can be measured using any method known in the art, e.g., methods as described in Banasik et al., J. Biol. Chem. 267:1569–75 (1991). Illustrative examples of cells capable of expressing PARS include, but are not limited to muscle, bone, gum, nerve, brain, liver, kidney, pancreas, lung, heart, bladder, stomach, colon, rectal, small intestine, skin, esophageal, eye, larynx, uterine, ovarian, prostate, tendon, bone marrow, blood, lymph, testicular, vaginal and neoplastic cells.

Also provided in the invention is a method for inhibiting, preventing, or treating inflammation or an inflammatory disease in a subject. The inflammation can be associated with an inflammatory disease. Inflammatory diseases can arise where there is an inflammation of the body tissue. These include local inflammatory responses and systemic inflammation. Examples of such diseases include: organ transplant rejection; reoxygenation injury resulting from organ transplantation (see Grupp et al. J. Mol. Cell Cardiol. 31:297–303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, and chronic obstructive airway disease; inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis and viral or autoinimune encephalitis; autoimmune diseases including Type I and Type II diabetes mellitus; diabetic complications, including, but not limited to, diabetic cataract, glaucoma, retinopathy, nephropathy, such as microaluminuria and progressive diabetic nephropathy, polyneuropathy, gangrene of the feet, atherosclerotic coronary arterial disease, peripheral arterial disease, nonketotic hyperglycemic-hyperosmolar coma, mononeuropathies, autonomic neuropathy, foot ulcers, joint problems, and a skin or mucous membrane complication, such as an infection, a shin spot, a candidal infection or necrobiosis lipoidica diabeticorum; immune-complex vasculitis, systemic lupus erythematosus (SLE); inflammatory diseases of the heart such as cardiomyopathy, ischemic heart disease hypercholesterolemia, and atherosclerosis; as well as various other diseases that can have significant inflammatory components, including preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is adminstered as a treatment for cancer.

In one embodiment, a reoxygenation injury resulting from organ transplantation occurs during the organ transplantation.

The invention also includes methods for treating, preventing, or otherwise inhibiting reperfusion disease in a subject in need of treatment, prevention, or inhibition thereof. The method comprises administering an Indeno[1,2-c]isoquinoline Compound in an amount sufficient to treat, prevent or inhibit reperfusion disease in the subject. Reperfusion refers to the process whereby blood flow in the blood vessels is resumed following ischemia, such as occurs following constriction or obstruction of the vessel. Reperfusion disease can result following a naturally occurring episode, such as a myocardial infarction, stroke, or during a surgical procedure where blood flow in vessels is intentionally or unintentionally blocked.

In some embodiments, the subject is administered an effective amount of an Indeno[1,2-c]isoquinoline Compound.

The invention also includes pharmaceutical compositions useful for treating or preventing an inflammatory disease or a reperfusion disease, or for inhibiting PARS activity, or more than one of these activities. The compositions can be suitable for internal use and comprise an effective amount of an Indeno[1,2-c]isoquinoline Compound and a pharmaceutically acceptable carrier. The Indeno[1,2-c]isoquinoline Compounds are especially useful in that they demonstrate very low peripheral toxicity or, no peripheral toxicity.

The Indeno[1,2-c]isoquinoline Compounds can be administered in amounts that are sufficient to treat or prevent an inflammatory disease or a reperfusion disease and/or prevent the development thereof in subjects.

Administration of the Indeno[1,2-c]isoquinoline Compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, preferably in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising an Indeno[1,2-c]isoquinoline Compound and a pharmaceutically acceptable carrier, such as a) a diluent, e.g., lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone; if desired d) a disintegrant, e.g., starches, agar, methyl cellulose, bentonite, xanthan gum, algiic acid or its sodium salt, or effervescent mixtures; and/or e) absorbent, colorant, flavorant and sweetener.

Liquid, particularly injectable, compositions can, for example, be prepared by dissolution, dispersion, etc. For example, the Indeno[1,2-c]isoquinoline Compound is dissolved in or mixed with a pharmaceutically acceptable solvent such as, for example, water, saline, aqueous dextrose, glycerol, ethanol, and the like, to thereby form an injectable isotonic solution or suspension.

The Indeno[1,2-c]isoquinoline Compounds can be also formulated as a suppository that can be prepared from fatty emulsions or suspensions; using polyalkylene glycols such as propylene glycol, as the carrier.

The Indeno[1,2-c]isoquinoline Compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Indeno[1,2-c]isoquinoline Compounds can also be delivered by the use of monoclonal antibodies as individual carriers to which the Indeno[1,2-c]isoquinoline Compound molecules are coupled. The Indeno[1,2-c]isoquinoline Compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the Indeno[1,2-c]isoquinoline Compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

One embodiment for parenteral administration employs the implantation of a slow-release or sustained-released system, according to U.S. Pat. No. 3,710,795, incorporated herein by reference.

The compositions can be sterilized or contain non-toxic amounts of adjuvants, such as preserving, stabilizing, wetting or emulsifying agents, solution promoters, salts for regulating the osmotic pressure pH buffering agents, and other substances, including, but not limited to, sodium acetate or triethanolamine oleate. In addition, they can also contain other therapeutically valuable substances.

Compositions can be prepared according to conventional mixing, granulating or coating methods, respectively, and the present pharmaceutical compositions can contain from about 0.1% to about 99%, preferably from about 1% to about 70% of the Indeno[1,2-c]isoquinoline Compound by weight or volume.

The dosage regimen utilizing the Indeno[1,2-c] isoquinoline Compound is selected in accordance with a variety of factors including type, species, age, weight, sex and medical condition of the patient; the severity of the condition to be treated; the route of administration; the renal or hepatic function of the patient; and the particular Indeno [1,2-c]isoquinoline Compound employed. An physician or veterinarian of ordinary skill in the art can readily determine and prescribe the effective amount of the drug required to prevent, counter or arrest the progress of the condition.

Effective dosage amounts of the present invention, when used for the indicated effects, range from about 0.05 to about 1000 mg of Indeno[1,2-c]isoquinoline Compound per day. The compositions can contain about 0.5, 1.0, 2.5, 5.0, 10.0, 15.0, 25.0, 50.0, 100.0, 250.0, 500.0 or 1000.0 mg of Indeno[1,2-c]isoquinoline Compound. In one embodiment, the compositions are in the form of a tablet that can be scored. Effective plasma levels of the Indeno[1,2-c] isoquinoline Compounds can range from about 0.002 mg to about 50 mg per kg of body weight per day.

Indeno[1,2-c]isoquinoline Compounds can be administered in a single daily dose, or the total daily dosage may be administered in divided doses of two, three or four times daily. Furthermore, Indeno[1,2-c]isoquinoline Compounds can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of Indeno[1,2-c]isoquinoline Compound ranges from about 0.1% to about 15%, w/w or w/v.

Methods for Making Indeno[J, 2-c]isoquinoline Compounds

Examples of synthetic pathways useful for making Indeno [1,2-c]isoquinoline Compounds are set forth in the Examples, below and generalized in Schemes 1 and 2.

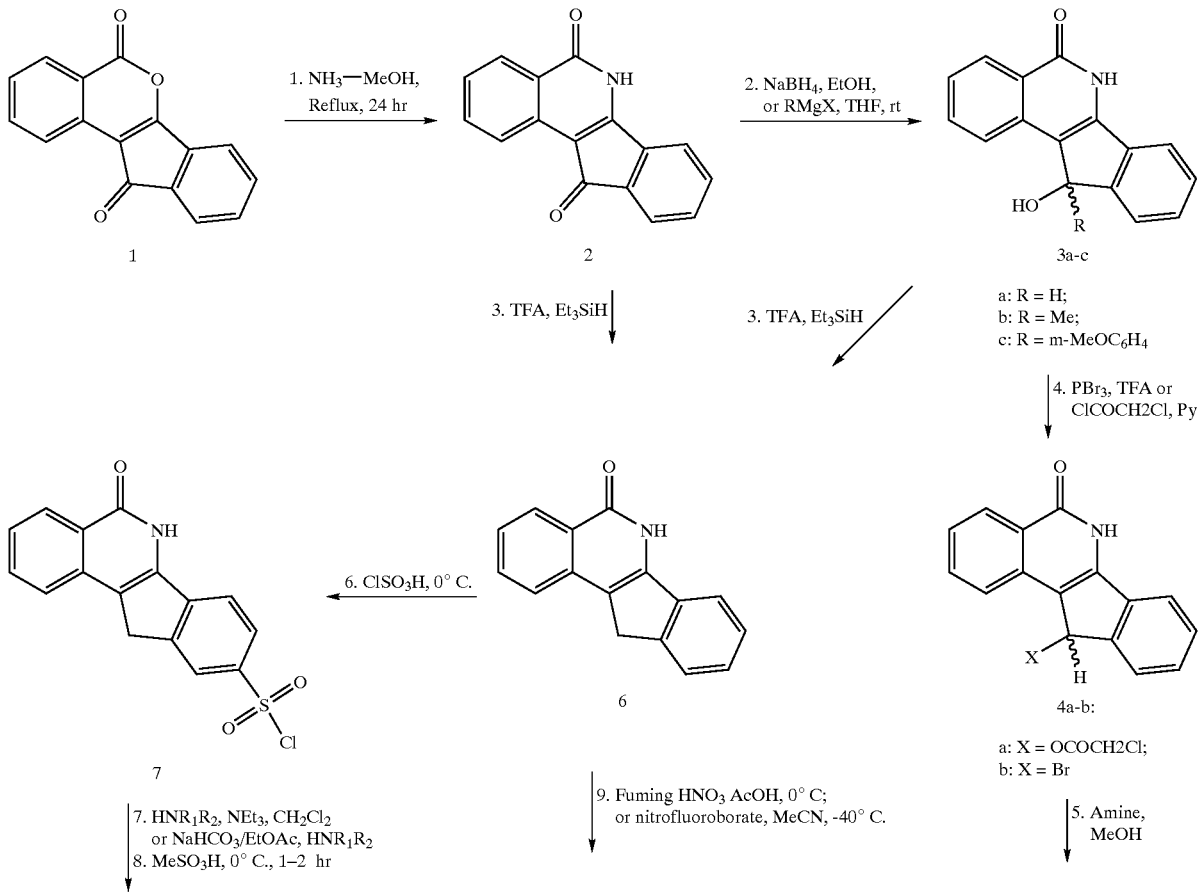

-continued

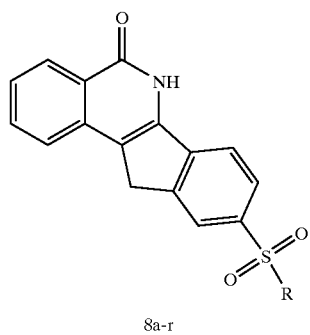

8a-r

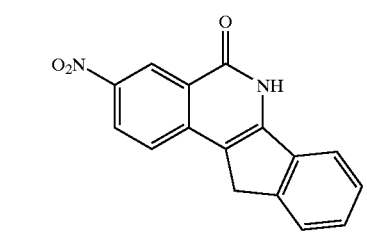

9

10. Ammonium formate, Pd-C, DMF
11. ClCOCH$_2$Cl, EtOAc, sat. NaHCO$_3$
12. NHR$_1$R$_2$, DMSO, rt

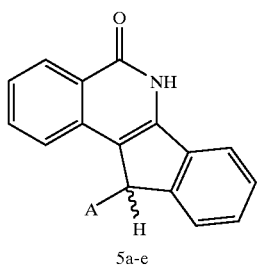

5a-e a: A = NMe$_2$
b: A = NEt$_2$
c: A = 4-Me-piperazine-1-yl
d: A = piperidine-1-yl
e: A = morpholine-4-yl a. R = 4-Methyl-piperazine-1-yl
b. R = 4-CH$_2$CO$_2$Me-piperazine-1-yl
c. R = 4-CH$_2$CH$_2$OH-piperazine-1-yl
d. R = imidazole-1-yl
e. R = L-prolinol
f. R = morpholine-4-yl
g. R = NHCH$_2$CH$_2$NMe$_2$
h. R = NHCH$_2$CH$_2$-piperidine-1-yl
i. R = NHCH$_2$CH$_2$N-(pyridine-2-yl)
j. R = NHCH$_2$CH$_2$-morpholine-4-yl
k. R = NHCH$_2$CH$_2$-(2-N-Me-tetrahydropyrrolidine-1-yl)
l. R = NHCH$_2$CH$_2$CH$_2$-morpholine-4-yl
m. R = NHCH$_2$CH$_2$CH$_2$-(tetrahydropyrrolidine-1-yl)
n. R = NHCH$_2$CH$_2$CH$_2$-imidazole-1-yl
o. R = NHCH$_2$CH$_2$CH$_2$-(4-methylpiperazine-1-yl)
p. R = N(CH$_2$CH$_2$Net$_2$)$_2$
q. R = N(CH$_2$CH$_2$NMe$_2$)$_2$
r. R = N(CH$_2$CH$_2$OH)$_2$

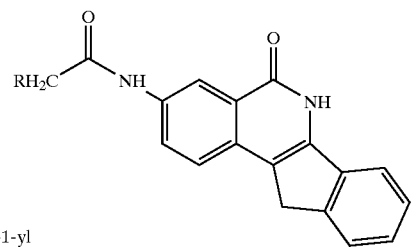

10a-b a. R = morpholine-4-yl
b. R = NMe$_2$

Scheme 2

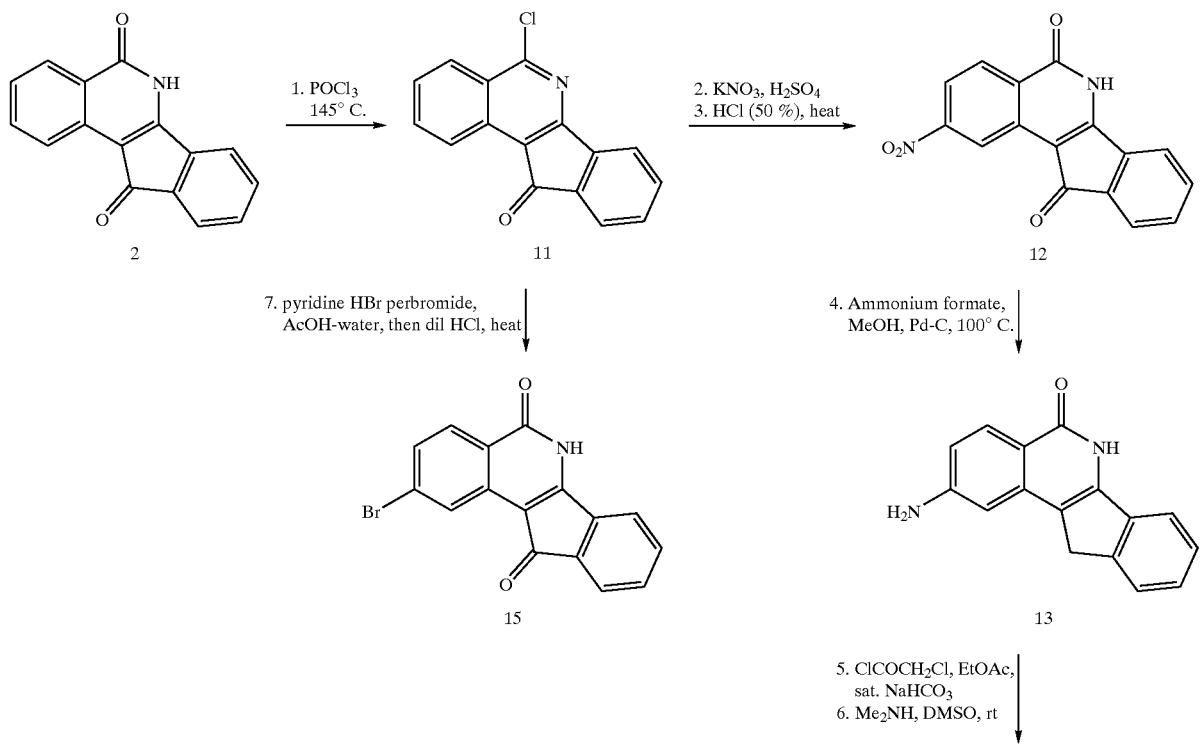

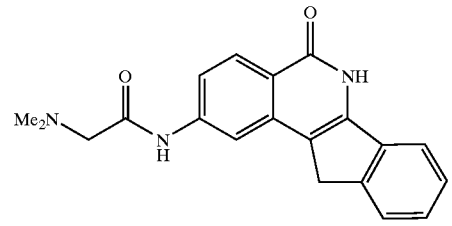

14

5,6-dihydro-5,11-diketo-11H-indeno[1,2-c]isoquinoline was prepared by reacting compound 1 (Aldrich Chemical, Milwaukee, Wis.) with ammonia in methanol.

(±) 11-hydroxy-5,6-dihydro-5-oxo-11H-indeno[1,2-c]isoquinoline (3a) was prepared by reacting 2 with NaBH$_4$ in ethanol.

(±) 11-hydroxy-11-methyl-5,6-dihydro-5-oxo-11H-indeno[1,2-c]isoquinoline (3b) was prepared by reacting 2 with MeMgI.

(±) 11-hydroxy-11-(m-methoxyphenyl)-5,6-dihydro-5-oxo-11H-indeno [1,2-c]isoquinoline (3c) was prepared from 2 using m-MeO—C$_6$H$_4$MgI.

(±) 11-N,N-dimethylamino-5,6-dihydro-5-oxo-1H-indeno [1,2-c]isoquinoline (5a) was prepared from 3a using chloroacetylchloride followed by reacting with dimethylamine. Similarly prepared are: (±) 11-N,N-diethylamino-5,6-dihydro-5-oxo-11H-indeno [1,2-c]isoquinoline (5b), (±) 11-N-(piperidino-1-yl)-5,6-dihydro-5-oxo-11H-indeno [1,2-c]isoquinoline (5d), (±) 11-N-(4-methylpiperazino-1-yl)-5,6-dihydro-5-oxo-11H-indeno[1,2-c]isoquinoline (5c), (±) 11-N-(morpholino-4-yl)-5,6-dihydro-5-oxo-11H-indeno[1,2-c]isoquinoline (5e). (+) 11-N-(morpholino-4-yl)-5,6-dihydro-5-oxo-11H-indeno[1,2-c]isoquinoline (5e) was also prepared from (±) 11-bromo-5,6-dihydro-5-oxo-11H-indeno [1, 2-c]isoquinoline (4b).

5,6-Dihydro-5-oxo-1H-indeno-[1,2-c]isoquinoline (6)is prepared by reduction of 5,6-dihydro-5,11-diketo-1H-indeno[1,2-c]isoquinoline (2) or (±) 11-hydroxy-5,6-dihydro-5-oxo-1H-indeno [1,2-c]isoquinoline (3a) using CF$_3$COOH/triethylsilane. 9-Chlorosulphonyl-5,6-dihydro-5-oxo-11H-indeno-[1,2-c]isoquinoline (7) was prepared by chlorosulfonation of 5,6-dihydro-5-oxo-1H-indeno-[1,2-c]isoquinoline (6). 9-[N-(4-methylpiperazine-1-yl)sulphonyl]-5,6-dihydro-5-oxo-11H-indeno-[1,2-c]isoquinoline (8a) was prepared from 9-chlorosulphonyl-5,6-dihydro-5-oxo-11H-indeno-[1,2-c]isoquinoline (7), and N-methylpiperazine. Similarly prepared are: 9-[N-(4-carbomethoxymethylenepiperazino-1-yl)sulphonyl]-5,6-dihydro-5-oxo-111H-indeno-[1,2-c]isoquinoline (8b), 9-[N-4-(2-hydroxyethylpiperazino-1-yl)-sulphonyl]-5,6-dihydro-5-oxo-11H-indeno-[1,2-c]isoquinoline (8c), 9-[N-(imidazolo-1-yl)sulphonyl]-5,6-dihydro-5-oxo-11H-indeno [1,2-c]isoquinoline (8d), 9-[N-(2-hydroxyprolinyl)sulphonyl]-5,6-dihydro-5-oxo-11H-indeno [1,2-c]isoquinoline (8e), 9-[N-morpholinesulphonyl]-5,6-dihydro-5-oxo-11H-indeno-[1,2-c]isoquinoline (8f), 9-[N-(2-[N,N-dimethylamino]ethyl)-aminosulphonyl]-5,6-dihydro-5-oxo-11H-indeno[1,2-c]isoquinoline (8 g), 9-[N-(2-[piperidino-1-yl]ethyl)-aminosulphonyl]-5,6-dihydro-5-oxo-11H-indeno [1,2-c]isoquinoline (8h), 9-[N-(2-(pyridino-2-yl)-ethyl)-aminosulphonyl]-5,6-dihydro-5-oxo-11H-indeno [1,2-c]isoquinoline (8I), 9-[N-(2-[morpholino-4-yl]ethyl)-aminosulphonyl]-5,6-dihydro-5-oxo-11H-indeno[1,2-c]isoquinoline (8j), 9-[N-(2-[N-methyltetrahydropyrrolidino-1-yl]ethyl) aminosulphonyl]-5,6-dihydro-5-oxo-11H-indeno-[1,2-c]isoquinoline (8k), 9-[N-(3-[morpholino-4-yl]propyl)-aminosulphonyl]-5,6-dihydro-5-oxo-11H-indeno-[1,2-c]isoquinoline (8l), 9-[N-(3-[tetrahydropyrrolodino-1-yl]propyl)aminosulphonyl]-5,6-dihydro-5-oxo-11H-indeno-[1,2-c]isoquinoline (8m), 9-[N-(3-[imidazolo-1-yl]propyl)-aminosulphonyl]-5,6-dihydro-5-oxo-11H-indeno-[1,2-c]isoquinoline (8n), 9-[N-[3-(4-methylpiperazino-1-yl]propyl)-aminosulphonyl]-5,6-dihydro-5-oxo-11H-indeno-[1,2-c]isoquinoline (8o),9-[N,N-di-(2-[N,N-diethylamino]ethyl)-aminosulphonyl]-5,6-dihydro-5-oxo-11H-indeno-[1,2-c]isoquinoline (8p), 9-[N,N-di-(2-[N,N-dimethylamino]ethyl)-aminosulphonyl]-5,6-dihydro-5-oxo-11H-indeno-[1,2-c]isoquinoline (8q), and 9-[N,N-di-(2-[N,N-dihydroxyethylamino]ethyl)-aminosulphonyl]-5,6-dihydro-5-oxo-11H-indeno-[1,2-c]isoquinoline (8r).

The amide derivatives 3-morpholin-4-yl-N-(5-oxo-5,11-dihydro-6H-indeno[1,2-c]isoquinolin-3-yl)-acetamide (10a), 3-dimethylamino-N-(5-oxo-5,11-dihydro-6H-indeno [1,2-c]isoquinolin-3-yl)-acetamide (10b) and 2-dimethylamino-N-(5-oxo-5,11-dihydro-6H-indeno[1,2-c]isoquinolin-2-yl)-acetamide (14) were prepared from 5,6-dihydro-5-oxo-11H-indeno[1,2-c]isoquinoline (6) and 5-chloro-11H-indeno[1,2-c]isoquinoline (11) using nitration, then reduction, and followed by amination of the chloroacetamide intermediate. 2-bromo-5,6-dihydro-5-oxo-11H-indeno[1,2-c]isoquinoline (15) was prepared by bromination of chloroamidate 11.

The invention is further described in the following examples, which do not limit the scope of the invention described in the claims. The following examples illustrate the synthesis of illustrative Indeno[1,2-c]isoquinoline Compounds of the invention, and demonstrates their usefulness for treating or preventing an inflammatory disease or reperfusion disease.

5. EXAMPLES

Example 1

Synthesis of Illustrative Indeno[1,2-c]isoquinoline Compounds a) General Methods Proton NMR spectra were obtained using a Varian 300 MHz spectrophotometer and chemical shift values (δ) are reported in parts per million (ppm). TLC was performed using TLC plates precoated with silica gel 60 F-254, and preparative TLC was performed using precoated Whatman 60A TLC plates. All intermediates and final compounds were characterized on the basis of $^1$H NMR and MS data.

b) Synthesis of 5,6-dihydro-5,11-diketo-11H-indeno[1,2-c]isoquinoline (2):

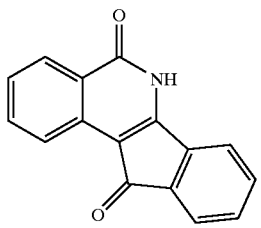

2

A stirred suspension of 1 (55 g, 0.22 mol) in NH$_3$/MeOH (7.0N, 700 mL) was refluxed 15 for 24 h. The reaction mixture was then allowed to cool to room temperature and was filtered and washed thoroughly with MeOH to provide 46 g of the orange colored above-titled product in 84% yield. $^1$H NMR (DMSO-D$_6$): δ 7.48–7.61 (m, 4H), 7.80–7.88 (m, 1H), 7.86 (d, J=8.7 Hz, 1H), 8.22 (d, J=8.4 Hz, 1H), 8.44 (d, J=7.5 Hz, 1H), 13.05 (s, 1H); $^{13}$C NMR (DMSO-D$_6$): δ 106.33, 121.63, 122.94, 123.27, 124.80, 128.45, 132.17, 133.60, 134.03, 134.68, 134.68, 134.81, 137.09, 156.41, 163.76, 190.57; MS (ES$^-$): m/z 246.2 (M−1); Anal. Calcd for C$_{16}$H$_9$NO$_2$: C, 77.72; H, 3.67; N, 5.67; Found: C, 77.54; H, 3.69, N, 5.69.

c) Synthesis of (±) 11-hydroxy-5,6-dihydro-5-oxo-11H-indeno[1,2-c]Isoquinoline (3a):

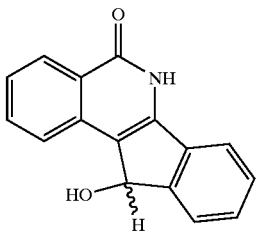

3a

To a stirred suspension of 2 (2.5 g, 0.01 mol) in EtOH (25 mL) was added NaBH$_4$ (3.75 g, 0.1 mol) at room temperature in small portions over 30 min. The reaction mixture was stirred for an additional 2 h and then cooled to 0° C. where it was triturated with dilute HCl (10% soln.). The resulting solid precipitated was filtered and washed with water and MeOH to provide 3a (2.326 g, 92%). $^1$H NMR (DMSO-D$_6$): δ 5.58 (d, J=8.1 Hz, 1H), 5.78 (d, J=8.7 Hz, 1H), 7.33–7.89 (m, 6H), 7.95 (d, J=7.8 Hz, 1W, 8.22 (d, J=7.8 Hz, 1H), 12.29 (s, 1H); $^3$C NMR (DMSO-D$_6$): δ 77.44, 118.81, 120.15, 124.28, 125.04, 125.67, 126.34, 128.46, 128.64, 128.95, 133.27, 135.62, 136.12, 139.93, 148.55, 163.69.; MS (ES$^+$): m/z 250.1 (M+1); Anal. Calcd for C$_{16}$H$_{11}$NO$_2$: C, 77.10; H, 4.45; N, 5.62. Found: C, 77.01; H, 4.57, N, 5.59.

Similarly, by reacting 2 with MeMgI and m-MeO—C$_6$H$_4$MgBr, respectively, compounds (±) 11-hydroxy-11-methyl-5,6-dihydro-5-oxo-11H-indeno[1,2-c]isoquinoline (3b) and (±) 11-hydroxy-11-(m-methoxyphenyl)-5,6-dihydros-5-oxo-11H-indeno[1,2-c]isoquinoline (3c) were prepared.

d) Synthesis of 11-Substituted 5,6-dihydro-5-oxo-11H-indeno[1,2-c]isoquinolines (5a-e):

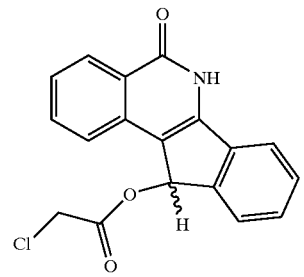

4a 5a-e

5a: R=NMe$_2$
5b: R=NEt$_2$
5c: R=-piperidine-1-yl
5d: R=—N-methyl-piperadin-4-yl
5e: R=-morpholin-1-yl To a stirred suspension of 3a (0.5 g, 0.002 mol) in pyridine (10 mL) was added chloroacetyl chloride (0.81 g, 0.006 mol) at 0° C. The reaction mixture was allowed to warm to room temperature and stir for 24 h. The reaction mixture was then poured on ice and extracted with EtOAc. The organic layer was separated, dried and concentrated to provide crude compound 4a, which was treated further with dimethylamine and stirred at room temperature for 24 h. The reaction mixture was poured on ice, and treated with 10% Hcl. The resulting mixture was then basified using saturated aqueous NaHCO$_3$ and the resulting solid was filtered to provide the desired product 5a. $^1$H NMR (DMSO-D$_6$): δ 2.31 (s, 6H), 5.00 (s, 1H), 7.28–7.45 (m, 3H), 7.68–7.73 (m, 2H), 7.95 (d, J=6.9 Hz, 1H), 8.10 (d, J=7.8 Hz, 1H), 8.21 (d, J=8.1 Hz, 1H), 12.26 (s, 1H); $^{13}$C NMR (DMSO-D$_6$): δ 68.09, 116.28, 120.52, 124.58, 125.74, 126.27, 126.34, 127.68, 128.64, 133.02, 136.27, 144.45, 163.80; MS (ES$^+$): m/z 277.2 (M+1).

The following compounds were also prepared by reacting 4a as above with diethylamine, piperidine, N-methylpiperidine and morpholine, respectively:

(±) 11-diethylamino-5,6-dihydro-5-oxo-11H-indeno[1,2-c]isoquinoline (5b)
(±) 11-piperidino-5,6-dihydro-5-oxo-11H-indeno [1,2-c]isoquinoline (5c)
(±) 11-(m-methylpiperazino)-5,6-dihydro-5-oxo-11H-indeno[1,2-c]isoquinoline (5d)
(±) 11-morpholino-5,6-dihydro-5-oxo-11H-indeno [1,2-c]isoquinoline (5e).

e) Synthesis of (±) 11-morpholino-5,6-dihydro-5-oxo-11H-indeno[1,2-c]isoquinolines (5e) from 4b

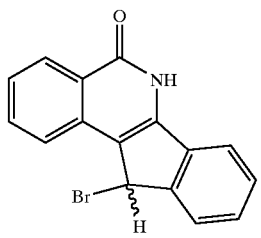

4b

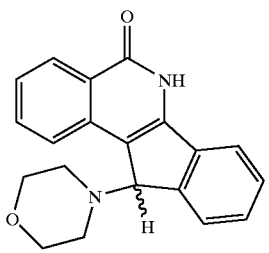

5e

To a stirred suspension of 3a (0.6 g, 2.4 mmol) in trifluoroacetic acid (5 mL) was added phosphorus tribromide (1.0 M soln. in $CH_2Cl_2$, 3 mL) at room temperature, and the reaction mixture was stirred for 8 h. The reaction mixture was poured on ice and the resulting solid was filtered to provide bromo compound 4b (0.61 gm, 76%). $^1$H NMR (DMSO-D$_6$): δ 7.35–7.50 (m, 3H), 7.61 (d, J=6.6 Hz, 1H), 7.73–7.82 (m, 2H), 7.94 (d, J=6.6 Hz, 1H), 8.23 (d, J=7.8 Hz, 1W, 12.41 (s, 1H); $^{13}$C NMR (DMSO-D$_6$): δ 52.06, 79.35, 114.43, 120.56, 123.58, 125.27, 125.50, 126.68, 128.55, 128.86, 129.66, 133.73, 135.91, 136.61, 141.39, 143.95, 163.74.

Compound 4b (0.5 g) was suspended in MeOH (10 mL) and treated with excess morpholine (~10 eq.) at room temperature and stirred at 60° C. for 3 h. The reaction mixture was poured on ice, and diluted with ethyl acetate (40 mL). The organic layer was separated and extracted in dil. HCl (10% soln.), the aqueous layer was then basified with sat. aq. NaHCO$_3$ and the resulting solid precipitated was filtered and dried to provide 5e (0.46 g, 90%). $^1$H NMR (DMSO-D$_6$): δ 2.56 (m, 4H), 3.49 (m, 4H), 5.04 (s, 1H), 7.31–7.45 (m, 3H), 7.65–7.76 (m, 2H), 7.96 (d, J=7.2 Hz, UH), 8.20–8.24 (m, 2H), 12.29 (s, 1H); $^{13}$C NMR (DMSO-D$_6$): δ 49.36, 67.62, 68.11, 115.20, 120.60, 124.47, 125.84, 126.34, 126.41, 127.76, 128.30, 128.72, 133.09, 136.30, 136.96, 140.35, 144.44, 163.67.

f) Synthesis of 5,6-dihydro-5-oxo-11H-indeno [1,2-c] Isoquinoline (6):

6

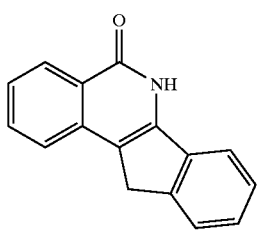

Method I: To a stirred solution of the alcohol 3a (0.35 g, 1.4 mmol) in trifluoroacetic acid (10 mL) was added at room temperature triethylsilane (0.812 g, 7 mmol) and the reaction mixture was stirred for 24 h. Trifluoroacetic acid was evaporated in vacuo and EtOAc was added to the resulting crude product. The resulting solid was filtered and washed with H$_2$O and EtOAc to provide the above-titled compound 6 (0.285 g, 87%). $^1$H NMR (DMSO-D$_6$): δ 3.89 (s, 2H), 7.30–7.47 (m, 3H), 7.59 (d, J=6.9 Hz, 1H), 7.72–7.74 (m, 2H), 7.98 (d, J=7.8 Hz, 1H), 8.23 (d, J=8.4 Hz, 1H), 12.31 (s, 1H); $^{13}$C NMR(DMSO-D$_6$): δ 33.51, 116.50, 120.19, 124.01, 125.51, 125.55, 126.42, 127.50, 127.68, 128.56, 133.45, 136.39, 137.53, 140.18, 143.80, 163.46; MS (ES$^-$): m/z 232.1 (M−1); Anal. Calcd for C$_{16}$H$_{11}$NO: C, 82.38; H, 4.75; N, 6.00. Found: C, 81.79; H, 4.45, N, 5.99.

Method II: To a stirred suspension of 2 (40 g, 0.16 mol) in trifluoroacetic acid (2.5 L) was added triethylsilane (94 g, 0.8 mol) in small portions at room temperature and the reaction mixture was stirred for 96 h, during which time the reaction progress was monitored using TLC (eluent −5% MeOH/CH$_2$Cl$_2$). The reaction mixture was slowly poured on ice, filtered, washed with copious amounts of H$_2$O and MeOH and dried in vacuo to provide the above-titled compound 6 (33.1 g, 88%), whose spectral data were identical to those of a sample of compound 6 that was obtained using Method I.

g) Synthesis of 9-chlorosulfonyl-5,6-dihydro-5-oxo-11H-indeno[1,2-c]Isoquinoline (7):

7

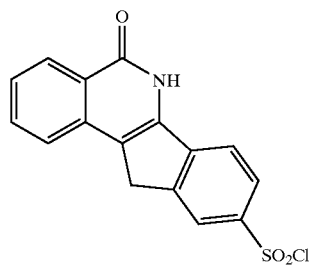

Compound 6 (40 g, 0.17 mol) was added in small portions to chlorosulfonyl chloride (112 mL, 1.71 mol) at 0°C. and the reaction mixture was allowed to warm to room temperature and stir for 2 h. The reaction mixture was slowly poured on ice and the resulting yellow solid was filtered, washed thoroughly with water and EtOAc and dried in vacuo to provide the above-titled product 7 (52 g, 92%). $^1$H NMR (DMSO-D$_6$): δ 3.91 (s, 2H), 7.43–7.48 (m, 1H), 7.60 (d, J=7.2 Hz, 1H), 7.74–7.76 (m, 2H), 7.79 (s, 1H), 7.90 (d, J=7.5 Hz, 1H), 8.23 (d, J=7.8 Hz, 1H), Anal. Calcd for C$_{16}$H$_{12}$ClNO$_4$S: C, 54.94; H, 3.46; N, 4.00. Found C, 55.28; H, 3.43, N, 3.68, Karl-Fisher, 2.95.

h) Synthesis of 9-sulphonamido Derivatives of 5,6-dihydro-5-oxo-11H-indeno[1,2-c]isoquinolines (8a–r) from 7:

8a–r

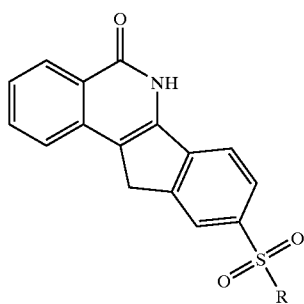

a. R=—N-(4-Methyl-piperazine-1-yl)
b. R=—N-(4-CH$_2$CO$_2$Me)-piperazine-1-yl
c. R=—N-(4-CH$_2$CH$_2$OH)-piperazine-1-yl d. R=—N-imidazole-1-yl
e. R=—N-L-prolinyl
f. R=—N-morpholin-4-yl
g. R=—NHCH$_2$CH$_2$NMe$_2$
h. R=—NHCH$_2$CH$_2$-piperidine-1-yl
i. R=—NHCH$_2$CH$_2$-(pyridine-2-yl)
j. R=—NHCH$_2$CH$_2$-morpholin-4-yl
k. R=—NHCH$_2$CH$_2$-(2-N-Me-tetrahydropyrrolidine-1-yl)
l. R=—NHCH$_2$CH$_2$CH$_2$-morpholin-4-yl
m. R=—NHCH$_2$CH$_2$CH$_2$-(tetrahydropyrrolidine-1-yl)
n. R=—NHCH$_2$CH$_2$CH$_2$-imidazole-1-yl
o. R=—NHCH$_2$CH$_2$CH$_2$-(4-methylpiperazine-1-yl)
p. R=—N(CH$_2$CH$_2$Net$_2$)$_2$
q. R=—N(CH$_2$CH$_2$NMe$_2$)$_2$
r. R=—N(CH$_2$CH$_2$OH)$_2$ Method I: To a stirred suspension of 3-(4-morpholino)-1-propylamine (17.28 g, 0.12 mol) in EtOAc was added sat. aq. NaHCO$_3$ (300 mL), and the mixture was allowed to stir for 15 min. Compound 7 (4.0 g, 0.012 mol) was then introduced in small portions at room temperature. The reaction mixture was stirred for 24 h; filtered and washed with H$_2$O, EtOAc and MeOH; refluxed in MeOH for 30 min; filtered while still warm; and washed with MeOH to provide the above-tited product 8l as a free base (2.330 g, 44%). $^1$H NMR(DMSO-D$_6$): δ 1.47–1.52 (m, 2H), 2.16–2.21 (m, 4H), 2.47–2.48 (m, 2H), 3.44–3.48 (m, 2H), 3.23 (m, 4H), 4.02 (s, 2H), 7.49–7.58 (m,1H), 7.78–7.82 (m, 3H), 7.97 (s, 1H), 8.14 (d, J=7.8 Hz, 1H), 8.26 (d, J=7.8 Hz,1H), 9.59 (s, 1H), 12.42 (s, 1H).

The free bases of 8d, 8g, 8h, 8j, 8l, 8m–8r were also prepared by Method I, but substituting 3-(4-morpholino)-1-propylamine with imidazole, 2-dimethylamino-ethylamine, 2-(N-piperidinyl)-ethylamine, 2-(N-morpholinyl)-ethylamine, 3-(N-morpholinyl)-propylamine, 3-(N-tetrahydropyrrolidinyl)-propylamine, 3-(N-imidazolyl)-propylamine, 3-(N-(4-methylpiperazinyl)-propylamine, di-(2-(diethylamino)-ethyl)amine, di-(2-(dimethylamino)-ethyl)amine and di-(2-hydroxyethyl)amine, respectively.
9-(N-sulphonylimidazole)-5,6-dihydro-5oxo-11H-indeno[1,2-c]isoquinolines (8a–r):

Method II: To a stirred suspension of 3-(4-morpholino)-1-propylamine (4.250 g) in CH$_2$Cl$_2$ (100 mL) was added 7 (1.950 g, 5.89 mmol) and the resulting mixture was stirred for 5 minutes. Subsequently, triethylamine (3 mL) was added and the reaction mixture was stirred for 24 hr at room temperature. After this time the precipitate was collected and washed with MeOH (2×100 mL) and the crude solid product transferred to a round bottom flask. This material was diluted with MeOH (200 mL), heated to reflux for 30 min. and filtered while still warm. The resulting filtercake was washed with MeOH (200 mL) to provide the desired product as the free base of 8l (1.460 g, 56%).

The free bases of compounds 8a–r were prepared using Method II, but substituting 3-(4-morpholino)-1-propylamine with imidazole, 2-dimethylamino-ethylamine, 2-(N-piperidinyl)-ethylamine, 2-(N-morpholinyl)-ethylamine, 3-(N-morpholinyl)-propylamine, 3-(N-tetrahydropyrrolidinyl)-propylamine, 3-(N-imidazolyl)-propylamine, 3-(N-(4-methylpiperazinyl)-propylamine, di-(2-(diethylamino)-ethyl)amine, di-(2-(dimethylamino)-ethyl)amine and di-(2-hydroxyethyl)amine, respectively.
i) General Procedure for the Preparation of Mesylate Salts of 8a–r:

Free base 8l was added to methanesulfonic acid at 0° C. and the resulting mixture was allowed to warm to room temperature and stir for 2 h. The reaction mixture was then poured into cold MeOH (between −10° C. and 0° C.) and the precipitated solid was filtered, washed with MeOH (100 mL) and dried in vacuo. The dried solid was then dissolved in water (~200 mL) and lyophilized to provide the methanesulfonate monohydrate salt 8l. (1.020 g, 84%). $^1$H NMR (DMSO-D$_6$): δ 1.75–1.85 (m, 2H), 2.35 (s, 3H), 2.78–2.84 (m, 2H), 2.96–3.12 (m, 4H), 3.36 (d, J=12.3 Hz, 2H), 3.61 (t, J=11.4 Hz, 2H), 3.94 (d, J=12.9 Hz, 2H), 4.03 (s, 2H), 7.49–7.55 (m, 1H), 7.76–7.84 (m, 3H), 7.99 (d, J=0.9 Hz, 1H), 8.15 (d, J=8.4 Hz, 1H), 8.25 (d, J=8.4 Hz, 1H), 9.59 (s, 1H), 12.42 (s, 1H); $^{13}$C NMR (DMSO-D$_6$): δ 24.27, 33.86, 51.89, 54.51, 64.02, 119.70, 120.39, 123.53, 126.09, 126.45, 128.63, 133.66, 135.80, 138.71, 141.21, 144.57, 163.29; Anal. Calcd for C$_{24}$H$_{31}$N$_3$O$_8$S$_2$: C, 52.06; H, 5.46; N, 7.59, Karl-Fisher, 3.36. Found: C, 51.85; H, 5.35, N, 7.30, Karl-Fisher, 4.32. Similarly, HCl, H$_2$SO$_4$, CH$_3$COOH, and succinic acid salts of 8l were prepared by substituting methanesulfonic acid with HCl, H$_2$SO$_4$ and CH$_3$COOH, respectively Example 2

Effect of Illustrative Indeno[1,2-c]isoquinoline Compounds on PARS Activity in Cultured Macrophages, Using a Whole-Cell Based Assay and a Purified Enzyme Assay.

Demonstration of illustrative Indeno[1,2-c]isoquinoline Compounds' ability to inhibit PARS and prevent peroxynitrite induced cytotoxicity was shown using methods described in Virag et al., *Br J Pharmacol.* 1999, 126(3) :769–77; and *Immunology* 1998, 94(3):345–55. RAW mouse macrophages were cultured in DMEM medium with high glucose and supplemented with 10% fetal bovine serum. Cells were used at 80% confluence in 12-well plates. Cells were pretreated with various concentrations (100 nM -1 μM) of an Indeno[1,2-c]isoquinoline Compound for 10 min. Peroxynitrite, a prototypical oxidant which induces DNA single strand breakage, was used to induce PARS activation. Peroxynitrite was diluted in phosphate buffered saline (PBS) (pH 11.0) and added to the cells in a bolus of 50 μl. Cells were then incubated for 20 min. Peroxynitrite was decomposed by incubation for 30 min at pH 7.0, used as a control, and failed to influence the parameter studied. After the 20 min incubation, the cells were spun, the medium was aspirated and the cells were resuspended in 0.5 ml assay buffer (56 mM HEPES pH 7.5, 28 mM KCl, 28 mM NaCl, 2 mM MgCl$_2$, 0.01% w/v digitonin and 0.125 μM NAD$^+$ and 0.5 μCi/ml $^3$H-NAD$^+$). Following an incubation in assay buffer, (10 min at 37° C.), PARS activity was measured as follows: 200 μl ice cold 50% w/v TCA was added and the samples were incubated for 4 hours at 4° C. Samples were then spun (10 min @10,000 g) and pellets washed twice with ice cold 5% w/v TCA and solubilized overnight in 250 μl 2% w/v SDS/0.1 N NaOH at 37° C. The contents of the tubes were added to 6.5 ml ScintiSafe Plus scintillation liquid (Fisher Scientific) and radioactivity was determined using a liquid scintillation counter (Wallac, Gaithersburg, Md.). The results shown in Table 1 demonstrate that the illustrative Indeno[1,2-c]isoquinoline Compounds significantly and dose-dependently inhibit the activation of PARS in the macrophage assay.

TABLE 1

Inhibitory effect of various novel substituted indeno[1,2-c]isoquinolines on PARS activation in cultured murine macrophages.

| Compound No. | % PARS inhibition at 1 μM | % PARS inhibition at 300 nM | % PARS inhibition at 100 nM |
|---|---|---|---|
| 2 | 60 | NT | 16 |
| 3a | 67 | NT | 8 |
| 3b | 25 | 0 | NT |
| 3c | 21 | 9 | NT |
| 4b | 88 | NT | 51 |
| 5a | 55 | NT | 10 |
| 5b | 33 | NT | 0 |
| 5c | 24 | NT | 0 |
| 5d | 48 | NT | 0 |
| 5e | 21 | NT | 0 |
| 6 | 65 | NT | 30 |
| 7 | 50 | NT | 0 |
| 8a | NT | 47 | NT |
| 8b | NT | NT | NT |
| 8c | NT | 27 | NT |
| 8d | NT | 82 | 77 |
| 8e | NT | 68 | NT |
| 8f | NT | NT | NT |
| 8g | NT | 55 | 34 |
| 8h | NT | 76 | 56 |
| 8j | NT | 76 | 34 |
| 8k | NT | 38 | 24 |
| 8l | NT | 84 | 34 |
| 8m | NT | 50 | NT |
| 8n | NT | 82 | 74 |
| 8o | NT | 55 | 48 |
| 8p | NT | 45 | 27 |
| 8q | NT | 28 | 20 |
| 8r | NT | 28 | 20 |
| 10a | NT | 59 | 55 |
| 10b | NT | 17 | 17 |

NT = Not tested

The potency of inhibition on purified PARS enzyme was subsequently determined for selected Indeno[1,2-c]isoquinoline Compounds, and the potency was compared with that of 3-aminobenzamide, a prototypical benchmark PARS inhibitor. The assay was performed in 96 well ELISA plates according to instructions provided with a commercially available PARS inhibition assay kit (Trevigen, Gaithersburg, Md.). Briefly, wells were coated with 1 mg/mL histone (50 μl/well) at 4° C. overnight. Plates were then washed four times with PBS and then blocked by adding 50 μl Strep-Diluent (supplied with the kit). After incubation (1 h, room temperature), the plates were washed four times with PBS. Appropriate dilutions of PARS inhibitors were combined with 2×PARS cocktail (1.95 mM NAD+, 50 μM biotinylated NAD+ in 50 mM TRIS pH 8.0, 25 mM MgCl$_2$) and high specific activity PARS enzyme (both were supplied with the kit) in a volume of 50 μl. The reaction was allowed to proceed for 30 min at room temperature. After 4 washes in PBS, incorporated biotin was detected by peroxidase-conjugated streptavidin (1:500 dilution) and TACS Sapphire substrate. The assay confirmed the results of the macrophage-based PARS assay. For example, the PARS inhibitor 8l exerted 50% inhibition of PARS activity in this assay at 3 nM, and thus was approximately 50,000 times more potent than the reference compound 3-aminobenzamide.

Example 3

Effects of Illustrative Indeno[1,2-c]isoquinoline Compounds in Various Models of Inflammatory Disease and Reperfusion Disease a: Effects of Illustrative Indeno[1,2-c]isoquinoline Compounds on in vitro Cell Disease Models In additional in vitro studies in isolated thymocytes, cells were exposed to peroxynitrite or hydrogen peroxide (toxic oxidant species) to induce cytotoxicity. In this system the toxicity is, at least in part, related to activation of the nuclear enzyme PARS. In this oxidant-stimulated thymocyte assay (described, in detail, in Virag et al., *Immunology* 94(3) :345–55, 1998), the compounds tested prevented the oxidant-induced suppression of the viability of the cells and did so at the low nanomolar concentration range. An example of this response (Compound 8l) is shown in Table 2. This assay represents an in vitro model of cells dying because of exposure to pro-oxidant species, as it occurs in during the reperfusion of ischemic organs.

TABLE 2

Reduction of peroxynitrite induced cytotoxicity by 30 nM – 3 μM of the Indeno [1,2-c] isoquinoline Compound 8l.

| | Control | +8l 30 nM | +8l 100 nM | +8l 300 nM | +8l 1 μM | +8l 3 μM |
|---|---|---|---|---|---|---|
| Cytotoxicity | 98% | 74% | 39% | 2% | 0% | 0% | b: Effect of Illustrative Indeno[1,2-c]isoquinoline Compounds on in vivo Models of Inflammatory Diseases In order to substantiate the efficacy of the compounds in inflammatory diseases, the effect of illustrative Indeno[1,2-c]isoquinoline Compounds was demonstrated in a systemic inflammatory model induced by bacterial lipopolysaccharide (LPS), which is reported to be responsible for causing reperfusion diseases and inflammatory diseases such as septic shock and systemic inflammatory response syndrome in animals (see Parrillo, *N. Engl. J. Med.*, 328:1471–1478 (1993) and Lamping, *J. Clin. Invest.* 101:2065–2071 (1998). In a series of experiments, mice were pretreated with intraperitoneal injection of 0.1 and 1 mg/kg of compounds 8l, 8p and 8j, and LPS at 10 mg/kg was injected i.p., and TNF-alpha was measured in the plasma at 90 minutes. As shown in Table 3, all compounds substantially reduced TNF production, indicative of the compounds' anti-inflammatory activity.

TABLE 3

Reduction of LPS induced TNF production by 0.1–1 mg/kg intraperitoneal injection of the PARS inhibitor compounds 8L, 8P and 8J in mice in vivo

| | 8j (0.1 mg/kg) | 8j (1.0 mg/kg) | 8p (0.1 mg/kg) | 8p (1.0 mg/kg) | 8l (0.1 mg/kg) | 8l (1.0 mg/kg) | Vehicle |
|---|---|---|---|---|---|---|---|
| TNF (ng/ml) | 3831.6 ± 385.2 | 5038.8 ± 377.1 | 4470.0 ± 184.4 | 5090.8 ± 203.7 | 3714.6 ± 300.9 | 3509.8 ± 311.5 | 6994.0 ± 904.4 |

All compounds markedly suppressed LPS induced TNF production when compared to control.

At high doses, LPS causes multiple organ dysfunction resembling of septic shock, and ultimately death (in part because of the early release of TNF-alpha). Similarly, in a model induced by cecal ligation and puncture (CLP), the live bacteria that derive from the intestinal flora induce systemic inflammation and shock. Agents that inhibit inflammatory mediator production, PARS activation, and cell death in this model prevent mortality induced by LPS or CLP. In experiments with Balb/c mice, injection of 100 mg/kg LPS intraperitoneally caused death in 50% of the animals over 24 h, whereas treatment of the animals with 3 mg/kg/day of compound 8l reduced the endotoxin-induced mortality to 10% under the same experimental conditions. In response to CLP induced shock, compound 8l (3 mg/kg/day) caused a reduction in the mortality from 100% death to 60% death over 24 hours.

The data demonstrating the reduction of TNF production by illustrative Indeno[1,2-c]isoquinoline Compounds in animals subjected to an inflammation model, coupled with the fact that TNF production is an important trigger of inflammation in various inflammatory diseases (such as, for example, colitis, arthritis and neuroinflammation and shock) indicate that the Indeno[1,2-c]isoquinoline Compounds have therapeutic effects in various systemic and local inflammatory diseases, including the rejection of transplanted organs, which entails both an inflammatory disease component and a reperfusion disease component and, accordingly, are useful for treating or preventing an inflammatory disease or a reperfusion disease.

c: Effect of Illustrative Indeno[1,2-c]isoquinoline Compounds on in vivo Models of Reperfusion Disease In order to substantiate the efficacy of the Indeno[1,2-c]isoquinoline Compounds in ischemia-reperfusion conditions, the effect of an illustrative Indeno[1,2-c]isoquinoline Compound in a mouse model of ischemic and reperfused gut was tested. The superior mesenteric artery was occluded for 45 min, followed by a reperfusion for 1 h. Following the end of the reperfusion, gut permeability was measured with the FD4 method in evened gut sacks (Liaudet et al; *Shock* 2000, 14(2): 134–41). Ischemia-reperfusion increased the permeability of the gut from 11±4 to 216±27 ml/min/cm$^2$, indicative of severe damage of the reperfused gut. Treatment with Compound 8l (3 mg/kg i.v., injected 10 min. prior to initiation of reperfusion) reduced the increase in the permeability of the gut by approximately 73%, indicating a marked maintenance of the gut function. The ischemia-reperfusion studies in the gut were associated with a 80% mortality over 12 hours, whereas only 15% mortality was noted in the animals treated with 8l.

In another set of experiments, the effect of Compound 8l in a rat model of middle cerebral artery occlusion/reperfusion was assayed as described in Abdelkarim et al., *Int J Mol Med.* 2001, 7(3):255–60. Occlusion lasted for 2 hours, followed by reperfusion for 24 hours. Infarct size was quantified with tetrazolium staining. Compound 8l was administered at 3 mg/kg/day in 3 divided intraperitoneally injected doses, the first dose being administered 10 min. prior to the initiation of reperfusion. There was an approximately 80% reduction in the degree of cortical necrosis and neuronal death in the animals administered with 8l, when compared to vehicle-treated controls. This protection also translated into functional benefit, such as neurological improvements in the PARS inhibitor treated group.

These data indicate that the Indeno[1,2-c]isoquinoline Compounds have therapeutic effects in various systemic and local conditions of reperfusion diseases, including the rejection of transplanted organs, which entails both an inflammatory disease component and a reperfusion disease component and, accordingly, are useful for treating or preventing an inflammatory disease or a reperfusion disease.

d: Effect of Illustrative Indeno[1,2-c]isoquinoline Compounds in a Diabetes Model PARS inhibitors and PARS deficiency are known to reduce the development of diabetes and the incidence of diabetic complications (Mabley et al., *Br J. Pharmacol.* 2001, 133(6):909–9; and Soriano et al., *Nat Med.* 2001, 7(1):108–13). In order to substantiate the efficacy of the Indeno[1,2-c]isoquinoline Compounds in a diabetes model, a single high-dose streptozotocin model of diabetes was conducted as previously described. Briefly, 160 mg/kg streptozotocin was injected to mice treated with vehicle or with illustrative Indeno[1,2-c]isoquinoline Compounds intraperitoneally (3 mg/kg) and 3 days later blood sugar levels were determined using a blood glucose meter. The data shown in Table 4 demonstrate that the illustrative Indeno[1,2-c]isoquinoline Compounds attenuate the streptozotocin-induced onset of diabetes as they reduce the hyperglycemia.

TABLE 4

Reduction of streptozotocin (STZ) induced hyperglycemia by 3 mg/kg intraperitoneal injection of the PARS inhibitor compounds 8l, 8p and 8j in mice in vivo

|  | Basal | STZ + Vehicle | STZ + 8j | STZ + 8p | 8l |
|---|---|---|---|---|---|
| Glucose (mg/ml) | 153 ± 21 | 320 ± 13 | 253 ± 24 | 264 ± 24 | 244 ± 21 |

Accordingly, the Indeno[1,2-c]isoquinoline Compounds are useful for treating or preventing diabetes or a diabetic complication.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparant to those skilled in the art and are intended to fall within the scope of the appended claims.

A number of references have been cited, the entire disclosures of which have been incorporated herein in their entirety.

What is claimed is:

1. A compound of the formula

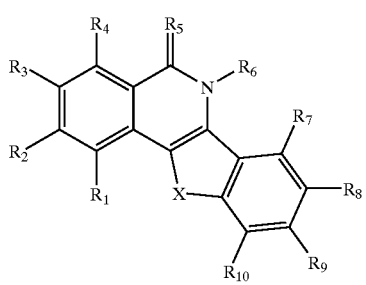

(Ia)

or a pharmaceutically acceptable hydrate or salt thereof, wherein:

$R_5$ is NH;

$R_6$ is —H or $C_1$–$C_4$ alkyl;

X is —C(O)—, —CH$_2$—, —CH(halo)-, —CH(OH)(CH$_2$)$_n$—, —CH(OH)-arylene-, —O—, —NH—, —S— or —CH(NR$_{11}$R$_{12}$)—, wherein n is an integer ranging from 0–5;

$R_{11}$ and $R_{12}$ are independently -hydrogen or —$C_1$—$C_9$ alkyl, or N, $R_{11}$ and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$ and $R_{10}$ are independently -hydrogen, -halo, -hydroxy, —O—($C_1$-$C_5$ alkyl), —$C_1$–$C_{10}$ alkyl, -alkylhalo, —$C_2$–$C_{10}$ alkenyl, —$C_3$–$C_8$ carbocycle, -aryl, —NH$_2$, -alkylamino, —C(O)OH, —C(O)O($C_1$-$C_5$ alkyl), —OC(O)($C_1$-$C_5$ alkyl), NO$_2$ or -A-B;

wherein A is —SO$_2$—, —SO$_2$NH—, —NHCO—, —NHCONH—, —O—, —CO—, —OC(O)—, —C(O)O—, —CONH—, —CON($C_1$-$C_4$ alkyl)-, —NH—, —CH$_2$—, —S— or —C(S)—;

B is —$C_1$–$C_{10}$ alkyl, —$C_2$–$C_{10}$ alkenyl, -heterocycle, —$C_3$–$C_8$ carbocycle, -aryl, —NZ$_1$Z$_2$, -alkylamino, -aminodialkyl, -arylamido, —C(O)OH, —C(O)O—($C_1$-$C_5$ alkyl), —C(O)O-phenyl, a 5–10 membered aromatic or non-aromatic carbocycle in which 1–4 of the ring carbon atoms are independently replaced with a N, O or S atom, or B is a $C_1$-$C_5$ alkyl group in which one of the $C_1$-$C_5$ alkyl group's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O—($C_1$-$C_5$ alkyl), -halo, -alkyihalo, -alkanol, -alkylamino, -hydroxy, —NO$_2$, —NH$_2$, -aminoalkyl, -aminodialkyl, —$C_1$-$C_{10}$ alkyl, —$C_2$-$C_{10}$ alkenyl, —$C_2$-$C_{10}$ alkynyl, -aryl, -benzyl, -alkylamido, -alkylcarboxy, —$C_1$-$C_5$ alkylene-C(O)O—$C_1$-$C_5$ alkyl, $C_1$-$C_5$ alkylene-OC(O)-$C_1$-$C_5$ alkyl or a 5–10 membered aromatic or non-aromatic carbocycle in which 1–4 ring carbon atoms are independently replaced with a N, O or S atom, at least one of which is a nitrogen atom; and $Z_1$ and $Z_2$ are independently —H or —$C_1$-$C_{10}$ alkyl, which is unsubstituted or substituted with one or more of -halo, —OH or —N($Z_3$)($Z_4$), where $Z_3$ and $Z_4$ are independently, —H or —$C_1$-$C_5$ alkyl, which is unsubstituted or substituted with one or more of -halo, -hydroxy or —NH$_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom.

2. A compound of the formula

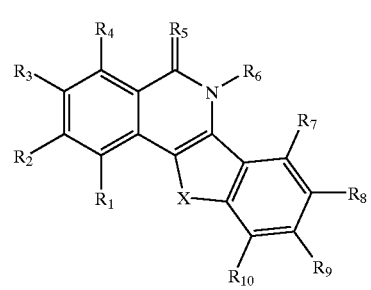

(Ib)

or a pharmaceutically acceptable hydrate or salt thereof, wherein:

$R_5$ is O;

$R_6$ is —H or $C_1$-$C_4$ alkyl;

X is —OH$_2$—, —CH(halo)-, —CH(OH)(CH$_2$)$_n$—, —CH(OH)-arylene-, —NH—, —S— or —CH(NR$_{11}$R$_{12}$)—, wherein n is an integer ranging from 0–5;

$R_{11}$ and $R_{12}$ are independently -hydrogen or —$C_1$—$C_9$ alkyl, or N, $R_{11}$, and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$ and $R_{10}$ are independently -hydrogen, -halo, -hydroxy, —O—($C_1$-$C_5$ alkyl), —$C_1$–$C_{10}$ alkyl, -alkylhalo, —$C_2$–$C_{10}$ alkenyl, —$C_3$–$C_8$ carbocycle, -aryl, —NH$_2$, -alkylamino, —C(O)OH, —C(O)O($C_1$-$C_5$ alkyl), —OC(O)($C_1$-$C_5$ alkyl), NO$_2$ or -A-B; with the proviso that when X represents CH2, R1, R2, R3, R4, R7, R8, R9 and R10 do not represent hydrogen simultaneously;

wherein A is —SO$_2$—, —SO$_2$NH—, —NHCO—, —NHCONH—, —O—, —CO—, —OC(O)—, —C(O)O—, —CONH—, —CON($C_1$-$C_4$ alkyl)-, —NH—, —CH$_2$—, —S— or —C(S)—;

B is —$C_1$-$C_{10}$ alkyl, —$C_2$-$C_{10}$ alkenyl, —$C_3$-$C_8$ carbocycle, -aryl, —NZ$_1$Z$_2$, -alkylamino, -aminodiallcyl, -arylamido, —C(O)OH, —C(O)O—($C_1$-$C_5$ alkyl), —C(O)O-phenyl, a 5–10 membered aromatic or non-aromatic carbocycle in which 1–4 of the ring carbon atoms are independently replaced with a N, O or S atom, or B is a $C_1$-$C_5$ alkyl group in which one of the $C_1$-$C_5$ alkyl aroup's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O—($C_1$-$C_5$ alkyl), -halo, -alkyihalo, -alkanol, -alkylamino, -hydroxy, —NO$_2$, —NH$_2$, -aminoalkyl, -aminodialkyl, —$C_1$-$C_{10}$ alkyl, —$C_2$-$C_{10}$ alkenyl, -aryl, -benzyl, -alkylamido, -alkylcarboxy, —$C_1$–$C_5$ alkylene-C(O)O—$C_1$–$C_5$ alkyl, $C_1$–$C_5$ alkylene-OC(O)—$C_1$–$C_5$ alkyl or a 5–10 membered aromatic or non-aromatic carbocycle in which 1–4 ring carbon atoms are independently replaced with a N, O or S atom, at least one of which is a nitrogen atom; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom.

3. A compound of the formula

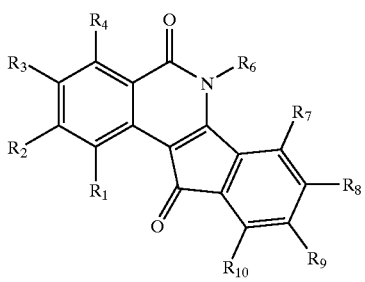

(II)

or a pharmaceutically acceptable hydrate or salt thereof, wherein:

$R_4$ is —H;

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), $NO_2$ or -A-B; wherein at least one of $R^1$, $R^4$ and $R^{10}$ is other than hydrogen;

A is —$SO_2$—, —$SO_2NH$—, —NHCO—, —NHCONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, —$C_3$–$C_8$ carbocycle, -aryl, $NH_2$, -alkylamino, -aminodialkyl, -arylamido, —C(O)OH, —C(O)O—($C_1$–$C_5$ alkyl), —C(O)O-phenyl, —$NZ_1Z_2$, a 5–10 membered aromatic or non-aromatic carbocycle in which 1–4 of the ring carbon atoms are independently replaced with a N, O or S atom, or B is a $C_1$–$C_5$ alkyl group in which one of the $C_1$–$C_5$ alkyl group's hydrogen atoms is replaced with a 5–10 membered aromatic or non-aromatic carbocycle in which 1–4 of the carbocycle's ring carbon atoms are independently replaced with a N, O or S atom; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom.

4. The compound of claim 2 wherein $R_6$ is hydrogen.

5. The compound of claim 1 wherein $R_1$, $R_2$, $R_3$, $R_4$, $R_7$, $R_8$, $R_9$, and $R_{10}$ are independently hydrogen, methyl, ethyl, halo, —$NO_2$, hydroxy, methoxy, ethoxy, —$NH_2$, -aminoalkyl, -aminodialkyl or -A-B.

6. The compound of claim 5, wherein either $R_8$ or $R_9$, but not both, is -A-B.

7. The compound of claim 6 wherein $R_1$, $R_2$, $R_3$, $R_4$, $R_7$, and $R_{10}$ are hydrogen.

8. The compound of claim 1, wherein $R_9$ is -A-B.

9. The compound of claim 5, wherein $R_9$ is -A-B.

10. The compound of claim 7, wherein $R_9$ is -A-B and $R_8$ is hydrogen.

11. The compound of claim 6, wherein A is —$SO_2$—, —$SO_2NH$— or —NHCO—.

12. The compound of claim 7, wherein A is —$SO_2$—, —$SO_2NH$— or —NHCO—.

13. The compound of claim 8, wherein A is —$SO_2$—, —$SO_2NH$— or —NHCO—.

14. The compound of claim 9, wherein A is —$SO_2$—, —$SO_2NH$— or —NHCO—.

15. The compound of claim 10, wherein A is —$SO_2$—, —$SO_2NH$— or —NHCO—.

16. The compound of claim 1, wherein $R_9$ is -A-B and B is —$C_1$–$C_8$ alkyl, —$C_3$14 $C_8$ carbocycle, -aryl, -alkylamino, -alkanol, a 5–10 membered aromatic or non-aromatic carbocycle in which 1–4 of the ring carbon atoms are independently replaced with a N, O or S atom, or B is a $C_1$–$C_5$ alkyl group in which one of the $C_1$–$C_5$ alkyl group's hydrogen atoms is replaced with a 5–10 membered aromatic or non-aromatic carbocycle in which 1–4 of the carbocycle's ring carbon atoms are independently replaced with a N, O or S atom.

17. The compound of claim 16, wherein B is —$C_1$–$C_5$ alkyl.

18. The compound of claim 5, wherein A is —$SO_2$— and B is —$NZ_1Z_2$, and $Z_1$ and $Z_2$ are independently hydrogen, or —$C_1$–$C_5$ alkyl, unsubstituted or substituted with -halo, -hydroxy or —$NZ_3Z_4$; wherein $Z_3$ and $Z_4$ are independently -hydrogen, —$C_1$–$C_5$ alkyl, unsubstituted or substituted with one or more of -halo, -hydroxy or —$NH_2$, or wherein N, $Z_1$ and $Z_2$, taken together, form a 5–10 membered aromatic or non-aromatic carbocycle in which 1–4 ring carbon atoms are independently replaced with a N, O or S atom, at least one of which is a nitrogen atom.

19. The compound of claim 18, wherein $Z_1$ and $Z_2$ are wherein n is an integer ranging from 1–5, and D is hydrogen, hydroxy, a 5–10 membered aromatic or non-aromatic carbocycle in which 1–4 ring carbon atoms are independently replaced with a N, O or S atom, at least one of which is a nitrogen atom, or —$NZ_3Z_4$; wherein $Z_3$ and $Z_4$ are independently hydrogen, methyl or ethyl.

20. The compound of claim 18, wherein B is a 5–10 membered aromatic or non-aromatic carbocycle in which 1–4 of the ring carbon atoms are independently replaced with a N, O or S atom, the carbocycle being unsubstituted or substituted with one or more of methyl, ethyl, or -alkanol.

21. The compound of claim 18, wherein $Z_1$ is hydrogen and $Z_2$ is —$NZ_3Z_4$ wherein n is an integer ranging from 1–5, and $Z_3$ and $Z_4$ are independently methyl or ethyl, or, taken together, $NZ_3Z_4$ forms a 5–10 membered aromatic or non-aromatic carbocycle in which 1–4 ring carbon atoms are independently replaced with a N, O or S atom, at least one of which is a nitrogen atom.

22. The compound of claim 15, wherein X is —$CH_2$—, A is —$SO_2$— and B is —$NZ_1Z_2$; wherein $Z_1$ and $Z_2$ are independently hydrogen, —$C_1$-$C_5$ alkyl unsubstituted or substituted with halo, hydroxy or —$NZ_3Z_4$; wherein $Z_3$ and $Z_4$ are independently hydrogen, —$C_1$-$C_5$ alkyl, unsubstituted or substituted with halo, hydroxy or —$NH_2$; or wherein $Z_1$ and $Z_2$, taken together, form a 5–10 membered aromatic or non-aromatic carbocycle in which 1–4 ring carbon atoms are independently replaced with a N, O or S atom, at least one of which is a nitrogen atom.

23. The compound of claim 22, wherein $Z_1$ and $Z_2$ are wherein n is an integer ranging from 1–5, and D is hydrogen, hydroxy, —$NZ_3Z_4$, or a 5–10 membered aromatic or non-aromatic carbocycle in which 1–4 ring carbon atoms are independently replaced with a N, O or S atom, at least one of which is a nitrogen atom; wherein $Z_3$ and $Z_4$ are independently hydrogen, methyl or ethyl.

24. The compound of claim 18, wherein B is a 5–10 membered aromatic or non-aromatic carbocycle in which 1–4 of the ring carbon atoms are independently replaced with a N, O or S atom, the carbocycle being unsubstituted or substituted with one or more of methyl, ethyl, or -alkanol.

25. The compound of claim 18, wherein $Z_1$ is hydrogen and $Z_2$ is —$(CH_2)_n$—$NZ_3Z_4$, wherein n is 2 or 3, and $Z_3$ and $Z_4$ are independently methyl or ethyl, or, taken together, $NZ_3Z_4$ form a 5–10 membered aromatic or non-aromatic carbocycle in which 1–4 ring carbon atoms are independently replaced with a N, O or S atom, at least one of which is a nitrogen atom.

26. The compound of claim 1 wherein X is —C(O)—, —CH(OH)—, —CH(Br)—, —$CH_2$— or —CH($NR_{11}R_{12}$)— wherein $R_{11}$ and $R_{12}$ are hydrogen, —$C_1$-$C_9$ alkyl, or $NR_{11}R_{12}$, taken together, form a 5–10 membered aromatic or non-aromatic carbocycle in which one ring carbon atom is replaced with a nitrogen atom and up to 3 of the remaining ring carbon atoms are independently replaced with a N, O or S atom.

27. The compound of claim 6 wherein X is —C(O)—, —CH(OH)—, —CH(Br)—, —$CH_2$— or —CH($NR_{11}R_{12}$)— wherein $R_{11}$ and $R_{12}$ are hydrogen, —$C_1$-$C_9$ alkyl, or $NR_{11}R_{12}$, taken together, form a 5–10 membered aromatic or non-aromatic carbocycle in which one ring carbon atom is replaced with a nitrogen atom and up to 3 of the remaining ring carbon atoms are independently replaced with a N, O or S atom.

28. The compound of claim 8 wherein X is —C(O)—, —CH(OH)—, —CH(Br)—, —$CH_2$— or —CH($NR_{11}R_{12}$)— wherein $R_{11}$ and $R_{12}$ are hydrogen, —$C_1$-$C_9$ alkyl, or $NR_{11}R_{12}$, taken together, form a 5–10 membered aromatic or non-aromatic carbocycle in which one ring carbon atom is replaced with a nitrogen atom and up to 3 of the remaining ring carbon atoms are independently replaced with a N, O or S atom.

29. The compound of claim 9 wherein X is —C(O)—, —CH(OH)—, —CH(Br)—, —$CH_2$— or —CH($NR_{11}R_{12}$)— wherein $R_{11}$ and $R_{12}$ are hydrogen, —$C_1$-$C_9$ alkyl, or $NR_{11}R_{12}$, taken together, form a 5–10 membered aromatic or non-aromatic carbocycle in which one ring carbon atom is replaced with a nitrogen atom and up to 3 of the remaining ring carbon atoms are independently replaced with a N, O or S atom.

30. The compound of claim 10 wherein X is —C(O)—, —CH(OH)—, —CH(Br)—, —$CH_2$— or —CH($NR_{11}R_{12}$)— wherein $R_{11}$ and $R_{12}$ are hydrogen, —$C_1$-$C_9$ alkyl, or $NR_{11}R_{12}$, taken together, form a 5–10 membered aromatic or non-aromatic carbocycle in which one ring carbon atom is replaced with a nitrogen atom and up to 3 of the remaining ring carbon atoms are independently replaced with a N, O or S atom.

31. The compound of claim 6 wherein X is —C(O)—, —CH(OH)—, —CH(Br)— or —$CH_2$—.

32. The compound of claim 6 wherein X is —$CH_2$—.

33. The compound of claim 8 wherein X is —C(O)—, —CH(OH)—, —CH(Br)— or —$CH_2$—.

34. The compound of claim 8 wherein X is —$CH_2$—.

35. The compound of claim 9 wherein X is —C(O)—, —CH(OH)—, —CH(Br)— or —$CH_2$—.

36. The compound of claim 9 wherein X is —$OH_2$—.

37. The compound of claim 10 wherein X is —C(O)—, —CH(OH)—, —CH(Br)— or —$CH_2$—.

38. The compound of claim 10 wherein X is —$CH_2$—.

39. The compound of claim 13 wherein X is —C(O)—, —CH(OH)—, —CH(Br)— or —$OH_2$—.

40. The compound of claim 13 wherein X is —$CH_2$—.

41. The compound of claim 14 wherein X is —C(O)—, —CH(OH)—, —CH(Br)— or —$CH_2$—.

42. The compound of claim 14 wherein X is —$CH_2$—.

43. The compound of claim 18 wherein X is —C(O)—, —CH(OH)—, —CH(Br)— or —$CH_2$—.

44. The compound of claim 18 wherein X is —$CH_2$—.

45. The compound of claim 19 wherein X is —C(O)—, —CH(OH)—, —CH(Br)— or —$CH_2$—.

46. The compound of claim 19 wherein X is —$CH_2$—.

47. The compound of claim 20 wherein X is —C(O)—, —CH(OH)—, —CH(Br)— or —$CH_2$—.

48. The compound of claim 20 wherein X is —$CH_2$—.

49. The compound of claim 21 wherein X is —C(O)—, —CH(OH)—, —CH(Br)— or —$CH_2$—.

50. The compound of claim 21 wherein X is —$CH_2$—.

51. A compound of the formula (III)

or a pharmaceutically acceptable hydrate or salt thereof, wherein:

X is —$CH_2$—;

$R_2$ and $R_3$ are independently -hydrogen, -halo, -alkylhalo, -hydroxy, —O—($C_1$-$C_5$ alkyl), —$C_1$-$C_3$ alkyl, —$NO_2$, —$NH_2$, —$CONH_2$, —C(O)OH, —OC(O)—$C_1$-$C_5$ alkyl or —C(O)O—$C_1$-$C_5$ alkyl;

$R_8$ and $R_9$ are independently -hydrogen or -A-B; with the proviso that R2, R3, R8 and R9 do not represent hydrogen simultaneously;

A is —SO₂—, —SO₂NH— or —NHCO—; and

B is —C₁–C₃ alkyl, —NZ₁Z₂, -alkylamino or a 5–10 membered aromatic or non-aromatic carbocycle in which 1–4 of the ring carbon atoms are independently replaced with a N, O or S atom, wherein the alkylamino or 5–10 membered aromatic or non-aromatic carbocycle is unsubstituted or substituted with one or more of -alkanol, -alkylamino, -aminoalkyl, -aminodialkyl or a 5–10 membered aromatic or non-aromatic carbocycle in which 1–4 of the ring carbon atoms are independently replaced with a N, O or S atom, wherein the -alkanol, -alkylamino, -aminoalkyl, -aminodialkyl or 5–10 membered aromatic or non-aromatic carbocycle is unsubstituted or substituted with —C₁–C₈, alkyl or -alkanol; and $Z_1$ and $Z_2$ are independently -hydrogen or —C₁–C₈ alkyl, which is unsubstituted or substituted with one or more of -hydroxy or —NZ₃Z₄, where $Z_3$ and $Z_4$ are independently —H or —C₁–C₃ alkyl, which is unsubstituted or substituted with one or more of -hydroxy or —NH₂, or N, $Z_3$ and $Z_4$ are taken together to a 5–10 membered aromatic or non-aromatic carbocycle in which 1–4 ring carbon atoms are independently replaced with a N, O or S atom, at least one of which is a nitrogen atom, or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom.

52. The compound of claim 51, wherein A is —SO₂— and B is —NZ₁Z₂.

53. The compound of claim 52, wherein $Z_1$ and $Z_2$ are independently hydrogen, or —C₁–C₅ alkyl, unsubstituted or substituted with hydroxy or —NZ₃Z₄, or, taken together, —NZ₁Z₂ form a 5–10 membered aromatic or non-aromatic carbocycle in which 1–4 ring carbon atoms are independently replaced with a N, O or S atom, at least one of which is a nitrogen atom.

54. The compound of claim 53, wherein $Z_3$ and $Z_4$ are independently hydrogen, or —C₁–C₃ alkyl, unsubstituted or substituted with hydroxy or —NH₂ or, taken together, NZ₃Z₄ form a 5–10 membered aromatic or non-aromatic carbocycle in which 1–4 ring carbon atoms are independently replaced with a N, O or S atom, at least one of which is a nitrogen atom.

55. The compound of claim 54, wherein N,$Z_3$ and $Z_4$, taken together form an unsubstituted piperidine, piperazine or morpholine group, or a piperazine, pyrrolidine or imidazole group which may be unsubstituted or substituted with —N—(C₁–C₅ alkyl) or —N—C(O)(C₁–C₅ alkyl).

56. The compound of claim 53, wherein either NZ₁Z₂ or NZ₃Z₄ is a 5–10 membered aromatic or non-aromatic carbocycle in which one ring carbon atom is replaced with a nitrogen atom and up to 3 of the remaining ring carbon atoms are independently replaced with a N, O or S atom, the carbocycle being unsubstituted or substituted with —C₁–C₅ alkyl, -alkanol or -alkylamino.

57. A composition comprising an effective amount of a compound or pharmaceutically acceptable salt or hydrate of a compound having the formula:

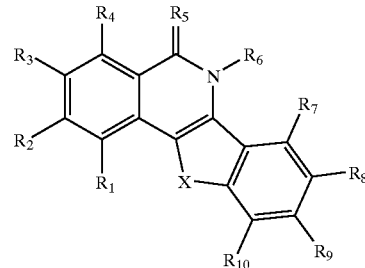

wherein:

$R_5$ is O, NH or S;

$R_6$ is —H or C₁–C₄ alkyl;

X is —CH₂—, —CH(halo)-, —CH(OH)(CH₂)ₙ—, —CH(OH)-arylene-, —O—, —NH—, —S— or —CH(NR₁₁R₁₂)—, wherein n is an integer ranging from 0–5;

$R_{11}$, and $R_{12}$ are independently -hydrogen or —C₁–C₉ alkyl, or N, $R_{11}$, and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$, and $R_{10}$ are independently -hydrogen, -halo, -hydroxy, —O—(C₁–C₅ alkyl), —C₁–C₁₀ alkyl, -alkylhalo, —C₂–C₁₀ alkenyl —C₃–C₈ carbocycle, -aryl, —NH₂, -alkylamino, —C(O)OH, —C(O)O(C₁–C₅ alkyl), —OC(O)(C₁–C₅ alkyl), NO₂ or -A-B;

A is —SO₂—, —SO₂NH—, —NHCO—, —NHCONH—, —O—, —CO—, —OC(O)—, —C(O)O—, —CONH—, —CON(C₁–C₄ alkyl)-, —NH—, —CH₂—, —S— or —C(S)—;

B is —C₁–C₁₀ alkyl, —C₂–C₁₀ alkenyl, —C₃–C₈ carbocycle, -aryl, —NZ₁Z₂, -alkylamino, -aminodialkyl, -arylamido, —C(O)OH, —C(O)O—(C₁–C₅ alkyl), C(O)O-phenyl, a 5–10 membered aromatic or non-aromatic carbocycle in which 1–4 of the ring carbon atoms are independently replaced with a N, O or S atom, or B is a C₁–C₅ alkyl group in which one of the C₁–C₅ alkyl group's hydrogen atoms is replaced with a 5–10 membered aromatic or non-aromatic carbocycle in which 1–4 of the carbocycle's ring carbon atoms are independently renlaced with a N, O or S atom, any of the foregoing B groups being unsubstituted or substituted with one or more of —O—(C₁–C₅ alkyl), -halo, -alkylhalo, -alkanol, -alkylamino, -hydroxy, —NO₂, —NH₂, -aminoalkyl, -aminodialkyl, —C₁–C₁₀ alkyl, —C₂–C₁₀ alkenyl, —C₂–C₁₀ alkenyl, -aryl -benzyl, -alkylamido, -alkylcarboxy, —C₁–C₅ alkylene-C(O)O—C₁–C₅ alkyl, —C₁–C₅ alkylene-OC(O)—C₁–C₅ alkyl, or a 5–10 membered aromatic or non-aromatic carbocycle in which 1–4 ring carbon atoms are independently replaced with a N, O or S atom, at least one of which is a nitrogen atom; and $Z_1$ and $Z_2$ are independently —H or —C₁–C₁₀ alkyl, which is unsubstituted or substituted with one or more of -halo, —OH or —N($Z_3$)($Z_4$), where $Z_3$ and $Z_4$ are independently, —H or —C$_1$–C$_5$ alkyl, which is unsubstituted or substituted with one or more of -halo, -hydroxy or —NH$_2$; or N, Z$_3$ and Z$_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, Z$_1$ and Z$_2$ are taken together to form a 5–10 membered aromatic or non-aromatic carbocycle in which 1–4 ring carbon atoms are independently replaced with a N, O or S atom, at least one of which is a nitrogen atom, and a pharmaceutically acceptable carrier.

58. A composition comprising an effective amount of a compound or pharmaceutically acceptable salt or hydrate of a compound having the formula:

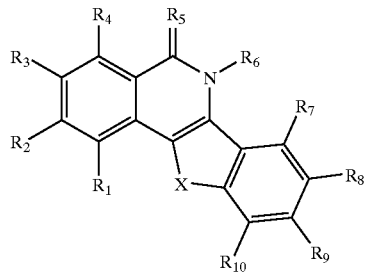

wherein:

R$_5$ is NH or S;

R$_6$ is —H or C$_1$–C$_4$ alkyl;

X is —C(O)—, —CH$_2$—, —CH(halo)-, —CH(OH)(CH$_2$)$_n$—, —CH(OH)-arylene-, —O—, —NH—, —S— or —CH(NR$_{11}$R$_{12}$)—, wherein n is an integer ranging from 0–5;

R$_{11}$ and R$_{12}$ are independently -hydrogen or —C$_1$–C$_9$ alkyl or N, R$_{11}$ and R$_{12}$ are taken together to form a 5–10 membered aromatic or non-aromatic carbocycle in which 1–4 ring carbon atoms are independently replaced with a N, O or S atom, at least one of which is a nitrogen atom;

R$_1$, R$_2$, R$_3$, R$_4$, R$_7$, R$_8$, R$_9$, and R$_{10}$ are independently -hydrogen, -halo, -hydroxy, —O—(C$_1$–C$_5$ alkyl), —C$_1$–C$_{10}$ alkyl, -alkylhalo, —C$_2$–C$_{10}$ alkenyl —C$_3$–C$_8$ carbocycle, -aryl, —NH$_2$, -alkylamino, —C(O)OH, —C(O)O(C$_1$–C$_5$ alkyl), —OC(O)(C$_1$–C$_5$ alkyl), NO$_2$ or -A-B;

A is —SO$_2$—, —SO$_2$NH—, —NHCO—, —NHCONH—, —O—, —CO—, —OC(O)—, —C(O)O—, —CONH—, —CON(C$_1$–C$_4$ alkyl)-, —NH—, —CH$_2$—, —S— or —C(S)—;

B is —C$_1$–C$_{10}$ alkyl, —C$_1$–C$_{10}$ alkenyl, —C$_3$–C$_8$ carbocycle, -aryl, —NZ$_1$Z$_2$, -alkylamino, -aminodialkyl, -arylamido, —C(O)OH, —C(O)O—(C$_1$–C$_5$ alkyl), C(O)O-phenyl, a 5–10 membered aromatic or non-aromatic carbocycle in which 1–4 of the ring carbon atoms are independently replaced with a N, O or S atom, or B is a C$_1$–C$_5$ alkyl group in which one of the C$_1$–C$_5$ alkyl group's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O—(C$_1$–C$_5$ alkyl), -halo, -alkylhalo, -alkanol, -alkylamino, -hydroxy, —NO$_2$, —NH$_2$, -aminoalkyl, -aminodialkyl, —C$_1$–C$_{10}$ alkyl, —C$_2$–C$_{10}$ alkenyl, —C$_2$–C$_{10}$ alkenyl, -aryl -benzyl, -alkylamido, -alkylcarboxy, —C$_1$–C$_5$ alkylene-C(O)O—C$_1$–C$_5$ alkyl, —C$_1$–C$_5$ alkylene-OC(O)—C$_1$–C$_5$ alkyl, or a 5–10 membered aromatic or non-aromatic carbocycle in which 1–4 ring carbon atoms are independently replaced with a N, O or S atom, at least one of which is a nitrogen atom; and Z$_1$ and Z$_2$ are independently —H or —C$_1$–C$_{10}$ alkyl, which is unsubstituted or substituted with one or more of -halo, —OH or —N(Z$_3$)(Z$_4$), where Z$_3$ and Z$_4$ are independently, —H or —C$_1$–C$_5$ alkyl, which is unsubstituted or substituted with one or more of -halo, -hydroxy or —NH$_2$; or N, Z$_3$ and Z$_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, Z$_1$ and Z$_2$ are taken together to form a 5–10 membered aromatic or non-aromatic carbocycle in which 1–4 ring carbon atoms are independently replaced with a N, O or S atom, at least one of which is a nitrogen atom, and a pharmaceutically acceptable carrier.

59. A composition comprising an effective amount of a compound or pharmaceutically acceptable salt or hydrate of the compound of claim 3 and a pharmaceutically acceptable carrier.

60. A composition comprising an effective amount of a compound or pharmaceutically acceptable salt or hydrate of a compound having the formula:

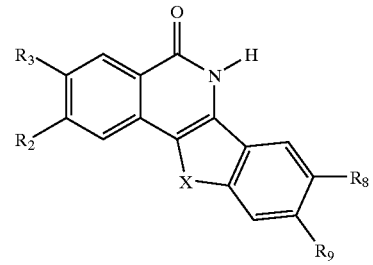

wherein:

X is —CH$_2$— or —O—;

R$_2$ and R$_3$ are independently -hydrogen, -halo, -alkylhalo, -hydroxy, —O—(C$_1$–C$_5$ alkyl), —C$_1$–C$_3$ alkyl, —NO$_2$—, —NH$_2$, —CONH$_2$, —C(O)OH, —OC(O)—C$_1$–C$_5$ alkyl or —C(O)O—C$_1$–C$_5$ alkyl;

R$_8$ and R$_9$ are independently -hydrogen or -A-B;

A is —SO$_2$—, —SO$_2$NH— or —NHCO—;

B is —C$_1$–C$_3$ alkyl, —NZ$_1$Z$_2$, -alkylamino or a 5–10 membered aromatic or non-aromatic carbocycle in which 1–4 of the ring carbon atoms are independently replaced with a N, O or S atom, wherein the alkylamino or 5–10 membered aromatic or non-aromatic carbocycle is unsubstituted or substituted with one or more of -alkanol, -alkylamino, -aminoalkyl, -aminodialkyl a 5–10 membered aromatic or non-aromatic carbocycle in which 1–4 of the ring carbon atoms are independently replaced with a N, O or S atom, wherein the -alkanol, -alkylamino, -aminoalkyl, -aminodialkyl or 5–10 membered aromatic or non-aromatic carbocycle is unsubstituted or substituted with —C$_1$–C$_8$, alkyl or -alkanol; and Z$_1$ and Z$_2$ are independently -hydrogen or —C$_1$–C$_8$ alkyl, which is unsubstituted or substituted with one or more of -hydroxy or —NZ$_3$Z$_4$, where Z$_3$ and Z$_4$ are independently —H or —C₁–C₃ alkyl, which is unsubstituted or substituted with one or more of -hydroxy or —NH₂, or N, Z₃ and Z₄ are taken together to a 5–10 membered aromatic or non-aromatic carbocycle in which 1–4 ring carbon atoms are independently replaced with a N, O or S atom, at least one of which is a nitrogen atom, or N, Z₁ and Z₂ are taken together to form a 5–10 membered aromatic or non-aromatic carbocycle in which 1–4 ring carbon atoms are independently replaced with a N, O or S atom, at least one of which is a nitrogen atom,
and a pharmaceutically acceptable carrier.

61. The compound or pharmaceutically acceptable salt or hydrate of claim 51, wherein either R⁸ is hydrogen and R⁹ is -A-B, or R⁸ is -A-B and R⁹ is hydrogen.

62. The compound of claim 2 being

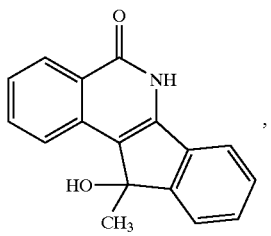,

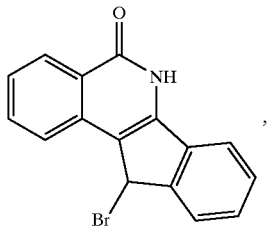,

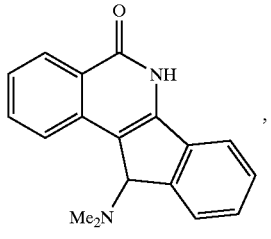,

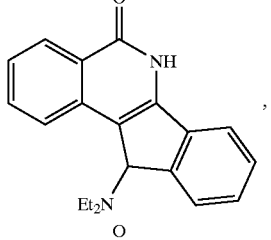,

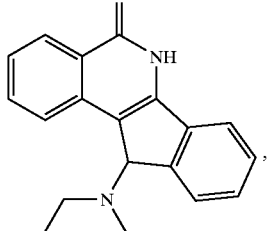,

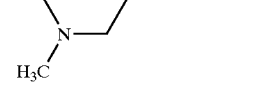

-continued

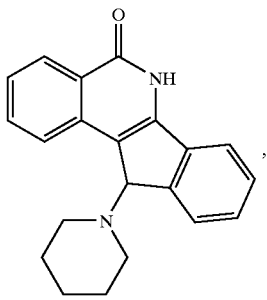,

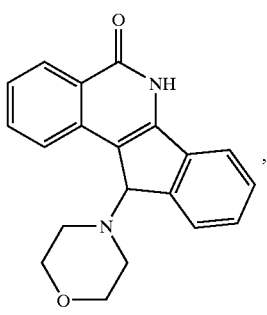,

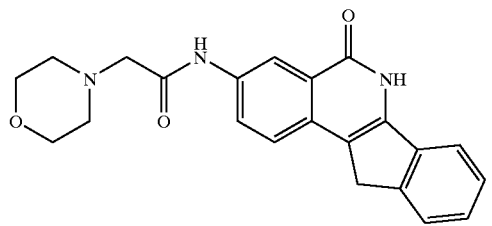,

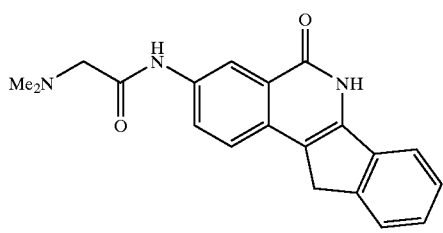,

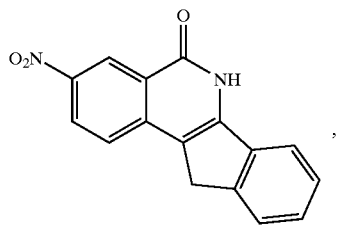,

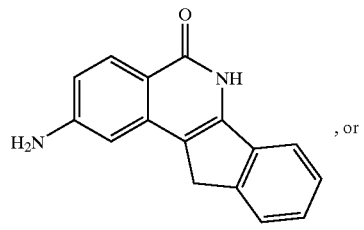, or

-continued
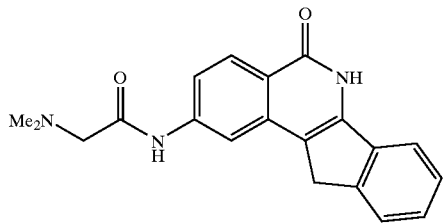
or a pharmaceutically acceptable hydrate or salt thereof.
63. The compound of claim 3 being
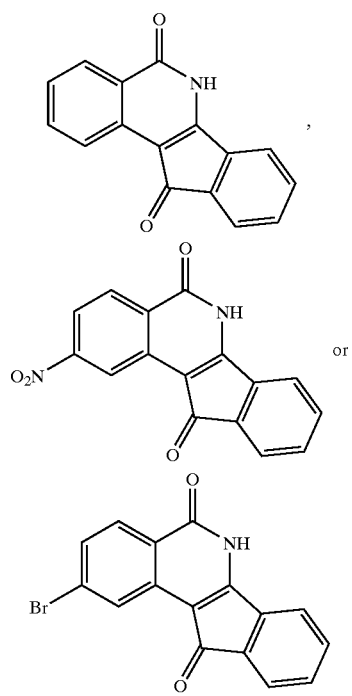
or a pharmaceutically acceptable hydrate or salt thereof.
64. The compound of claim 51 being
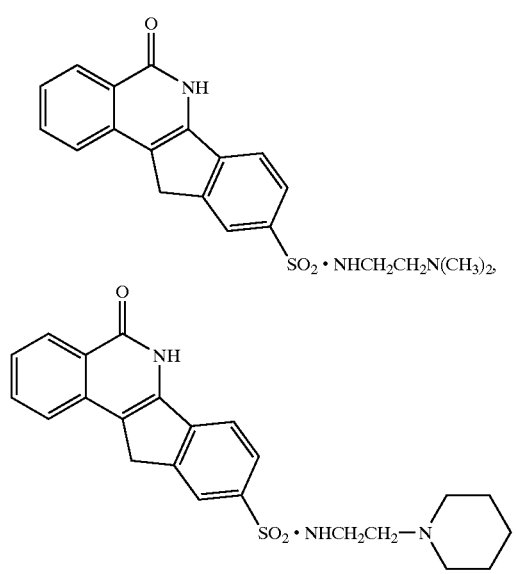
-continued
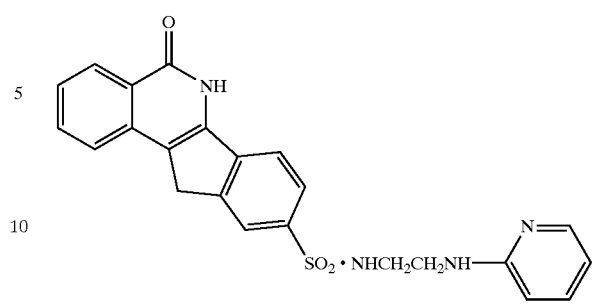
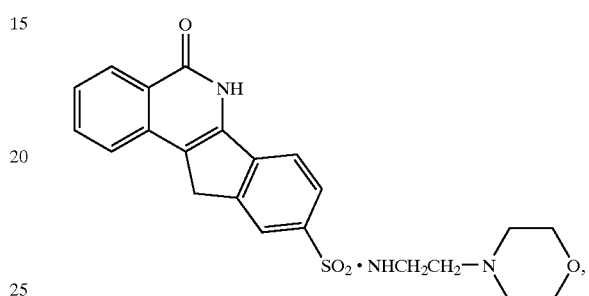
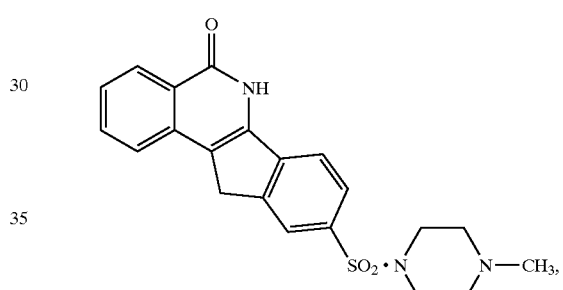
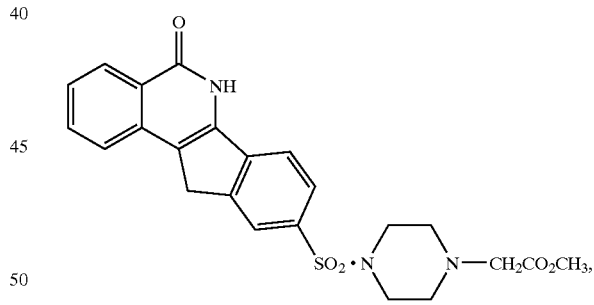
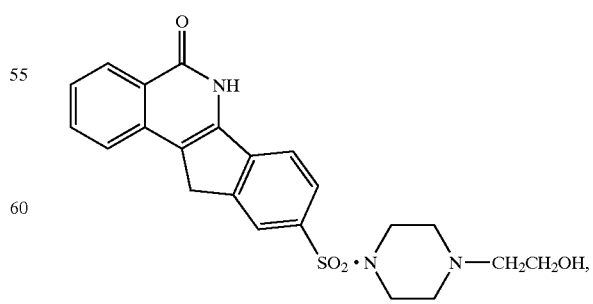

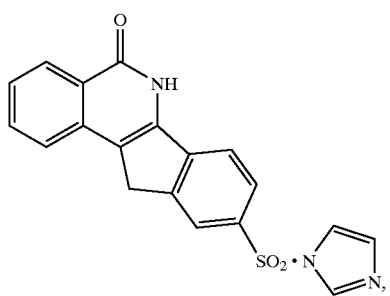
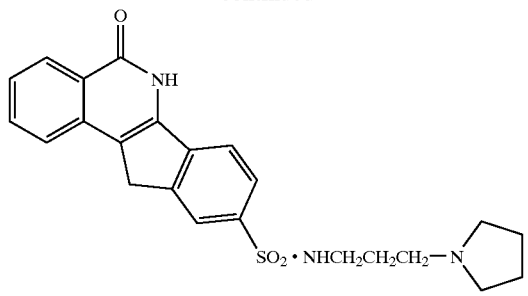
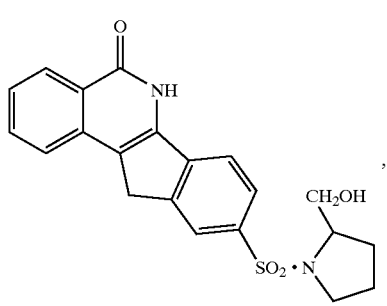
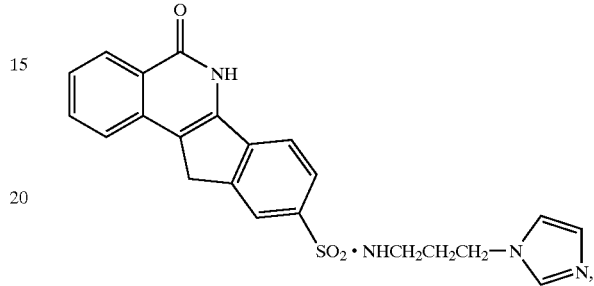
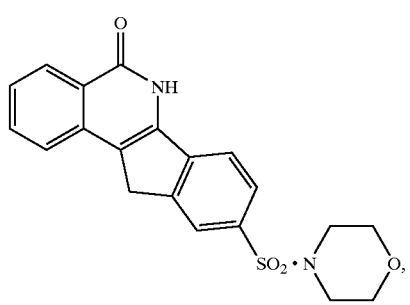
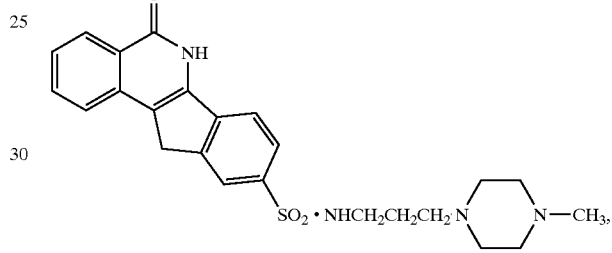
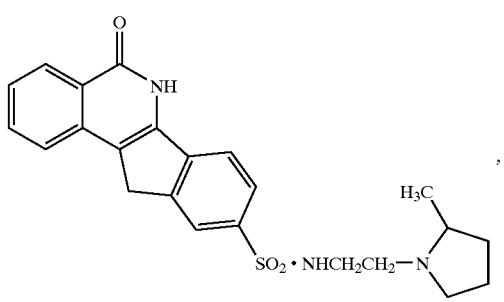
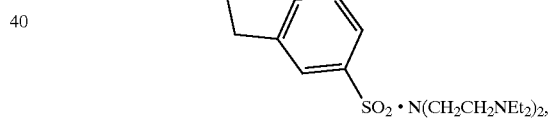
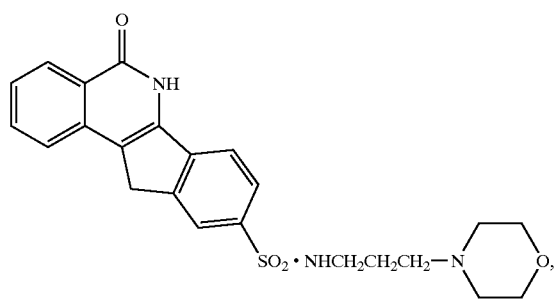
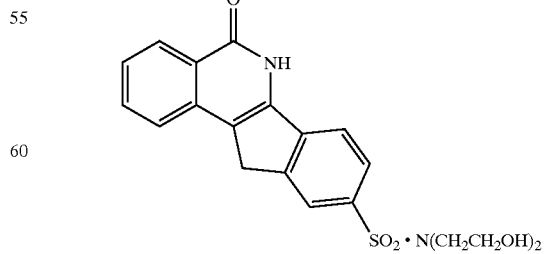

or a pharmaceutically acceptable hydrate or salt thereof.

65. A method for treating an inflammatory disease, comprising administering to a subject in need thereof a compound or a pharmaceutically acceptable hydrate or salt of a compound of claim 62 in an amount sufficient to treat the inflammatory disease.

66. A method for treating an inflammatory disease, comprising administering to a subject in need thereof a compound or a pharmaceutically acceptable hydrate or salt of a compound of claim 63 in an amount sufficient to treat the inflammatory disease.

67. A method for treating an inflammatory disease, comprising administering to a subject in need thereof a compound or a pharmaceutically acceptable hydrate or salt of a compound of claim 64 in an amount sufficient to treat the inflammatory disease.

68. A method for treating diabetes or a diabetic complication, comprising administering to a subject in need thereof a compound or a pharmaceutically acceptable hydrate or salt of a compound of claim 62 in an amount sufficient to treat the diabetes or diabetic complication.

69. A method for treating diabetes or a diabetic complication, comprising administering to a subject in need thereof a compound or a pharmaceutically acceptable hydrate or salt of a compound of claim 63 in an amount sufficient to treat the diabetes or diabetic complication.

70. A method for treating diabetes or a diabetic complication, comprising administering to a subject in need thereof a compound or a pharmaceutically acceptable hydrate or salt of a compound of claim 64 in an amount sufficient to treat the diabetes or diabetic complication.

71. A method for treating a reoxygenation injury resulting from organ transplantation, the method comprising administering to a subject in need thereof a compound or a pharmaceutically acceptable hydrate or salt of a compound of claim 62 in an amount sufficient to treat the reoxygenation injury.

72. A method for treating a reoxygenation injury resulting from organ transplantation, the method comprising administering to a subject in need thereof a compound or a pharmaceutically acceptable hydrate or salt of a compound of claim 63 in an amount sufficient to treat the reoxygenation injury.

73. A method for treating a reoxygenation injury resulting from organ transplantation, the method comprising administering to a subject in need thereof a compound or a pharmaceutically acceptable hydrate or salt of a compound of claim 64 in an amount sufficient to treat the reoxygenation injury.

74. A method for treating Parkinson's disease, comprising administering to a subject in need thereof a compound or a pharmaceutically acceptable hydrate or salt of a compound of claim 62 in an amount sufficient to treat Parkinson's disease.

75. A method for treating Parkinson's disease, comprising administering to a subject in need thereof a compound or a pharmaceutically acceptable hydrate or salt of a compound of claim 63 in an amount sufficient to treat Parkinson's disease.

76. A method for treating Parkinson's disease, comprising administering to a subject in need thereof a compound or a pharmaceutically acceptable hydrate or salt of a compound of claim 64 in an amount sufficient to treat Parkinson's disease.

77. A method for treating a reperfusion disease, comprising administering to a subject in need thereof a compound or a pharmaceutically acceptable hydrate or salt of a compound of claim 62 in an amount sufficient to treat the reperfusion disease.

78. A method for treating a reperfusion disease, comprising administering to a subject in need thereof a compound or a pharmaceutically acceptable hydrate or salt of a compound of claim 63 in an amount sufficient to treat the reperfusion disease.

79. A method for treating a reperfusion disease, comprising administering to a subject in need thereof a compound or a pharmaceutically acceptable hydrate or salt of a compound of claim 64 in an amount sufficient to treat the reperfusion disease.

80. The compound of claim 51 being

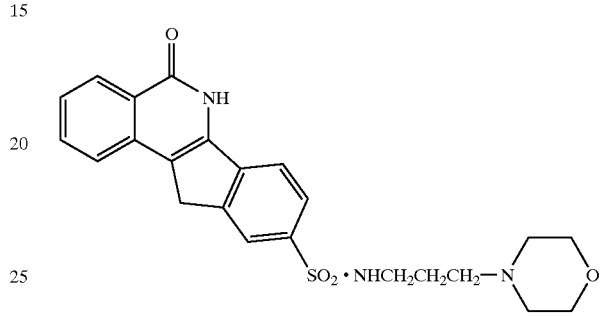

or a pharmaceutically acceptable hydrate or salt thereof.

81. A method for treating an inflammatory disease, comprising administering to a subject in need thereof a compound or a pharmaceutically acceptable hydrate or salt of a compound of claim 80 in an amount sufficient to treat the inflammatory disease.

82. A method for treating diabetes or a diabetic complication, comprising administering to a subject in need thereof a compound or a pharmaceutically acceptable hydrate or salt of a compound of claim 80 in an amount sufficient to treat the diabetes or diabetic complication.

83. A method for treating a reoxygenation injury resulting from organ transplantation, the method comprising administering to a subject in need thereof a compound or a pharmaceutically acceptable hydrate or salt of a compound of claim 80 in an amount sufficient to treat the reoxygenation injury.

84. A method for treating Parkinson's disease, comprising administering to a subject in need thereof a compound or a pharmaceutically acceptable hydrate or salt of a compound of claim 80 in an amount sufficient to treat Parkinson's disease.

85. A method for treating a reperfusion disease, comprising administering to a subject in need thereof a compound or a pharmaceutically acceptable hydrate or salt of a compound of claim 80 in an amount sufficient to treat the reperfusion disease.

86. A method for treating an inflammatory disease, comprising administering to a subject in need thereof a compound or a pharmaceutically acceptable hydrate or salt of a compound having the formula:

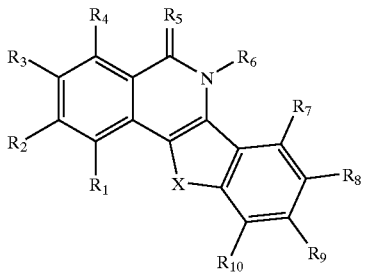

wherein:

$R_5$ is O, NH or S;

$R_6$ is —H or $C_1$-$C_4$ alkyl;

X is —$CH_2$—, —CH(halo)-, —CH(OH)($CH_2$)$_n$—, —CH(OH)-arylene-, —O—, —NH—, —S— or —CH($NR_{11}R_{12}$)—, wherein n is an integer ranging from 0–5;

$R_{11}$ and $R_{12}$ are independently -hydrogen or —$C_1$-$C_9$ alkyl, or N, $R_{11}$, and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$ and $R_{10}$ are independently -hydrogen, -halo, -hydroxy, —O—($C_1$-$C_5$ alkyl), —$C_1$-$C_{10}$ alkyl, -alkylhalo, —$C_2$-$C_{10}$ alkenyl, —$C_3$-$C_8$ carbocycle, -aryl, —$NH_2$, -alkylamino, —C(O)OH, —C(O)O($C_1$-$C_5$ alkyl), —OC(O)($C_1$-$C_5$ alkyl), $NO_2$ or -A-B;

A is —$SO_2$—, —$SO_2NH$—, —NHCO—, —NHCONH—, —O—, —CO—, —OC(O)—, —C(O)O—, —CONH—, —CON($C_1$-$C_4$ alkyl)-, —NH—, —$CH_2$—, —S— or —C(S)—;

B is —$C_1$-$C_{10}$ alkyl, —$C_2$-$C_{10}$ alkenyl, —$C_3$-$C_8$ carbocycle, -aryl, —$NZ_1Z_2$, -alkylamino, -aminodialkyl, -arylamido, —C(O)OH, —C(O)O—($C_1$-$C_5$ alkyl), C(O)O-phenyl, a 5–10 membered aromatic or non-aromatic carbocycle in which 1–4 of the ring carbon atoms are independently replaced with a N, O or S atom, or B is a $C_1$-$C_5$ alkyl group in which one of the $C_1$-$C_5$ alkyl group's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O—($C_1$-$C_5$ alkyl), -halo, -alkylhalo, -alkanol, -alkylamino, -hydroxy, —$NO_2$, —$NH_2$, -aminoalkyl, -aminodialkyl, —$C_1$-$C_{10}$ alkyl, —$C_2$-$C_{10}$ alkenyl, —$C_2$-$C_{10}$ alkenyl, -aryl, -benzyl, -alkylamido, -alkylcarboxy, —$C_1$-$C_5$ alkylene-C(O)O—$C_1$-$C_5$ alkyl, —$C_1$-$C_5$ alkylene-OC(O)—$C_1$-$C_5$ alkyl, or a 5–10 membered aromatic or non-aromatic carbocycle in which 1–4 ring carbon atoms are independently replaced with a N, O or S atom, at least one of which is a nitrogen atom; and $Z_1$ and $Z_2$ are independently —H or —$C_1$-$C_{10}$ alkyl, which is unsubstituted or substituted with one or more of -halo, —OH or —N($Z_3$)($Z_4$), where $Z_3$ and $Z_4$ are independently, —H or —$C_1$-$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the inflammatory disease.

87. The method of claim 86, wherein the subject is a human.

88. The method of claim 86, wherein the inflammatory disease is an inflammatory disease of a joint, a chronic inflammatory disease of the gum, an inflammatory bowel disease, an inflammatory lung disease, an inflammatory disease of the central nervous system, or an inflammatory disease of the eye.

89. The method of claim 86, wherein the inflammatory disease is gram-positive shock, gram negative shock, hemorrhagic shock, anaphylactic shock, traumatic shock and chemotherapeutic shock.

90. A method for treating a reperfusion disease, comprising administering to a subject in need thereof a compound or a pharmaceutically acceptable hydrate or salt of a compound having the formula:

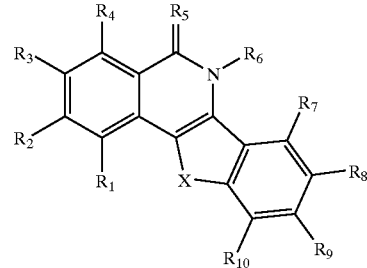

wherein:

$R_5$ is O, NH or S;

$R_6$ is —H or $C_1$-$C_4$ alkyl;

X is —$CH_2$—, —CH(halo)-, —CH(OH)($CH_2$)$_n$—, —CH(OH)-arylene-, —O—, —NH—, —S— or —CH($NR_{11}R_{12}$)—, wherein n is an integer ranging from 0–5;

$R_{11}$ and $R_{12}$ are independently -hydrogen or —$C_1$-$C_9$ alkyl, or N, $R_{11}$, and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$ and $R_{10}$ are independently -hydrogen, -halo, -hydroxy, —O—($C_1$-$C_5$ alkyl), —$C_1$-$C_{10}$ alkyl, -alkylhalo, —$C_2$-$C_{10}$ alkenyl, —$C_3$-$C_8$ carbocycle, -aryl, —$NH_2$, -alkylamino, —C(O)OH, —C(O)O($C_1$-$C_5$ alkyl), —OC(O)($C_1$-$C_5$ alkyl), $NO_2$ or -A-B;

A is —$SO_2$—, —$SO_2NH$—, —NHCO—, —NHCONH—, —O—, —CO—, —OC(O)—, —C(O)O—, —CONH—, —CON($C_1$-$C_4$ alkyl)-, —NH—, —$CH_2$—, —S— or —C(S)—;

B is —$C_1$-$C_{10}$ alkyl, —$C_2$-$C_{10}$ alkenyl, —$C_3$-$C_8$ carbocycle, -aryl, —$NZ_1Z_2$, -alkylamino, -aminodialkyl, -arylamido, —C(O)OH, —C(O)O—($C_1$-$C_5$ alkyl), C(O)O-phenyl, a 5–10 membered aromatic or non-aromatic carbocycle in which 1–4 of the ring carbon atoms are independently replaced with a N, O or S atom, or B is a $C_1$-$C_5$ alkyl group in which one of the $C_1$-$C_5$ alkyl group's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O—($C_1$–$C_5$ alkyl), -halo, -alkylhalo, -alkanol, -alkylamino, -hydroxy, —$NO_2$, —$NH_2$, -aminoalkyl, -aminodialkyl, —$C_1$–$C_{10}$ alkyl, —$C_2$–$C_{10}$ alkenyl, —$C_2$–$C_{10}$ alkenyl, -aryl, -benzyl, -alkylamido, -alkylcarboxy, —$C_1$–$C_5$ alkylene-C(O)O—$C_1$–$C_5$ alkyl, —$C_1$–$C_5$ alkylene-OC(O)—$C_1$–$C_5$ alkyl, or a 5–10 membered aromatic or non-aromatic carbocycle in which 1–4 ring carbon atoms are independently replaced with a N, O or S atom, at least one of which is a nitrogen atom; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the reperfusion disease.

91. The method of claim 90, wherein the reperfusion disease is myocardial infarction.

92. The method of claim 90, wherein the reperfusion disease is stroke.

93. The method of claim 90, wherein the subject is a human.

94. A method for treating diabetes or a diabetic complication, comprising administering to a subject in need thereof a compound or a pharmaceutically acceptable hydrate or salt of a compound having the formula:

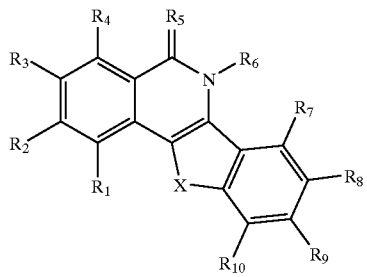

wherein:

$R_5$ is O, NH or S;

$R_6$ is —H or $C_1$–$C_4$ alkyl;

X is —$CH_2$—, —CH(halo)-, —CH(OH)($CH_2$)$_n$—, —CH(OH)-arylene-, —O—, —NH—, —S— or —CH($NR_{11}R_{12}$)—, wherein n is an integer ranging from 0–5;

$R_{11}$ and $R_{12}$ are independently -hydrogen or —$C_1$–$C_9$ alkyl, or N, $R_{11}$, and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), $NO_2$ or -A-B;

A is —$SO_2$—, —$SO_2NH$—, —NHCO—, —NHCONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, —$C_3$–$C_8$ carbocycle, -aryl, —$NZ_1Z_2$, -alkylamino, -aminodialkyl, -arylamido, —C(O)OH, —C(O)O—($C_1$–$C_5$ alkyl), C(O)O-phenyl, a 5–10 membered aromatic or non-aromatic carbocycle in which 1–4 of the ring carbon atoms are independently replaced with a N, O or S atom, or B is a $C_1$–$C_5$ alkyl group in which one of the $C_1$–$C_5$ alkyl group's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O—($C_1$–$C_5$ alkyl), -halo, -alkylhalo, -alkanol, -alkylamino, -hydroxy, —$NO_2$, —$NH_2$, -aminoalkyl, -aminodialkyl, —$C_1$–$C_{10}$ alkyl, —$C_2$–$C_{10}$ alkenyl, —$C_2$–$C_{10}$ alkenyl, -aryl, -benzyl, -alkylamido, -alkylcarboxy, —$C_1$–$C_5$ alkylene-C(O)O—$C_1$–$C_5$ alkyl, —$C_1$–$C_5$ alkylene-OC(O)—$C_1$–$C_5$ alkyl, or a 5–10 membered aromatic or non-aromatic carbocycle in which 1–4 ring carbon atoms are independently replaced with a N, O or S atom, at least one of which is a nitrogen atom; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the diabetes or the diabetic complication.

95. A method for treating reoxygenation injury resulting from organ transplantation, the method comprising administering to a subject in need thereof a compound or a pharmaceutically acceptable hydrate or salt of a compound having the formula:

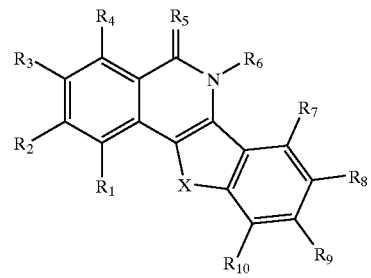

wherein:

$R_5$ is O, NH or S;

$R_6$ is —H or $C_1$–$C_4$ alkyl;

X is —$CH_2$—, —CH(halo)-, —CH(OH)($CH_2$)$_n$—, —CH(OH)-arylene-, —O—, —NH—, —S— or —CH($NR_{11}R_{12}$)—, wherein n is an integer ranging from 0–5;

$R_{11}$ and $R_{12}$ are independently -hydrogen or —$C_1$–$C_9$ alkyl, or N, $R_{11}$, and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), $NO_2$ or -A-B;

A is —$SO_2$—, —$SO_2NH$—, —NHCO—, —NHCONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, —$C_3$–$C_8$ carbocycle, -aryl, —$NZ_1Z_2$, -alkylamino, -aminodialkyl, -arylamido, —C(O)OH, —C(O)O—($C_1$–$C_5$ alkyl), C(O)O-phenyl, a 5–10 membered aromatic or non-aromatic carbocycle in which 1–4 of the ring carbon atoms are independently replaced with a N, O or S atom, or B is a $C_1$–$C_5$ alkyl group in which one of the $C_1$–$C_5$ alkyl group's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O—($C_1$–$C_5$ alkyl), -halo, -alkylhalo, -alkanol, -alkylamino, -hydroxy, —$NO_2$, —$NH_2$, -aminoalkyl, -aminodialkyl, —$C_1$–$C_{10}$ alkyl, —$C_2$–$C_{10}$ alkenyl, —$C_2$–$C_{10}$ alkenyl, -aryl, -benzyl, -alkylamido, -alkylcarboxy, —$C_1$–$C_5$ alkylene-C(O)O—$C_1$–$C_5$ alkyl, —$C_1$–$C_5$ alkylene-OC(O)—$C_1$–$C_5$ alkyl, or a 5–10 membered aromatic or non-aromatic carbocycle in which 1–4 ring carbon atoms are independently replaced with a N, O or S atom, at least one of which is a nitrogen atom; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the reoxygenation injury.

96. A method for treating Parkinson's disease, comprising administering to a subject in need thereof a compound or a pharmaceutically acceptable hydrate or salt of a compound having the formula:

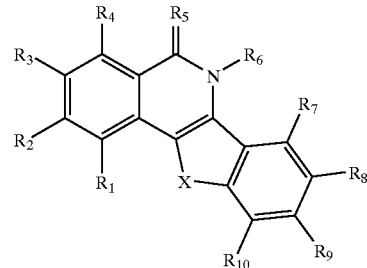

wherein:

$R_5$ is O, NH or S;

$R_6$ is —H or $C_1$–$C_4$ alkyl;

X is —$CH_2$—, —CH(halo)-, —CH(OH)($CH_2$)$_n$—, —CH(OH)-arylene-, —O—, —NH—, —S— or —CH($NR_{11}R_{12}$)—, wherein n is an integer ranging from 0–5;

$R_{11}$ and $R_{12}$ are independently -hydrogen or —$C_1$–$C_9$ alkyl, or N, $R_{11}$, and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), $NO_2$ or -A-B;

A is —$SO_2$—, —$SO_2NH$—, —NHCO—, —NHCONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, —$C_3$–$C_8$ carbocycle, -aryl, —$NZ_1Z_2$, -alkylamino, -aminodialkyl, -arylamido, —C(O)OH, —C(O)O—($C_1$–$C_5$ alkyl), C(O)O-phenyl, a 5–10 membered aromatic or non-aromatic carbocycle in which 1–4 of the ring carbon atoms are independently replaced with a N, O or S atom, or B is a $C_1$–$C_5$ alkyl group in which one of the $C_1$–$C_5$ alkyl group's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O—($C_1$–$C_5$ alkyl), -halo, -alkylhalo, -alkanol, -alkylamino, -hydroxy, —$NO_2$, —$NH_2$, -aminoalkyl, -aminodialkyl, —$C_1$–$C_{10}$ alkyl, —$C_2$–$C_{10}$ alkenyl, —$C_2$–$C_{10}$ alkenyl, -aryl, -benzyl, -alkylamido, -alkylcarboxy, —$C_1$–$C_5$ alkylene-C(O)O—$C_1$–$C_5$ alkyl, —$C_1$–$C_5$ alkylene-OC(O)—$C_1$–$C_5$ alkyl, or a 5–10 membered aromatic or non-aromatic carbo cycle in which 1–4 ring carbon atoms are independently replaced with a N, O or S atom, at least one of which is a nitrogen atom; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat Parkinson's disease.

97. A method for treating an inflammatory disease, comprising administering to a subject in need thereof a compound or a pharmaceutically acceptable hydrate or salt of a compound having the formula:

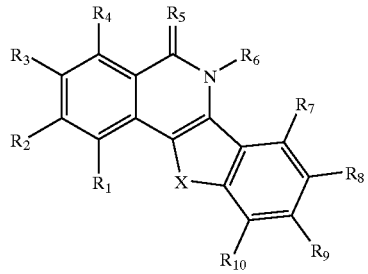

wherein:

$R_5$ is NH or S;

$R_6$ is —H or $C_1$–$C_4$ alkyl;

X is —$CH_2$—, —$CH_2$—, —CH(halo)-, —CH(OH)($CH_2$)$_n$—, —CH(OH)-arylene-, —O—, —NH—, —S— or —CH($NR_{11}R_{12}$)—, wherein n is an integer ranging from 0–5;

$R_{11}$ and $R_{12}$ are independently -hydrogen or —$C_1$–$C_9$ alkyl, or N, $R_{11}$, and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), $NO_2$ or -A-B;

A is —$SO_2$—, —$SO_2NH$—, —NHCO—, —NHCONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, —$C_3$–$C_8$ carbocycle, -aryl, —$NZ_1Z_2$, -alkylamino, -aminodialkyl, -arylamido, —C(O)OH, —C(O)O—($C_1$–$C_5$ alkyl), C(O)O-phenyl, a 5–10 membered aromatic or non-aromatic carbocycle in which 1–4 of the ring carbon atoms are independently replaced with a N, O or S atom, or B is a $C_1$–$C_5$ alkyl group in which one of the $C_1$–$C_5$ alkyl group's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O—($C_1$–$C_5$ alkyl), -halo, -alkylhalo, -alkanol, -alkylamino, -hydroxy, —$NO_2$, —$NH_2$, -aminoalkyl, -aminodialkyl, —$C_1$–$C_{10}$ alkyl, —$C_2$–$C_{10}$ alkenyl, —$C_2$–$C_{10}$ alkynyl, -aryl, -benzyl, -alkylamido, -alkylcarboxy, —$C_1$–$C_5$ alkylene-C(O)O—$C_1$–$C_5$ alkyl, —$C_1$–$C_5$ alkylene-OC(O)—$C_1$–$C_5$ alkyl, or a 5–10 membered aromatic or non-aromatic carbo cycle in which 1–4 ring carbon atoms are independently replaced with a N, O or S atom, at least one of which is a nitrogen atom; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the inflammatory disease.

98. The method of claim 97, wherein the subject is a human.

99. The method of claim 97, wherein the inflammatory disease is an inflammatory disease of a joint, a chronic inflammatory disease of the gum, an inflammatory bowel disease, an inflammatory lung disease, an inflammatory disease of the central nervous system, or an inflammatory disease of the eye.

100. The method of claim 97, wherein the inflammatory disease is gram-positive shock, gram negative shock, hemorrhagic shock, anaphylactic shock, traumatic shock and chemotherapeutic shock.

101. A method for treating a reperfusion disease, comprising administering to a subject in need thereof a compound or a pharmaceutically acceptable hydrate or salt of a compound having the formula:

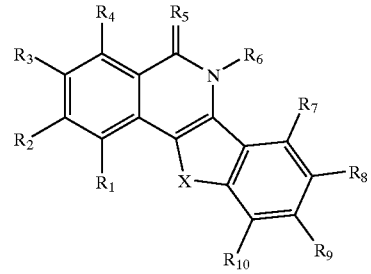

wherein:

$R_5$ is NH or S;

$R_6$ is —H or $C_1$–$C_4$ alkyl;

X is —C(O)—, —$CH_2$—, —CH(halo)-, —CH(OH)($CH_2$)$_n$—, —CH(OH)-arylene-, —O—, —NH—, —S— or —CH($NR_{11}R_{12}$)—, wherein n is an integer ranging from 0–5;

$R_{11}$ and $R_{12}$ are independently -hydrogen or —$C_1$–$C_9$ alkyl, or N, $R_{11}$, and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), $NO_2$ or -A-B;

A is —$SO_2$—, —$SO_2NH$—, —NHCO—, —NHCONH—, —O—, —CO—, —OC(O)—,

—C(O)O—, —CONH—, —CON($C_1$-$C_4$ alkyl)-, —NH—, —$CH_2$—, —S— or —C(S)—;

B is —$C_1$-$C_{10}$ alkyl, —$C_2$-$C_{10}$ alkenyl, —$C_3$-$C_8$ carbocycle, -aryl, —$NZ_1Z_2$, -alkylamino, -aminodialkyl, -arylamido, —C(O)OH, —C(O)O— ($C_1$-$C_5$ alkyl), C(O)O-phenyl, a 5–10 membered aromatic or non-aromatic carbocycle in which 1–4 of the ring carbon atoms are independently replaced with a N, O or S atom, or B is a $C_1$-$C_5$ alkyl group in which one of the $C_1$-$C_5$ alkyl group's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O—($C_1$-$C_5$ alkyl), -halo, -alkylhalo, -alkanol, -alkylamino, -hydroxy, —$NO_2$, —$NH_2$, -aminoalkyl, -aminodialkyl, —$C_1$-$C_{10}$ alkyl, —$C_2$-$C_{10}$ alkenyl, —$C_2$-$C_{10}$ alkynyl, -aryl, -benzyl, -alkylamido, -alkylcarboxy, —$C_1$-$C_5$ alkylene-C(O)O—$C_1$-$C_5$ alkyl, —$C_1$-$C_5$ alkylene-OC(O)—$C_1$-$C_5$ alkyl, or a 5–10 membered aromatic or non-aromatic carbo cycle in which 1–4 ring carbon atoms are independently replaced with a N, O or S atom, at least one of which is a nitrogen atom; and $Z_1$ and $Z_2$ are independently —H or —$C_1$-$C_{10}$ alkyl, which is unsubstituted or substituted with one or more of -halo, —OH or —N($Z_3$)($Z_4$), where $Z_3$ and $Z_4$ are independently, —H or —$C_1$-$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the reperfusion disease.

102. The method of claim 101, wherein the reperfusion disease is myocardial infarction.

103. The method of claim 101, wherein the reperfusion disease is stroke.

104. The method of claim 101, wherein the subject is a human.

105. A method for treating diabetes or a diabetic complication, comprising administering to a subject in need thereof a compound or a pharmaceutically acceptable hydrate or salt of a compound having the formula:

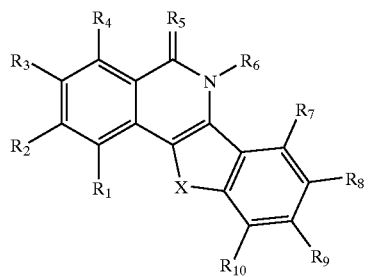

wherein:
$R_5$ is NH or S;
$R_6$ is —H or $C_1$-$C_4$ alkyl;
X is —$CH_2$—, —CH(halo)—, —CH(OH)($CH_2$)$_n$—, —CH(OH)-arylene-, —O—, —NH—, —S— or —CH($NR_{11}R_{12}$)—, wherein n is an integer ranging from 0–5;

$R_{11}$ and $R_{12}$ are independently-hydrogen or —$C_1$-$C_9$ alkyl, or N, $R_{11}$, and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$ and $R_{10}$ are independently -hydrogen, -halo, -hydroxy, —O—($C_1$-$C_5$ alkyl), —$C_1$-$C_{10}$ alkyl, -alkylhalo, —$C_2$-$C_{10}$ alkenyl, —$C_3$-$C_8$ carbocycle, -aryl, —$NH_2$, -alkylamino, —C(O)OH, —C(O)O($C_1$-$C_5$ alkyl), —OC(O)($C_1$-$C_5$ alkyl), $NO_2$ or -A-B;

A is —$SO_2$—, —$SO_2N$—, —NHCO—, —NHCONH—, —O—, —CO—, —OC(O)—, —C(O)O—, —CONH—, —CON($C_1$-$C_4$ alkyl)—, —NH—, —$CH_2$—, —S— or —C(S)—;

B is —$C_1$-$C_{10}$ alkyl, —$C_2$-$C_{10}$ alkenyl, —$C_3C_8$ carbocycle, -aryl, —$NZ_1Z_2$, -alkylamino, -aminodialkyl, -arylamido, —C(O)OH, —C(O)O— ($C_1$-$C_5$ alkyl), —C(O)O-phenyl, a 5–10 membered aromatic or non-aromatic carbocycle in which 1–4 of the ring carbon atoms are independently replaced with a N, O or S atom, or B is a $C_1$-$C_5$ alkyl group in which one of the $C_1$-$C_5$ alkyl group's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O— ($C_1$-$C_5$ alkyl), -halo, -alkylhalo, -alkanol, -alkylamino, -hydroxy, —$NO_2$, —$NH_2$, -aminoalkyl, -aminodialkyl, —$C_1$-$C_{10}$ alkyl, —$C_2$-$C_{10}$ alkenyl, —$C_2$-$C_{10}$ alkynyl, -aryl, -benzyl, -alkylamido, -alkylcarboxy, —$C_1$-$C_5$ alkylene-C(O)O—$C_1$-$C_5$ alkyl, —$C_1$-$C_5$ alkylene-OC(O)—$C_1$-$C_5$ alkyl, or a 5–10 membered aromatic or non-aromatic carbocycle in which 1–4 ring carbon atoms are independently replaced with a N, O or S atom, at least one of which is a nitrogen atom; and $Z_1$ and $Z_2$ are independently —H or —$C_1$-$C_{10}$ alkyl, which is unsubstituted or substituted with one or more of -halo, —OH or —N($Z_3$)($Z_4$), where $Z_3$ and $Z_4$ are independently, —H or —$C_1$-$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat diabetes or the diabetic complication.

106. A method for treating reoxygenation injury resulting from organ transplantation, the method comprising administering to a subject in need thereof a compound or a pharmaceutically acceptable hydrate or salt of a compound having the formula:

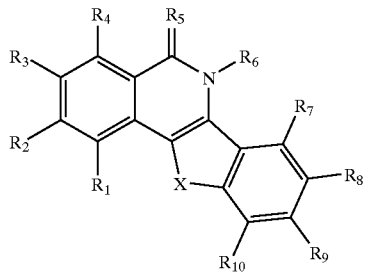

wherein:

$R_5$ is NH or S;

$R_6$ is —H or $C_1$–$C_4$ alkyl;

X is —C(O)—, —$CH_2$—, —CH(halo)—, —CH(OH)($CH_2$)$_n$—, —CH(OH)-arylene-, —O—, —NH—, —S— or —CH($NR_{11}R_{12}$)—, wherein n is an integer ranging from 0–5;

$R_{11}$ and $R_{12}$ are independently -hydrogen or —$C_1$–$C_9$ alkyl, or N, $R_{11}$, and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_8$ alkyl), —OC(O)($C_1$–$C_5$ alkyl), $NO_2$ or -A-B;

A is —$SO_2$—, —$SO_2$NH—, —NHCO—, —NHCONH—, —O—, —CO—, —OC(O)—, —C(O)O—, —CONH—, —CON($C_1$–$C_4$ alkyl)—, —NH—, —$CH_2$—, —S— or —C(S)—;

B is —$C_1$–$C_{10}$ alkyl, —$C_2$–$C_{10}$ alkenyl, —$C_3$–$C_8$ carbocycle, -aryl, —$NZ_1Z_2$, -alkylamino, -aminodialkyl, -arylamido, —C(O)OH, —C(O)O—($C_1$–$C_5$ alkyl), —C(O)O-phenyl, a 5–10 membered aromatic or non-aromatic carbocycle in which 1–4 of the ring carbon atoms are independently replaced with a N, O or S atom, or B is a $C_1$–$C_5$ alkyl group in which one of the $C_1$–$C_5$ alkyl group's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O—($C_1$–$C_5$ alkyl), -halo, -alkylhalo, -alkanol, -alkylamino, -hydroxy, —$NO_2$, —$NH_2$, -aminoalkyl, -aminodialkyl, —$C_1$–$C_{10}$ alkyl, —$C_2$–$C_{10}$ alkenyl, —$C_2$–$C_{10}$ alkynyl, -aryl, -benzyl, -alkylamido, -alkylcarboxy, —$C_1$–$C_5$ alkylene-C(O)O—$C_1$–$C_5$ alkyl, —$C_1$–$C_5$ alkylene-OC(O)—$C_1$–$C_5$ alkyl, or a 5–10 membered aromatic or non-aromatic carbocycle in which 1–4 ring carbon atoms are independently replaced with a N, O or S atom, at least one of which is a nitrogen atom; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the reoxygenation injury.

107. A method for treating Parkinson's disease, comprising administering to a subject in need thereof a compound or a pharmaceutically acceptable hydrate or salt of a compound having the formula:

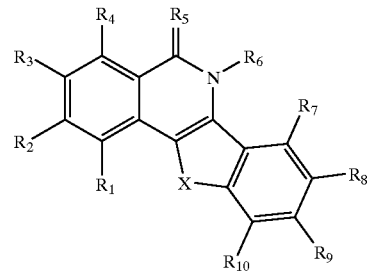

wherein:

$R_5$ is NH or S;

$R_6$ is —H or $C_1$–$C_4$ alkyl;

X is —C(O)—, —$CH_2$—, —CH(halo)—, —CH(OH)($CH_2$)$_n$—, —CH(OH)-arylene-, —O—, —NH—, —S— or —CH($NR_{11}R_{12}$)—, wherein n is an integer ranging from 0–5;

$R_{11}$ and $R_{12}$ are independently -hydrogen or —$C_1$–$C_9$ alkyl, or N, $R_{11}$, and $R_{12}$ are taken together to form a 5–10 membered aromatic or non-aromatic carbocycle in which 1–4 ring carbon atoms are independently replaced with a N, O or S atom, at least one of which is a nitrogen atom;

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), $NO_2$ or -A-B;

A is —$SO_2$—, —$SO_2$NH—, —NHCO—, —NHCONH—, —O—, —CO—, —OC(O)—, —C(O)O—, —CONH—, —CON($C_1$–$C_4$ alkyl)—, —NH—, —$CH_2$—, —S— or —C(S)—;

B is —$C_1$–$C_{10}$ alkyl, —$C_2$–$C_{10}$ alkenyl, —$C_3$–$C_8$ carbocycle, -aryl, —$NZ_1Z_2$, -alkylamino, -aminodialkyl, -arylamido, —C(O)OH, —C(O)O—($C_1$–$C_5$ alkyl), —C(O)O-phenyl, a 5–10 membered aromatic or non-aromatic carbocycle in which 1–4 of the ring carbon atoms are independently replaced with a N, O or S atom, or B is a $C_1$–$C_5$ alkyl group in which one of the $C_1$–$C_5$ alkyl group's hydrogen atoms is replaced with a 5–10 membered aromatic or non-aromatic carbocycle in which 1–4 of the carbocycle's ring carbon atoms are independently replaced with a N, O or S atom, any of the foregoing B groups being unsubstituted or substituted with one or more of —O—($C_1$–$C_5$ alkyl), -halo, -alkylhalo, -alkanol, -alkylamino, -hydroxy, —$NO_2$, —$NH_2$, -aminoalkyl, -aminodialkyl, —$C_1$–$C_{10}$ alkyl, —$C_2$–$C_{10}$ alkenyl, —$C_2$–$C_{10}$ alkenyl, -aryl, -benzyl, -alkylamido, -alkylcarboxy, —$C_1$–$C_5$ alkylene-C(O)O—$C_1$–$C_5$ alkyl, —$C_1$–$C_5$ alkylene-OC(O)—$C_1$–$C_5$ alkyl, or a 5–10 membered aromatic or non-aromatic carbocycle in which 1–4 ring carbon atoms are independently replaced with a N, O or S atom, at least one of which is a nitrogen atom; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat Parkinson's disease.

108. A method for treating an inflammatory disease, comprising administering to a subject in need thereof a compound or a pharmaceutically acceptable hydrate or salt of a compound having the formula:

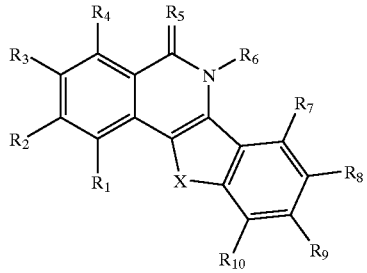

wherein:

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), $NO_2$ or -A-B; wherein at least one of $R^1$, $R^4$ and $R^{10}$ is other than hydrogen;

$R_6$ is —H or $C_1$–$C_4$ alkyl;

A is —$SO_2$—, —$SO_2NH$—, —NHCO—, —NHCONH—, —O—, —CO—, —OC(O)—, —C(O)O—, —CONH—, —CON($C_1$–$C_4$ alkyl)—, —NH—, —$CH_2$—, —S— or —C(S)—;

B is —$C_1$–$C_{10}$ alkyl, —$C_2$–$C_{10}$ alkenyl, —$C_3$–$C_8$ carbocycle, -aryl, $NH_2$, -alkylamino, -aminodialkyl, -arylamido, —C(O)OH, —C(O)O—($C_1$–$C_5$ alkyl), —C(O)O-phenyl, —$NZ_1Z_2$, a 5–10 membered aromatic or non-aromatic carbocycle in which 1–4 of the ring carbon atoms are independently replaced with a N, O or S atom, or B is a $C_1$–$C_5$ alkyl group in which one of the $C_1$–$C_5$ alkyl group's hydrogen atoms is replaced with a 5–10 membered aromatic or non-aromatic carbocycle in which 1–4 of the carbocycle's ring carbon atoms are independently replaced with a N, O or S atom; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the inflammatory disease.

109. The method of claim 108, wherein the subject is a human.

110. The method of claim 108, wherein the inflammatory disease is an inflammatory disease of a joint, a chronic inflammatory disease of the gum, an inflammatory bowel disease, an inflammatory lung disease, an inflammatory disease of the central nervous system, or an inflammatory disease of the eye.

111. The method of claim 108, wherein the inflammatory disease is gram-positive shock, gram negative shock, hemorrhagic shock, anaphylactic shock, traumatic shock and chemotherapeutic shock.

112. A method for treating a reperfusion disease, comprising administering to a subject in need thereof a compound or a pharmaceutically acceptable hydrate or salt of a compound having the formula:

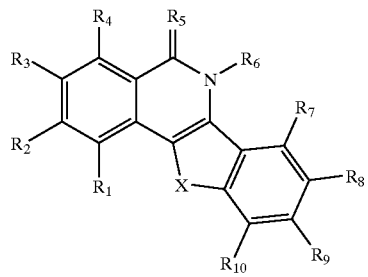

wherein:

$R_1$, $R_2$, $R_3$, $R_4$, $R_7$, $R_5$, $R_9$ and $R_{10}$ are independently -hydrogen, -halo, -hydroxy, —O—($C_1$–$C_5$ alkyl), —$C_1$, —$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), —$NO_2$ or -A-B; wherein at least one of $R^1$, $R^4$ and $R^{10}$ is other than hydrogen;

$R_6$ is —H or $C_1$–$C_4$ alkyl;

A is —$SO_2$—, —$SO_2NH$—, —NHCO—, —NHCONH—, —O—, —CO—, —OC(O)—, —C(O)O—, —CONH—, —CON($C_1$–$C_4$ alkyl)—, —NH—, —$CH_2$—, —S— or —C(S)—;

B is —$C_1$–$C_{10}$ alkyl, —$C_2$–$C_{10}$ alkenyl, —$C_3$–$C_8$ carbocycle, -aryl, $NH_2$, -alkylamino, -aminodialkyl, -arylamido, —C(O)OH, —C(O)O—($C_1$–$C_5$ alkyl), —C(O)O-phenyl, —$NZ_1Z_2$, a 5–10 membered aromatic or non-aromatic carbocycle in which 1–4 of the ring carbon atoms are independently replaced with a N, O or S atom, or B is a $C_1$–$C_5$ alkyl group in which one of the $C_1$–$C_5$ alkyl group's hydrogen atoms is replaced with a 5–10 membered aromatic or non-aromatic carbocycle in which 1–4 of the carbocycle's ring carbon atoms are independently replaced with a N, O or S atom; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —NH$_2$; or N, Z$_3$ and Z$_4$ taken together to form an unsubstituted or substituted 5–10 membered aromatic or non-aromatic carbocycle in which 1–4 ring carbon atoms are independently replaced with a N, O or S atom, at least one of which is a nitrogen atom; or N, Z$_1$ and Z$_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the inflammatory disease.

113. The method of claim 112, wherein the reperfusion disease is myocardial infraction.

114. The method of claim 112, wherein the reperfusion disease is stroke.

115. The method of claim 112, wherein the subject is a human.

116. A method for treating diabetes or a diabetic complication, comprising administering to a subject in need thereof a compound or a pharmaceutically acceptable hydrate or salt of a compound having the formula:

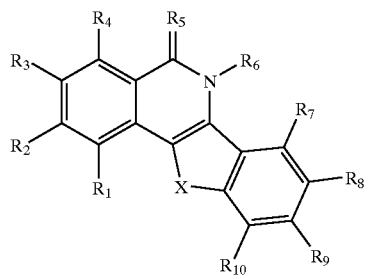

wherein:

R$_1$, R$_2$, R$_3$, R$_4$, R$_7$, R$_8$, R$_9$ and R$_{10}$ are independently -hydrogen, -halo, -hydroxy, —O—(C$_1$-C$_5$ alkyl), —C$_1$, —C$_{10}$ alkyl, -alkylhalo, —C$_2$-C$_{10}$ alkenyl, —C$_3$-C$_8$ carbocycle, -aryl, —NH$_2$, -alkylamino, —C(O)OH, —C(O)O(C$_1$-C$_5$ alkyl), —OC(O)(C$_1$-C$_5$ alkyl), NO$_2$ or -A-B; wherein at least one of R$^1$, R$^4$ and R$^{10}$ is other than hydrogen;

R$_6$ is —H or C$_1$-C$_4$ alkyl;

A is —SO$_2$—, —SO$_2$NH—, —NHCO—, —NHCONH—, —O—, —CO—, —OC(O)—, —C(O)O—, —CONH—, —CON(C$_1$-C$_4$ alkyl)—, —NH—, —CH$_2$—, —S— or —C(S)—;

B is —C$_1$-C$_{10}$ alkyl, —C$_2$-C$_{10}$ alkenyl, —C$_3$-C$_8$ carbocycle, -aryl, NH$_2$, -alkylamino, -aminodialkyl, -arylamido, —C(O)OH, —C(O)O—(C$_1$-C$_5$ alkyl), —C(O)O-phenyl, —NZ$_1$Z$_2$, a 5–10 membered aromatic or non-aromatic carbocycle in which 1–4 of the ring carbon atoms are independently replaced with a N, O or S atom, or B is a C$_1$-C$_5$ alkyl group in which one of the C$_1$-C$_5$ alkyl group's hydrogen atoms is replaced with a 5–10 membered aromatic or non-aromatic carbocycle in which 1–4 of the carbocycle's ring carbon atoms are independently replaced with a N, O or S atom; and Z$_1$ and Z$_2$ are independently —H or —C$_1$-C$_{10}$ alkyl, which is unsubstituted or substituted with one or more of -halo, —OH or —N(Z$_3$)(Z$_4$), where Z$_3$ and Z$_4$ are independently, —H or —C$_1$-C$_5$ alkyl, which is unsubstituted or substituted with one or more of -halo, -hydroxy or —NH$_2$; or N, Z$_3$ and Z$_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, Z$_1$ and Z$_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat diabetes or the diabetic complication.

117. A method for treating reoxygenation injury resulting from organ transplantation, the method comprising administering to a subject in need thereof a compound or a pharmaceutically acceptable hydrate or salt of a compound having the formula:

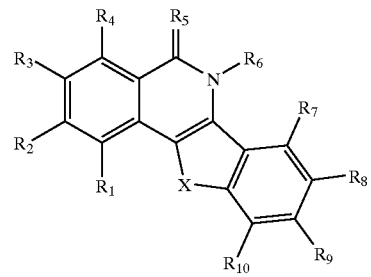

wherein:

R$_1$, R$_2$, R$_3$, R$_4$, R$_7$, R$_8$, R$_9$ and R$_{10}$ are independently -hydrogen, -halo, -hydroxy, —O—(C$_1$-C$_5$ alkyl), —C$_1$, —C$_{10}$ alkyl, -alkylhalo, —C$_2$-C$_{10}$ alkenyl, —C$_3$-C$_8$ carbocycle, -aryl, —NH$_2$, -alkylamino, —C(O)OH, —C(O)O(C$_1$-C$_5$ alkyl), —OC(O)(C$_1$-C$_5$ alkyl), NO$_2$ or -A-B; wherein at least one of R$^1$, R$^4$ and R$^{10}$ is other than hydrogen;

R$_6$ is —H or C$_1$-C$_4$ alkyl;

A is —SO$_2$—, —SO$_2$NH—, —NHCO—, —NHCONH—, —O—, —CO—, —OC(O)—, —C(O)O—, —CONH—, —CON(C$_1$-C$_4$ alkyl)—, —NH—, —CH$_2$—, —S— or —C(S)—;

B is —C$_1$-C$_{10}$ alkyl, —C$_2$-C$_{10}$ alkenyl, —C$_3$-C$_8$ carbocycle, -aryl, NH$_2$, -alkylamino, -aminodialkyl, -arylamido, —C(O)OH, —C(O)O—(C$_1$-C$_5$ alkyl), —C(O)O-phenyl, —NZ$_1$Z$_2$, a 5–10 membered aromatic or non-aromatic carbocycle in which 1–4 of the ring carbon atoms are independently replaced with a N, O or S atom, or B is a C$_1$-C$_5$ alkyl group in which one of the C$_1$-C$_5$ alkyl group's hydrogen atoms is replaced with a 5–10 membered aromatic or non-aromatic carbocycle in which 1–4 of the carbocycle's ring carbon atoms are independently replaced with a N, O or S atom; and Z$_1$ and Z$_2$ are independently —H or —C$_1$-C$_{10}$ alkyl, which is unsubstituted or substituted with one or more of -halo, —OH or —N(Z$_3$)(Z$_4$) where Z$_3$ and Z$_4$ are independently, —H or —C$_1$-C$_5$ alkyl, which is unsubstituted or substituted with one or more of -halo, -hydroxy or —NH$_2$; or N, Z$_3$ and Z$_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, Z$_1$ and Z$_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the reoxygenation injury.

118. A method for treating Parkinson's disease, comprising administering to a subject in need thereof a compound or a pharmaceutically acceptable hydrate or salt of a compound having the formula:

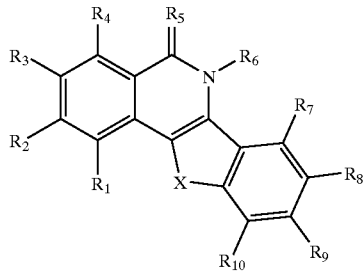

wherein:

$R_6$ is —H or $C_1$-$C_4$ alkyl;

$R_1$, $R_2$, $R_3$, $R_4$, $R_7$, $R_8$, $R_9$ and $R_{10}$ are independently -hydrogen, -halo, -hydroxy, —O—($C_1$-$C_5$ alkyl), —$C_1$, —$C_{10}$ alkyl, -alkylhalo, —$C_2$-$C_{10}$ alkenyl, —$C_3$-$C_8$ carbocycle, -aryl, —$NH_2$, -alkylamino, —C(O)OH, —C(O)O($C_1$-$C_5$ alkyl), —OC(O)($C_1$-$C_5$ alkyl), —$NO_2$ or -A-B; wherein at least one of $R^1$, $R^4$ and $R^{10}$ is other than hydrogen;

A is —$SO_2$—, —$SO_2NH$—, —NHCO—, —NHCONH—, —O—, —CO—, —OC(O)—, —C(O)O—, —CONH—, —CON($C_1$-$C_4$ alkyl)—, —NH—, —$CH_2$—, —S— or —C(S)—;

B is —$C_1$-$C_{10}$ alkyl, —$C_2$-$C_{10}$ alkenyl, —$C_3$-$C_8$ carbocycle, -aryl, $NH_2$, -alkylamino, -aminodialkyl, -arylamido, —C(O)OH, —C(O)O—($C_1$-$C_5$ alkyl), —C(O)O-phenyl, —$NZ_1Z_2$, a 5–10 membered aromatic or non-aromatic carbocycle in which 1–4 of the ring carbon atoms are independently replaced with a N, O or S atom, or B is a $C_1$-$C_5$ alkyl group in which one of the $C_1$-$C_5$ alkyl group's hydrogen atoms is replaced with a 5–10 membered aromatic or non-aromatic carbocycle in which 1–4 of the carbocycle's ring carbon atoms are independently replaced with a N, O or S atom; and $Z_1$ and $Z_2$ are independently —H or —$C_1$-$C_{10}$ alkyl, which is unsubstituted or substituted with one or more of -halo, —OH or —N($Z_3$)($Z_4$), where $Z_3$ and $Z_4$ are independently, —H or —$C_1$-$C_5$ alkyl, which is unsubstituted or substituted with one or more of -halo, -hydroxy or —$NH_2$; or N, $Z_3$ and $Z_4$ are taken together to form an unsubstituted or substituted 5–10 membered aromatic or non-aromatic carbocycle in which 1–4 ring carbon atoms are independently replaced with a N, O or S atom, at least one of which is a nitrogen atom; or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat Parkinson's disease.

119. A method for treating an inflammatory disease, comprising administering to a subject in need thereof a compound or a pharmaceutically acceptable hydrate or salt of a compound having the formula:

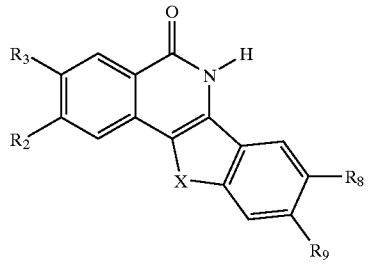

wherein:

X is —$CH_2$— or —O—;

$R_2$ and $R_3$ are independently -hydrogen, -halo, -alkylhalo, -hydroxy, —O—($C_1$-$C_5$ alkyl), —$C_1$-$C_3$ alkyl, —$NO_2$, —$NH_2$, —$CONH_2$, —C(O)OH, —OC(O)—$C_1$-$C_5$ alkyl or —C(O)O—$C_1$-$C_5$ alkyl;

$R_8$ and $R_9$ are independently -hydrogen or -A-B;

A is —$SO_2$—, —$SO_2NH$— or —NHCO—;

B is —$C_1$-$C_3$ alkyl, —$NZ_1Z_2$, -alkylamino or a 5–10 membered aromatic or non-aromatic carbocycle in which 1–4 of the ring carbon atoms are independently replaced with a N, O or S atom, wherein the alkylamino or 5–10 membered aromatic or non-aromatic carbocycle is unsubstituted or substituted with one or more of -alkanol, -alkylamino, -aminoalkyl, -aminodialkyl, a 5–10 membered aromatic or non-aromatic carbocycle in which 1–4 of the ring carbon atoms are independently replaced with a N, O or S atom, wherein the -alkanol, -alkylamino, -aminoalkyl, -aminodialkyl or 5–10 membered aromatic or non-aromatic carbocycle is unsubstituted or substituted with —$C_1$-$C_8$, alkyl or -alkanol; and $Z_1$ and $Z_2$ are independently -hydrogen or —$C_1$-$C_8$ alkyl, which is unsubstituted or substituted with one or more of -hydroxy or —$NZ_3Z_4$, where $Z_3$ and $Z_4$ are independently —H or —$C_1$-$C_3$ alkyl, which is unsubstituted or substituted with one or more of -hydroxy or —$NH_2$, or N, $Z_3$ and $Z_4$ are taken together to a 5–10 membered aromatic or non-aromatic carbocycle in which 1–4 ring carbon atoms are independently replaced with a N, O or S atom, at least one of which is a nitrogen atom, or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the inflammatory disease.

120. The method of claim 119, wherein the subject is a human.

121. The method of claim wherein the inflammatory disease is an inflammatory disease of a joint, a chronic inflammatory disease of the gum, an inflammatory bowel disease, an inflammatory lung disease, an inflammatory disease of the central nervous system, or an inflammatory disease of the eye.

122. The method of claim 119, wherein the inflammatory disease is gram-positive shock, gram negative shock, hemorrhagic shock, anaphylactic shock, traumatic shock and chemotherapeutic shock.

123. A method for treating a reperfusion disease, comprising administering to a subject in need thereof a compound or a pharmaceutically acceptable hydrate or salt of a compound having the formula:

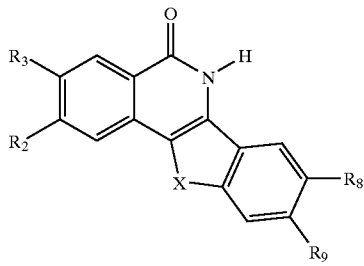

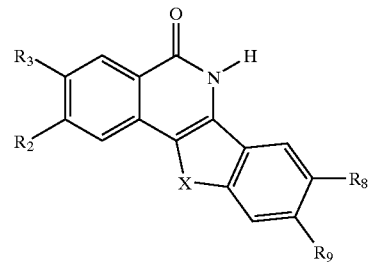

wherein:

X is —CH$_2$— or —O—;

R$_2$ and R$_3$ are independently -hydrogen, -halo, -alkylhalo, -hydroxy, —O—(C$_1$–C$_5$ alkyl), —C$_1$–C$_3$ alkyl, —NO$_2$, —NH$_2$, —CONH$_2$, —C(O)OH, —OC(O)—C$_1$–C$_5$ alkyl or —C(O)O—C$_1$–C$_5$ alkyl;

R$_8$ and R$_9$ are independently -hydrogen or -A-B;

A is —SO$_2$—, —SO$_2$NH— or —NHCO—;

B is —C$_1$–C$_3$ alkyl, —NZ$_1$Z$_2$, -alkylamino or a 5–10 membered aromatic or non-aromatic carbocycle in which 1–4 of the ring carbon atoms are independently replaced with a N, O or S atom, wherein the alkylamino or 5–10 membered aromatic or non-aromatic carbocycle is unsubstituted or substituted with one or more of -alkanol, -alkylamino, -aminoalkyl, -aminodialkyl a 5–10 membered aromatic or non-aromatic carbocycle in which 1–4 of the ring carbon atoms are independently replaced with a N, O or S atom, wherein the -alkanol, -alkylamino, -aminoalkyl, -aminodialkyl or 5–10 membered aromatic or non-aromatic carbocycle is unsubstituted or substituted with —C$_1$–C$_8$, alkyl or -alkanol; and Z$_1$ and Z$_2$ are independently -hydrogen or —C$_1$–C$_8$ alkyl, which is unsubstituted or substituted with one or more of -hydroxy or —NZ$_3$Z$_4$, where Z$_3$ and Z$_4$ are independently —H or —C$_1$–C$_3$ alkyl, which is unsubstituted or substituted with one or more of -hydroxy or —NH$_2$, or N, Z$_3$ and Z$_4$ are taken together to a 5–10 membered aromatic or non-aromatic carbocycle in which 1–4 ring carbon atoms are independently replaced with a N, O or S atom, at least one of which is a nitrogen atom, or N, Z$_1$ and Z$_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the reperfusion disease.

124. The method of claim 123, wherein the reperfusion disease is myocardial infarction.

125. The method of claim 123, wherein the reperfusion disease is stroke.

126. The method of claim 123, wherein the subject is a human.

127. A method for treating diabetes or a diabetic complication, comprising administering to a subject in need thereof a compound or a pharmaceutically acceptable hydrate or salt of a compound having the formula:

wherein:

X is —CH$_2$— or —O—;

R$_2$ and R$_3$ are independently -hydrogen, -halo, -alkylhalo, -hydroxy, —O—(C$_1$–C$_5$ alkyl), —C$_1$–C$_3$ alkyl, —NO$_2$, —NH$_2$, —CONH$_2$, —C(O)OH, —OC(O)—C$_1$–C$_5$ alkyl or —C(O)O—C$_1$–C$_5$ alkyl;

R$_8$ and R$_9$ are independently -hydrogen or -A-B;

A is —SO$_2$—, —SO$_2$NH— or —NHCO—;

B is —C$_1$–C$_3$ alkyl, —NZ$_1$Z$_2$, -alkylamino or a 5–10 membered aromatic or non-aromatic carbocycle in which 1–4 of the ring carbon atoms are independently replaced with a N, O or S atom, wherein the alkylamino or 5–10 membered aromatic or non-aromatic carbocycle is unsubstituted or substituted with one or more of -alkanol, -alkylamino, -aminoalkyl, -aminodialkyl a 5–10 membered aromatic or non-aromatic carbocycle in which 1–4 of the ring carbon atoms are independently replaced with a N, O or S atom, wherein the -alkanol, -alkylamino, -aminoalkyl, -aminodialkyl or 5–10 membered aromatic or non-aromatic carbocycle is unsubstituted or substituted with —C$_1$–C$_8$, alkyl or -alkanol; and Z$_1$ and Z$_2$ are independently -hydrogen or —C$_1$–C$_8$ alkyl, which is unsubstituted or substituted with one or more of -hydroxy or —NZ$_3$Z$_4$, where Z$_3$ and Z$_4$ are independently —H or —C$_1$–C$_3$ alkyl, which is unsubstituted or substituted with one or more of -hydroxy or —NH$_2$, or N, Z$_3$ and Z$_4$ are taken together to a 5–10 membered aromatic or non-aromatic carbocycle in which 1–4 ring carbon atoms are independently replaced with a N, O or S atom, at least one of which is a nitrogen atom, or N, Z$_1$ and Z$_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat diabetes or the diabetic complication.

128. A method for treating reoxygenation injury resulting from organ transplantation, the method comprising administering to a subject in need thereof a compound or a pharmaceutically acceptable hydrate or salt of a compound having the formula:

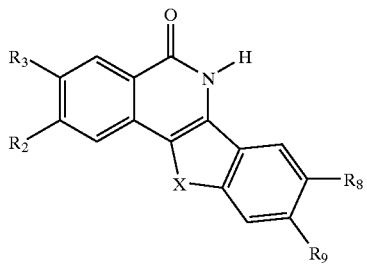

wherein:

X is —CH$_2$— or —O—;

R$_2$ and R$_3$ are independently -hydrogen, -halo, -alkylhalo, -hydroxy, —O—(C$_1$-C$_5$ alkyl), —C$_1$-C$_3$ alkyl, —NO$_2$, —NH$_2$, —CONH$_2$, —C(O)OH, —OC(O)—C$_1$-C$_5$ alkyl or —C(O)O—C$_1$-C$_5$ alkyl;

R$_8$ and R$_9$ are independently -hydrogen or -A-B;

A is —SO$_2$—, —SO$_2$NH— or —NHCO—;

B is —C$_1$-C$_3$ alkyl, —NZ$_1$Z$_2$, -alkylamino or a 5–10 membered aromatic or non-aromatic carbocycle in which 1–4 of the ring carbon atoms are independently replaced with a N, O or S atom, wherein the alkylamino or 5–10 membered aromatic or non-aromatic carbocycle is unsubstituted or substituted with one or more of -alkanol, -alkylamino, -aminoalkyl, -aminodialkyl a 5–10 membered aromatic or non-aromatic carbocycle in which 1–4 of the ring carbon atoms are independently replaced with a N, O or S atom, wherein the -alkanol, -alkylamino, -aminoalkyl, -aminodialkyl or 5–10 membered aromatic or non-aromatic carbocycle is unsubstituted or substituted with —C$_1$-C$_8$, alkyl or -alkanol; and Z$_1$ and Z$_2$ are independently -hydrogen or —C$_1$-C$_8$ alkyl, which is unsubstituted or substituted with one or more of -hydroxy or —NZ$_3$Z$_4$, where Z$_3$ and Z$_4$ are independently —H or —C$_1$-C$_3$ alkyl, which is unsubstituted or substituted with one or more of -hydroxy or —NH$_2$, or N, Z$_3$ and Z$_4$ are taken together to a 5–10 membered aromatic or non-aromatic carbocycle in which 1–4 ring carbon atoms are independently replaced with a N, O or S atom, at least one of which is a nitrogen atom, or N, Z$_1$ and Z$_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat the reoxygenation injury.

129. A method for treating Parkinson's disease, comprising administering to a subject in need thereof a compound or a pharmaceutically acceptable hydrate or salt of a compound having the formula:

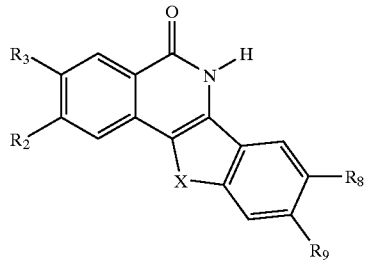

wherein:

X is —CH$_2$— or —O—;

R$_2$ and R$_3$ are independently -hydrogen, -halo, -alkylhalo, -hydroxy, —O—(C$_1$-C$_5$ alkyl), —C$_1$-C$_3$ alkyl, —NO$_2$, —NH$_2$, —CONH$_2$, —C(O)OH, —OC(O)—C$_1$-C$_5$ alkyl or —C(O)O—C$_1$-C$_5$ alkyl;

R$_8$ and R$_9$ are independently -hydrogen or -A-B;

A is —SO$_2$—, —SO$_2$NH— or —NHCO—;

B is —C$_1$-C$_3$ alkyl, —NZ$_1$Z$_2$, -alkylamino or a 5–10 membered aromatic or non-aromatic carbocycle in which 1–4 of the ring carbon atoms are independently replaced with a N, O or S atom, wherein the alkylamino or 5–10 membered aromatic or non-aromatic carbocycle is unsubstituted or substituted with one or more of -alkanol, -alkylamino, -aminoalkyl, -aminodialkyl a 5–10 membered aromatic or non-aromatic carbocycle in which 1–4 of the ring carbon atoms are independently replaced with a N, O or S atom, wherein the -alkanol, -alkylamino, -aminoalkyl, -aminodialkyl or 5–10 membered aromatic or non-aromatic carbocycle is unsubstituted or substituted with —C$_1$-C$_8$, alkyl or -alkanol; and Z$_1$ and Z$_2$ are independently -hydrogen or —C$_1$-C$_8$ alkyl, which is unsubstituted or substituted with one or more of -hydroxy or —NZ$_3$Z$_4$, where Z$_3$ and Z$_4$ are independently —H or —C$_1$-C$_3$ alkyl, which is unsubstituted or substituted with one or more of -hydroxy or —NH$_2$, or N, Z$_3$ and Z$_4$ are taken together to a 5–10 membered aromatic or non-aromatic carbocycle in which 1–4 ring carbon atoms are independently replaced with a N, O or S atom, at least one of which is a nitrogen atom, or N, Z$_1$ and Z$_2$ are taken together to form a 5–10 membered aromatic or non-aromatic carbocycle in which 1–4 ring carbon atoms are independently replaced with a N, O or S atom, at least one of which is a nitrogen atom, in an amount sufficient to treat Parkinson's disease.

130. A compound having the formula:

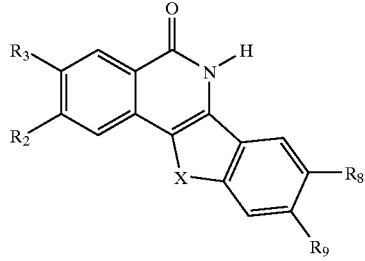

or a pharmaceutically acceptable hydrate or salt thereof, wherein:

X is —CR$_2$— or —O—;

$R_2$ and $R_3$ are independently -hydrogen, -halo, -alkylhalo, -hydroxy, —O—($C_1$–$C_5$ alkyl), —$C_1$–$C_3$ alkyl, —$NO_2$, —$NH_2$, —$CONH_2$, —C(O)OH, —OC(O)—$C_1$–$C_5$ alkyl or —C(O)O—$C_1$–$C_5$ alkyl;

$R_8$ is -hydrogen and $R_9$ is -A-B, or $R_8$ is -A-B and $R_9$ is -hydrogen;

A is —$SO_2$—, —$SO_2$NH— or —NHCO—;

B is —$C_1$–$C_3$ alkyl, —$NZ_1Z_2$, -alkylamino, or a 5–10 membered aromatic or non-aromatic carbocycle in which 1–4 of the ring carbon atoms are independently replaced with a N, O or S atom, wherein the alkylamino or 5–10 membered aromatic or non-aromatic carbocycle is unsubstituted or substituted with one or more of -alkanol, -alkylamino, -aminoalkyl, -aminodialkyl or a 5–10 membered aromatic or non-aromatic carbocycle in which 1–4 of the ring carbon atoms are independently replaced with a N, O or S atom, wherein the -alkanol, -alkylamino, -aminoalkyl, -aminodialkyl or 5–10 membered aromatic or non-aromatic carbocycle is unsubstituted or substituted with —$C_1$–$C_8$, alkyl or -alkanol; and $Z_1$ and $Z_2$ are independently -hydrogen or —$C_1$–$C_8$ alkyl, which is unsubstituted or substituted with one or more of -hydroxy or —$NZ_3Z_4$, where $Z_3$ and $Z_4$ are independently —H or —$C_1$–$C_3$ alkyl, which is unsubstituted or substituted with one or more of -hydroxy or —$NH_2$, or N, $Z_3$ and $Z_4$ are taken together to a 5–10 membered aromatic or non-aromatic carbocycle in which 1–4 ring carbon atoms are independently replaced with a N, O or S atom, at least one of which is a nitrogen atom, or N, $Z_1$ and $Z_2$ are taken together to form a 5–10 membered aromatic or non-aromatic carbocycle in which 1–4 ring carbon atoms are independently replaced with a N, O or S atom, at least one of which is a nitrogen atom.

131. A composition comprising an effective amount of a compound or pharmaceutically acceptable salt or hydrate of a compound of claim 130 and a pharmaceutically acceptable carrier.

* * * * *

UNITED STATES PATENT AND TRADEMARK OFFICE
CERTIFICATE OF CORRECTION

PATENT NO. : 6,828,319 B2
DATED : December 7, 2004
INVENTOR(S) : Prakash Jagtap et al.

It is certified that error appears in the above-identified patent and that said Letters Patent is hereby corrected as shown below:

Column 32,
Line 21, "CH2, R1, R2, R3, R4, R7, R8, R9 and R10" should read -- $CH_2$, then $R_1$, $R_2$, $R_3$, $R_4$, $R_7$, $R_8$, $R_9$ and $R_{10}$ --;
Line 29, "aminodiallcyl" should read -- aminodialkyl --;
Line 40, "alkyihalo" should read -- alkylhalo --;

Column 34,
Line 2, "$C_3 14 C_3$" should read -- $C_3$-$C_8$ --;
Line 2, "wherein n is an integer" should read -- -$(CH_2)_n$D, wherein n is an integer --;

Column 35,
Line 2, "wherein n is an integer" should read -- -$(CH_2)_n$D, wherein n is an integer --;

Column 36,
Line 22, "R2, R3, R8 and R9" should read -- $R_2$, $R_3$, $R_8$, and $R_9$ --;

Column 38,
Line 52, "replaced" should read -- replaced --;

Column 43,
Line 45, the two structures, 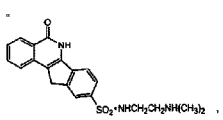 should read 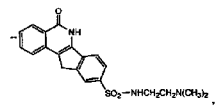 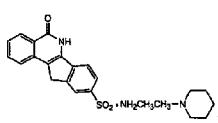

UNITED STATES PATENT AND TRADEMARK OFFICE
CERTIFICATE OF CORRECTION

PATENT NO. : 6,828,319 B2
DATED : December 7, 2004
INVENTOR(S) : Prakash Jagtap et al.

It is certified that error appears in the above-identified patent and that said Letters Patent is hereby corrected as shown below:

Column 44,
Lines 1-65, the five structures,

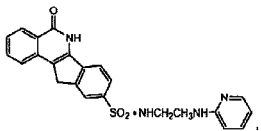 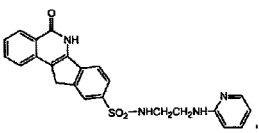
should read

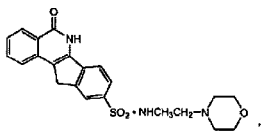 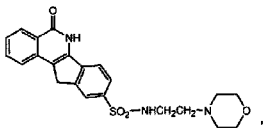

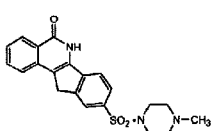 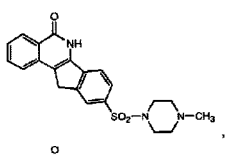

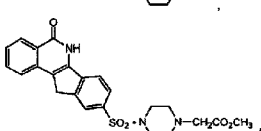

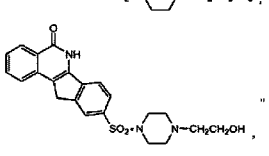 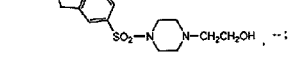

UNITED STATES PATENT AND TRADEMARK OFFICE
CERTIFICATE OF CORRECTION

PATENT NO. : 6,828,319 B2  
DATED : December 7, 2004  
INVENTOR(S) : Prakash Jagtap et al.

It is certified that error appears in the above-identified patent and that said Letters Patent is hereby corrected as shown below:

Column 45,  
Lines 1-65, the five structures,

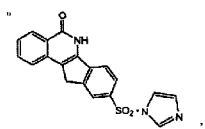 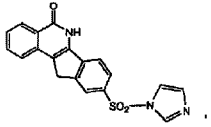

should read

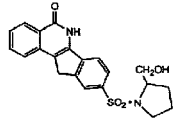 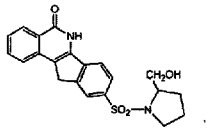

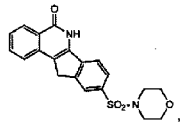 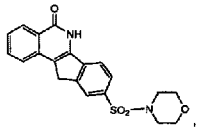

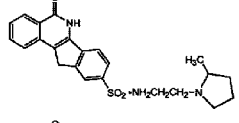 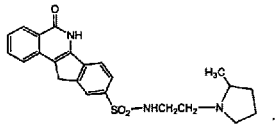

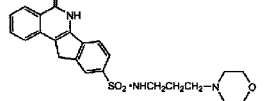 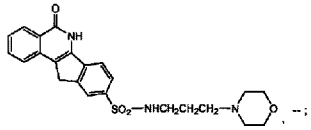

UNITED STATES PATENT AND TRADEMARK OFFICE
CERTIFICATE OF CORRECTION

PATENT NO. : 6,828,319 B2
DATED : December 7, 2004
INVENTOR(S) : Prakash Jagtap et al.

It is certified that error appears in the above-identified patent and that said Letters Patent is hereby corrected as shown below:

Column 46,
Lines 1-65, the five structures,

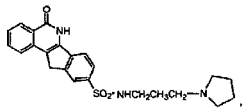
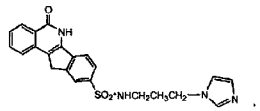
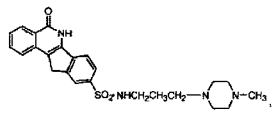 should read 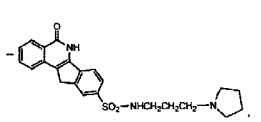
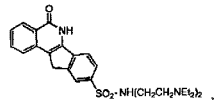 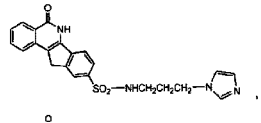
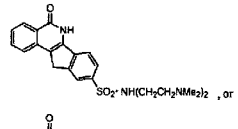 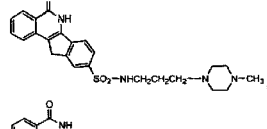
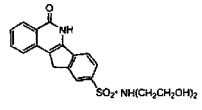 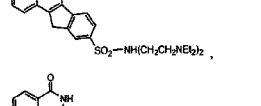
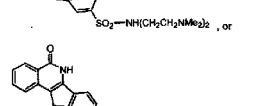
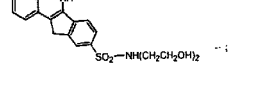

Column 50,
Line 3, "and" should read -- or --;

Column 61,
Line 18, the following language should be inserted after the term "wherein:"

--$R_5$ is NH or S;
$R_6$ is -H or $C_1$-$C_4$ alkyl;
X is -C(O)-, -$CH_2$-, -CH(halo)-, -CH(OH)($CH_2$)$_n$-, -CH(OH)-arylene-, -O-, -NH-,
-S- or -CH($NR_{11}R_{12}$)-, wherein n is an integer ranging from 0-5;
$R_{11}$ and $R_{12}$ are independently -hydrogen or -$C_1$-$C_9$ alkyl, or N, $R_{11}$ and $R_{12}$ are
taken together to form a 5-10 membered aromatic or non-aromatic carbocycle in
which 1-4 ring carbon atoms are independently replaced with a N, O or S atom,
at least one of which is a nitrogen atom;--;

Line 21, "$C_1$-$C_{10}$ alkyl, -alkylhalo, -$C_2$-$C_{10}$ alkenyl" should read --$C_1$-$C_{10}$ alkyl, - alkylhalo, -$C_2$-$C_{10}$ alkenyl--;

Line 23, "$R^1$, $R^4$ and $R^{10}$" should read --$R_1$, $R_4$ and $R_{10}$--;

UNITED STATES PATENT AND TRADEMARK OFFICE
CERTIFICATE OF CORRECTION

PATENT NO. : 6,828,319 B2
DATED : December 7, 2004
INVENTOR(S) : Prakash Jagtap et al.

It is certified that error appears in the above-identified patent and that said Letters Patent is hereby corrected as shown below:

Column 62,
Line 3, "and" should read -- or --;
Line 18, the following language should be inserted after the term "wherein:"

-- $R_5$ is NH or S;
  $R_6$ is -H or $C_1$-$C_4$ alkyl;
  X is -C(O)-, -$CH_2$-, -CH(halo)-, -CH(OH)($CH_2$)$_n$-, -CH(OH)-arylene-, -O-, -NH-,
    -S- or -CH($NR_{11}R_{12}$)-, wherein n is an integer ranging from 0-5;
  $R_{11}$ and $R_{12}$ are independently -hydrogen or -$C_1$-$C_9$ alkyl, or N, $R_{11}$ and $R_{12}$ are
    taken together to form a 5-10 membered aromatic or non-aromatic carbocycle in
    which 1-4 ring carbon atoms are independently replaced with a N, O or S atom,
    at least one of which is a nitrogen atom;--;

Line 23, "$R^{1, R4}$" should read -- $R^4$, $R^4$ --;
Line 24, "$R^{10}$" should read -- $R_{10}$ --;

Column 63,
Line 18, the following language should be inserted after the term "wherein:"

-- $R_5$ is NH or S;
  $R_6$ is -H or $C_1$-$C_4$ alkyl;
  X is -C(O)-, -$CH_2$-, -CH(halo)-, -CH(OH)($CH_2$)$_n$-, -CH(OH)-arylene-, -O-, -NH-,
    -S- or -CH($NR_{11}R_{12}$)-, wherein n is an integer ranging from 0-5;
  $R_{11}$ and $R_{12}$ are independently -hydrogen or -$C_1$-$C_9$ alkyl, or N, $R_{11}$ and $R_{12}$ are
    taken together to form a 5-10 membered aromatic or non-aromatic carbocycle in
    which 1-4 ring carbon atoms are independently replaced with a N, O or S atom,
    at least one of which is a nitrogen atom;--;

Line 23, "$R^{1, R4}$" should read -- $R^1$, $R^4$ --;
Line 24, "$R^{10}$" should read -- $R_{10}$ --;

Column 64,
Line 18, the following language should be inserted after the term "wherein:"

-- $R_5$ is NH or S;
  $R_6$ is -H or $C_1$-$C_4$ alkyl;
  X is -C(O)-, -$CH_2$-, -CH(halo)-, -CH(OH)($CH_2$)$_n$-, -CH(OH)-arylene-, -O-, -NH-,
    -S- or -CH($NR_{11}R_{12}$)-, wherein n is an integer ranging from 0-5;
  $R_{11}$ and $R_{12}$ are independently -hydrogen or -$C_1$-$C_9$ alkyl, or N, $R_{11}$ and $R_{12}$ are
    taken together to form a 5-10 membered aromatic or non-aromatic carbocycle in
    which 1-4 ring carbon atoms are independently replaced with a N, O or S atom,
    at least one of which is a nitrogen atom;--;

Line 23, "$R^{1, R4}$" should read -- $R^1$, $R^4$ --;
Line 24, "$R^{10}$" should read -- $R_{10}$ --;

UNITED STATES PATENT AND TRADEMARK OFFICE
CERTIFICATE OF CORRECTION

PATENT NO. : 6,828,319 B2
DATED : December 7, 2004
INVENTOR(S) : Prakash Jagtap et al.

It is certified that error appears in the above-identified patent and that said Letters Patent is hereby corrected as shown below:

Column 65,
Line 18, the following language should be inserted after the term "wherein:"

-- $R_5$ is NH or S;
$R_6$ is -H or $C_1$-$C_4$ alkyl;
X is -C(O)-, -$CH_2$-, -CH(halo)-, -CH(OH)($CH_2$)$_n$-, -CH(OH)-arylene-, -O-, -NH-, -S- or -CH($NR_{11}R_{12}$)-, wherein n is an integer ranging from 0-5;
$R_{11}$ and $R_{12}$ are independently -hydrogen or -$C_1$-$C_9$ alkyl, or N, $R_{11}$ and $R_{12}$ are taken together to form a 5-10 membered aromatic or non-aromatic carbocycle in which 1-4 ring carbon atoms are independently replaced with a N, O or S atom, at least one of which is a nitrogen atom;--;

Line 26, "$R^{1, R4}$" should read -- $R^1$, $R^4$ --;
Line 27, "$R^{10}$" should read -- $R_{10}$ --;

Column 66,
Line 3, "and" should read -- or --;

Column 69,
Line 42, "$C_1$-$C_8$, alkyl" should read -- $C_1$-$C_8$ alkyl --;

Column 70,
Line 34, "$C_1$-$C_8$, alkyl" should read -- $C_1$-$C_8$ alkyl --;
Line 15, "$CR_2$" should read -- $CH_2$ --; and Column 71,
Line 21, "$C_1$-$C_8$, alkyl" should read -- $C_1$-$C_8$ alkyl --.

Signed and Sealed this

Twenty-sixth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,828,319 B2
DATED : December 7, 2004
INVENTOR(S) : Jagtap et al.

It is certified that error appears in the above-identified patent and that said Letters Patent is hereby corrected as shown below:

Column 32,
Line 30, "$-OH_2$" should read -- $CH_2$ --;

Column 36,
Line 22, "$-OH_2$" should read -- $CH_2$ --;

Column 62,
Line 41, "$-C_1, -C_{10}$" should read -- $C_1-C_{10}$ --;

Column 63,
Line 36, "$-C_1, -C_{10}$" should read -- $C_1-C_{10}$ --;

Column 64,
Line 28, "$-C_1, -C_{10}$" should read -- $C_1-C_{10}$ --;

Column 65,
Line 23, "$-C_1, -C_{10}$" should read -- $C_1-C_{10}$ --;

Signed and Sealed this

Ninth Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,828,319 B2 Page 1 of 1
APPLICATION NO. : 10/233198
DATED : December 7, 2004
INVENTOR(S) : Jagtap et al.

It is certified that error appears in the above-identified patent and that said Letters Patent is hereby corrected as shown below:

Column 24, line 38 "chlorosulfonyl chloride" should read -- $ClSO_3H$ --.

Signed and Sealed this

Twenty-sixth Day of June, 2007

JON W. DUDAS
*Director of the United States Patent and Trademark Office*